(12) United States Patent
Hawkett et al.

(10) Patent No.: US 10,376,589 B2
(45) Date of Patent: Aug. 13, 2019

(54) METHOD FOR THE TREATMENT OF A SOLID TUMOUR

(71) Applicant: The University of Sydney, Sydney (AU)

(72) Inventors: Brian Stanley Hawkett, Mona Vale (AU); Trevor William Hambley, Ashbury (AU); Nicole Sarah Bryce, Glenbrook (AU); Thi Thuy Binh Pham, Earlwood (AU); Nirmesh Jain, Parramatta (AU)

(73) Assignee: The University of Sydney, Sydney (AU)

( * ) Notice: Subject to any disclaimer, the term of this patent is extended or adjusted under 35 U.S.C. 154(b) by 0 days.

(21) Appl. No.: 15/853,069

(22) Filed: Dec. 22, 2017

(65) Prior Publication Data

US 2018/0117160 A1 May 3, 2018

Related U.S. Application Data

(63) Continuation of application No. 14/112,673, filed as application No. PCT/AU2012/000414 on Apr. 20, 2012, now abandoned.
(Continued)

(30) Foreign Application Priority Data

Apr. 20, 2011 (AU) .................................. 2011901495
Feb. 9, 2012 (AU) .................................. 2012900480

(51) Int. Cl.
*A61K 9/00* (2006.01)
*A61K 47/34* (2017.01)
(Continued)

(52) U.S. Cl.
CPC ............ *A61K 47/34* (2013.01); *A61K 31/136* (2013.01); *A61K 31/337* (2013.01);
(Continued)

(58) Field of Classification Search
CPC ...................................................... A61K 47/34
See application file for complete search history.

(56) References Cited

U.S. PATENT DOCUMENTS

| 5,411,730 | A | 5/1995 | Kirpotin et al. |
| 5,916,539 | A | 6/1999 | Pilgrimm |

(Continued)

FOREIGN PATENT DOCUMENTS

| DE | 19624426 A1 | 1/1998 |
| EP | 2000150 A2 | 12/2008 |

(Continued)

OTHER PUBLICATIONS

Extended European Search Report issued from corresponding EP Patent Application No. 12774165.0, dated Sep. 22, 2014.
(Continued)

*Primary Examiner* — Paul W Dickinson
(74) *Attorney, Agent, or Firm* — Banner & Witcoff, Ltd.

(57) ABSTRACT

The present invention relates generally to a method of treating a neoplastic condition and to agents useful for same. More particularly, the present invention is directed to a method of facilitating the treatment of a solid tumor in a localized manner via the co-administration of particulate material and a cellular toxin. The method of the present invention is useful in a range of therapeutic treatments including the treatment of primary and metastatic tumors.

7 Claims, 11 Drawing Sheets

Related U.S. Application Data

(60) Provisional application No. 61/477,382, filed on Apr. 20, 2011.

(51) Int. Cl.

| | | |
|---|---|---|
| *A61K 33/00* | (2006.01) | |
| *A61K 33/24* | (2019.01) | |
| *A61K 45/06* | (2006.01) | |
| *B82Y 5/00* | (2011.01) | |
| *A61K 31/136* | (2006.01) | |
| *A61K 31/337* | (2006.01) | |
| *A61K 31/513* | (2006.01) | |
| *A61K 31/704* | (2006.01) | |
| *A61K 47/02* | (2006.01) | |
| *A61K 51/12* | (2006.01) | |

(52) U.S. Cl.
CPC .......... *A61K 31/513* (2013.01); *A61K 31/704* (2013.01); *A61K 33/00* (2013.01); *A61K 33/24* (2013.01); *A61K 45/06* (2013.01); *A61K 47/02* (2013.01); *A61K 51/1244* (2013.01); *B82Y 5/00* (2013.01); *A61K 9/0019* (2013.01)

(56) References Cited

U.S. PATENT DOCUMENTS

| | | | |
|---|---|---|---|
| 6,106,866 | A | 8/2000 | Ranney |
| 6,855,270 | B2 | 2/2005 | Mumper et al. |
| 6,979,466 | B2 | 12/2005 | Lesniak et al. |
| 7,217,735 | B1 | 5/2007 | Au et al. |
| 7,348,026 | B2 | 3/2008 | Sung et al. |
| 7,387,900 | B2 | 6/2008 | Tamarkin et al. |
| 7,479,483 | B2 | 1/2009 | Ponzoni et al. |
| 2004/0038303 | A1 | 2/2004 | Unger |
| 2004/0076683 | A1 | 4/2004 | Hoarau et al. |
| 2004/0082521 | A1 | 4/2004 | Singh |
| 2005/0209310 | A1 | 9/2005 | Chaplin et al. |
| 2006/0181997 | A1 | 8/2006 | Tanase |
| 2008/0014150 | A1 | 1/2008 | Sabin |
| 2009/0041673 | A1 | 2/2009 | Jon et al. |
| 2009/0226372 | A1 | 9/2009 | Ruoslahti et al. |
| 2009/0297620 | A1 | 12/2009 | Kanehira et al. |
| 2011/0137235 | A1 | 6/2011 | Kanehira et al. |

FOREIGN PATENT DOCUMENTS

| | | |
|---|---|---|
| EP | 2305214 A1 | 4/2011 |
| WO | 03/040308 A2 | 5/2003 |
| WO | 2003/055520 A1 | 7/2003 |
| WO | 2005/077336 A1 | 8/2005 |
| WO | 2006/116403 A2 | 11/2006 |
| WO | 2007/069272 A2 | 6/2007 |
| WO | 2009/031859 A2 | 3/2009 |
| WO | 2009/073193 A2 | 6/2009 |
| WO | 2009/137890 A1 | 11/2009 |
| WO | 2010/016581 A1 | 2/2010 |

OTHER PUBLICATIONS

Search Report issued from corresponding Turkish Application No. 2015/12996, dated Jun. 7, 2016.
Qin, Y. et al., Highly water-dispersible Ti02 nanoparticles for doxorubicin delivery: effect of loading mode on therapeutic efficacy, Journal of Materials Chemistry, 2011, vol. 21, pp. 18003-18010.
Bryce, N. S. et al, The compositions and end-group functionality of sterically stabilized nanoparticles enhances the effectiveness of co-administered cytotoxins, Biomaterials Science, 2013, vol. 1, No. 12, p. 1260.
Arias et al., National Vital Statistics Reports, vol. 52, No. 3, Sep. 18, 2011, pp. 111-115.
Bender et al., "Immunotherapy of Human Glioma Xenografts with Unlabeled, 131I-, or 125-I-labled Monoclonal Antibody 425 to Epidermal Growth Factor Receptor," Cancer Research 52: 121-126, 1992.
Christiansen et al., "Biological impediments to monoclonal antibody-based cancer immunotherapy," Molecular Cancer Therapy 3: 1493-1501, 2004.
Britz-Cunningham et al., "Molecular Targeting with Radionuclides: State of the Science," Journal of Nuclear Medicine 44: 1945-1961, 2003.
Dadachova et al., "Dead cells in melanoma tumors provide abundant antigen for targeted delivery of ionizing radiation by mAb to melanin," PNAS vol. 101, No. 41 (Oct. 12, 2004) pp. 14865-14870, 2004.
Griffiths et al., "Cytotoxicity With Auger Erlectron-Emitting Radionuclides Delivered by Antibodies," International Journal of Cancer 81: 985-992, 1999.
Lawrence TS., "Radiation Sensitizers and Targeted Therapies," Oncology Journal, Dec. 1, 2003, pp. 1-6, Published on Cancer Network (http://www.cancernetwork.com).
Liu et al., "Bifunicitional Chelators for Therapeutic Lanthanide Radiopharmaceuticals," Bioconjugate Chemistry 12: 7-34, 2001.
Massart R., "Preparation of Aqueous Magnetic Liquids in Alkaline and Acidic Media," IEEE Transactions on Magnetics, vol. MAG-17, No. 2, Mar. 1981, pp. 1247-1248.
O'Donoghue et al., "Relationships between Tumor Size and Curability for Uniformly Targeted Therapy with Beta-Emitting Radionuclides," Journal of Nuclear Medicine, vol. 36, No. 10, Oct. 1995, pp. 1902-1909.
Sellers et al., "Apoptosis and cancer drug targeting," Downloaded on Mar. 4, 2014, The Journal of Clinical Investigation, Dec. 1999, vol. 104, No. 12, pp. 1655-1661, More information at www.jci.org/articles/view/9053.
Waldmann T.A., "Monoclonal Antibodies in Diagnosis and Therapy," Science, Jun. 21, 1991; 252, 5013; ProQuest, pp. 1657-1662.
Xue et al., "Bystander effect produced by radiolabeled tumor cells in vivo," PNAS, vol. 99, No. 21, pp. 13765-13770, (Oct. 15, 2002).
Primeau, A.J. et al., "The Distribution of the Anitcancer Drug Doxorubicin in Relation to Blood Vesselsd in Solid Tumors," Clin Cancer Res 2005; 11:8782-8788.
Minchinton, A.I. et al., "Drug Penetration in solid tumours," National Reviews Cancer, vol. 6, Aug. 2006, pp. 583-592.
Khare P. et al., "Bioconjugates: Harnessing Potential for Effective Therapeutics," Critical Reviews in Therapeutic Drug Carrier Systems, 2009, vol. 26, No. 2, pp. 119-155.
Senthilkumar M. et al., "Long Circulating PEGylated Poly (D,L-lactide-co-glycolide) nanoparticulate delivery of Docetaxel to solid tumors," Journal of Drugs Targeting, Jun. 2008, vol. 16, No. 5, pp. 424-435.
Boyer C et al., "The design and utility of polymer-stabilized iron-oxide nanoparticles for nanomedicie application," NPG Asia Materials, 2010, vol. 2, No. 1, pp. 23-30.
Jain N. et al., "Optimized Steric Stabilization of Aqueous Ferrofluids and Magnetic Nanoparticles," Langmuir Article, 2010, vol. 26, No. 6, pp. 4465-4472.
Wang Y. et al., "Formulation and pharmacokinetic evaluation of a paclitaxel nanosuspension for intravenous delivery," International Journal of Nanomedicine, Jul. 2011, vol. 6, pp. 1497-1507.
Riess G., "Micellization of Block Copolymers," Progress in Polymer Science, 2003, vol. 28, pp. 1107-1170.
Petri-Fink et al., "Development of functionalized superparamagnetic iron oxide nanoparticles for interaction with human cancer cells," Biomaterials 26 (2005) 2685-2694.

METHOD FOR THE TREATMENT OF A SOLID TUMOUR

RELATED APPLICATIONS

This application is a continuation of U.S. application Ser. No. 14/112,673, filed Dec. 4, 2013, which is a National Stage Application under 35 U.S.C. 371 of co-pending PCT application PCT/AU2012/000414 designating the United States and filed Apr. 20, 2012; which claims the benefit of AU application number 2012900480 and filed Feb. 9, 2012; which claims the benefit of AU application number 2011901495 and filed Apr. 20, 2011; which claims the benefit of U.S. application No. 61/477,382 and filed Apr. 20, 2011.

FIELD OF THE INVENTION

The present invention relates generally to a method of treating a neoplastic condition and to agents useful for same. More particularly, the present invention is directed to a method of facilitating the treatment of a solid tumour in a localised manner via the co-administration of particulate material and a cellular toxin. The method of the present invention is useful in a range of therapeutic treatments including the treatment of primary and metastatic tumours.

BACKGROUND OF THE INVENTION

Bibliographic details of the publications referred to by the author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Malignant tumours, or cancers, grow in an uncontrolled manner, invade normal tissues, and often metastasize and grow at sites distant from the tissue of origin. In general, cancers are derived from one or only a few normal cells that have undergone a poorly understood process called malignant transformation. Cancers can arise from almost any tissue in the body. Those derived from epithelial cells, called carcinomas, are the most common kinds of cancers. Sarcomas are malignant tumours of mesenchymal tissues, arising from cells such as fibroblasts, muscle cells, and fat cells. Solid malignant tumours of lymphoid tissues are called lymphomas, and marrow and blood-borne malignant tumours of lymphocytes and other hematopoietic cells are called leukaemias.

Cancer is one of the three leading causes of death in industrialised nations. As treatments for infectious diseases and the prevention of cardiovascular disease continues to improve, and the average life expectancy increases, cancer is likely to become the most common fatal disease in these countries. Therefore, successfully treating cancer requires that all the malignant cells be removed or destroyed without killing the patient. An ideal way to achieve this would be to induce an immune response against the tumour that would discriminate between the cells of the tumour and their normal cellular counterparts. However, immunological approaches to the treatment of cancer have been attempted for over a century with unsustainable results.

Accordingly, current methods of treating cancer continue to follow the long used protocol of surgical excision (if possible) followed by radiotherapy and/or chemotherapy, if necessary. The success rate of this rather crude form of treatment is extremely variable but generally decreases significantly as the tumour becomes more advanced and metastasises. Further, these treatments are associated with severe side effects including disfigurement and scarring from surgery (e.g. mastectomy or limb amputation), severe nausea and vomiting from chemotherapy, and most significantly, the damage to normal tissues such as the hair follicles, gut and bone marrow which is induced as a result of the relatively non-specific targeting mechanism of the toxic drugs which form part of most cancer treatments and is a major limiting factor for dosage Still further, common chemotherapy drugs do not significantly penetrate into tissue further than about 70 microns from the blood supply (Primeau et al. *Clin. Canc. Res.* 2005, 11:8782-8788; Minchinton et al. *Nat. Rev. Cancer* 2006, 6:583-592). The rapid growth and poor vascular development of most solid tumours puts many tumour cells well beyond the capacity of the drugs to penetrate the tissue. Critically, many cells experience sub-lethal doses, allowing them to survive and to develop drug resistance.

Solid tumours cause the greatest number of deaths from cancer and mainly comprise tumours of the linings of the bronchial tree and the alimentary tract that are known as carcinomas. In the year 2000 in Australia, cancer accounted for 30% of male deaths and 25% of female deaths (Cancer in Australia 2000, 2003) and it accounted for 24% of male and 22% of female deaths in the US in year 2001 (Arias et al. 2003, *National Vital Statistics Reports* 52:111-115). Solid tumours are not usually curable once they have spread or 'metastasised' throughout the body. The prognosis of metastatic solid tumours has improved only marginally in the last 50 years. The best chance for the cure of a solid tumour remains in the use of local treatments such as surgery and/or radiotherapy when the solid tumour is localised to its originating lining and has not spread either to the lymph nodes that drain the tumour or elsewhere. Nonetheless, even at this early stage, and particularly if the tumour has spread to the draining lymph nodes, microscopic deposits of cancer known as micrometastases may have already spread throughout the body and will subsequently lead to the death of the patient. In this sense, cancer is a systemic disease that requires systemically administered treatments. Of the patients who receive surgery and/or radiotherapy as definitive local treatment for their primary tumour and who have micrometastases, a minor proportion may be cured or at least achieve a durable remission from cancer by the addition of adjuvant systemic treatments such as cytotoxic chemotherapy or hormones.

Conventionally, solid cancer has been treated locally with surgery and/or radiotherapy, and during its metastatic stage with systemically administered cytotoxic drugs, which often interfere with the cell cycle of both normal and malignant cells. The relative selectivity of this approach for the treatment of malignant tissues is based to some extent on the more rapid recovery of normal tissues from cytotoxic drug damage. More recently, the targeted therapy of cancer has aimed to improve the therapeutic ratio of cancer treatment by enhancing its specificity and/or precision of delivery to malignant tissues while minimising adverse consequences to normal non-malignant tissues. Two of the major classes of targeted therapy are (i) the small molecule inhibitors such as the tyrosine kinase inhibitors imatinib mesylate (Glivec®), gefitinib (Iressa®) and erlotinib (Tarceva®), and (ii) the monoclonal antibodies (mAb) such as rituximab (Mabthera®) and trastuzumab (Herceptin®).

In parallel to the development of targeted therapies, combining at least two conventional anti-cancer treatments such as chemotherapy and radiotherapy in novel ways has been another approach to the development of cancer therapeutics. By exploiting synergistic interactions between the different modalities of treatment, combined modality treatment seeks to improve treatment efficacy so that the therapeutic ratio for the combined treatment is superior to that for each of the individual treatments.

Combined modality treatment using external beam radiation and radiosensitising chemotherapeutic drugs such as 5-fluorouracil and cisplatin (chemoradiotherapy) has improved survival in a number of solid tumours such as those of head and neck, lung, oesophagus, stomach, pancreas and rectum because of both improved local tumour control and reduced rates of distant failure (TS Lawrence. *Oncology (Huntington)* 17:23-28, 2003). Although radiosensitising drugs increase tumour response, they also increase toxicity to adjacent normal tissues, which is especially true of the potent new generation radiosensitisers, gemcitabine and docetaxel. However, decreasing the radiation volume allows cytotoxic doses of gemcitabine to be better tolerated clinically (Lawrence 2003, supra). Chemoradiotherapy may overcome mutually reinforcing resistance mechanisms, which may only manifest in vivo.

Radioimmunotherapy (RIT) is a systemic treatment that takes advantage of the specificity and avidity of the antigen-antibody interaction to deliver lethal doses of radiation to cells that bear the target antigen. Radio-isotopes that emit β-particles (e.g. $^{131}$Iodine, $^{90}$Yttrium, $^{188}$Rhenium, and $^{67}$Copper) are usually used to label monoclonal antibodies (mAb) for therapeutic applications. The energy from □-radiation is released at relatively low intensity over distances measured in millimeters (Waldmann, *Science* 252:1657-1662, 1991; Bender et al., *Cancer Research* 52:121-126, 1992; O'Donoghue et al. *Journal of Nuclear Medicine* 36:1902-1909, 1995; Griffiths et al. *International Journal of Cancer* 81:985-992, 1999). Thus, high-energy □-emitters such as $^{90}$Yttrium are useful for the treatment of larger and heterogeneous solid tumours (Liu et al. *Bioconjugate Chemistry* 12:7-34, 2001). Research interest in radioimmunotherapy has been reawakened because in spite of the low radiation doses delivered, significant and unexpected biological effects of RIT upon surrounding host cells have been observed (Xue et al. *Proceedings of the National Academy of Sciences of the United States of America* 99:13765-13770, 2002). Furthermore, the lower but biologically effective dose of radiation delivered by RIT had greater cytocidal effects than a larger dose of radiation conveyed as external beam radiotherapy (Dadachova et al., *PNAS* 101:14865-14870, 2004). Nonetheless, the efficiency of RIT as a treatment for solid tumours may be hampered by the low penetration of antibody through the tissue barriers that surround the target antigen in the tumour, which will consequently extend circulatory half life of the antibody (Britz-Cunningham et al. *Journal of Nuclear Medicine* 44:1945-1961, 2003). Furthermore, RIT is often impeded by the heterogeneity of the target antigen's expression within the tumour. Thus, although RIT affords molecular targeting of tumour cells, the major limitation of RIT remains the toxicity that may result from large doses of radiation that are delivered systemically in order to achieve sufficient targeting (Britz-Cunningham et al. 2003, supra; Christiansen et al. *Molecular Cancer Therapy* 3:1493-1501, 2004). Altogether, a useful therapeutic index using RIT has proven difficult to achieve clinically (Sellers et al. *Journal of Clinical Investigation* 104:1655-1661, 1999).

Tumour associated antigens, which would allow differential targeting of tumours, while sparing normal cells, have also been the focus of cancer research. Although abundant ubiquitous antigens may provide a more concentrated and accessible target for RIT, studies adopting this have been extremely limited.

The development of nanoparticle technology was also hailed as an exciting new frontier in terms of the development of new and effective cancer treatments. However, although previous attempts at using particulate material, such as nanoparticles, to target tumours for either diagnostic or therapeutic purposes have been extensive, in the context of therapeutics there has, disappointingly, been minimal success. With diagnostics, relatively shallow penetration of the particles into the tumour has been sufficient to achieve the objective of visualising the tumour. However, in terms of the delivery of a therapeutic agent, such shallow penetration has not been sufficient to effectively deliver the agent throughout the tumour, in particular to the interior of the tumour, as is required if total tumour destruction is to be achieved. In relation to therapeutics, specifically, conjugation of particles to a wide variety of different materials has so far failed to live up to the promise of achieving effective tumour penetration, this being an essential prerequisite for a therapeutic to have any chance of effectiveness.

Significant effort has also been made to take advantage of the enhanced permeability and retention (EPR) effect of tumours as a means to develop an effective therapeutic. Without limiting the present invention to any one theory or mode of action, this is a well described phenomenon based on the notion that certain sizes of molecules, typically liposomes or macromolecular drugs, tend to preferentially accumulate in tumour tissue. The general explanation for this phenomenon is that, in order for tumour cells to grow quickly, they must stimulate the production of blood vessels. VEGF and other growth factors are involved in cancer angiogenesis. Tumour cell aggregates of sizes as small as 150-200 µm become dependent on blood supply carried by neovasculature for their nutritional and oxygen supply. These newly formed tumour vessels are usually abnormal in form and architecture. They comprise poorly-aligned defective endothelial cells with wide fenestrations, lacking a smooth muscle layer, or innervation with a wider lumen, and impaired functional receptors for angiotensin II. Furthermore, tumour tissues usually lack effective lymphatic drainage. All these factors will lead to abnormal molecular and fluid transport dynamics, especially for macromolecular drugs. Accordingly, it has been thought that one way to achieve selective drug targeting to solid tumours is to exploit these abnormalities of tumour vasculature in terms of active and selective delivery of anticancer drugs to tumour tissues, notably defining the EPR effect of macromolecular drugs in solid tumours. Due to their large molecular size, nanosized macromolecular anticancer drugs administered intravenously escape renal clearance. Often they cannot penetrate the tight endothelial junctions of normal blood vessels, but they can extravasate in tumour vasculature and become trapped in the tumour vicinity. Nevertheless, the EPR effect has not been efficiently or successfully harnessed.

Various nanoparticles have been designed which are directed to achieving efficient cellular endocytosis. However, even if this is achievable, the issue of tissue penetration is still a separate one which, to date, has not been successfully overcome. The general notion of the use of a nanoparticle as a vector for delivery of a drug is widely discussed in the literature but, in the absence of achieving deep tumour penetration, is of limited value.

Even where effective tumour distribution of a drug is achieved (by whatever means) a further problem has been the fact that neoplastic cells within solid tumours can exhibit a slowed metabolism. This means that even if a cytotoxic drug penetrates to these cells, if it is not effectively metabolised it will have a limited impact on the viability of the tumour.

Accordingly, there is an urgent and ongoing need to develop improved systemic therapies for solid cancers, in particular metastatic cancers.

In work leading up to the present invention it has been determined that particulate material which is maintained in a dispersed state by a stabiliser is able to achieve deeper penetration into solid tumour models than has previously been achievable using nanoparticle technology. This has enabled the development of an effective means for treating solid tumours, both primary and metastatic, based on the co-administration of a cellular toxin with the particulate material. By either sequentially or simultaneously delivering this toxin, deeper penetration and therefore more extensive cellular exposure to the toxin is achieved. By virtue of the less effective reticuloendothelial clearance which is associated with tumours, a form of targeted treatment is effectively achieved. Still further, it has been observed that the toxin uptake by tumours penetrated by the particles of the present invention is effective, suggesting upregulation of tumour cell metabolism. Accordingly, the method of the present invention provides a means for achieving a more effective localised delivery and uptake of a cellular toxin to a tumour and its metastases in a manner which is characterised by significantly improved outcomes and/or reduced side effects relative to those which would normally be expected in the context of conventional treatment of an equivalent type of tumour. This is an extremely significant development since current protocols directed to treating metastatic disease are based on the non-targeted systemic delivery of chemotherapeutic agents.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of treating a solid tumour in a subject, said method comprising co-administering to said subject an effective amount of particulate material and a cellular toxin for a time and under conditions sufficient to facilitate distribution of said particulate material and toxin to said tumour wherein:

(i) said particulate material is administered in the form of a dispersion in a liquid carrier, the particulate material being maintained in the dispersed state by a stabiliser; and
(ii) said stabiliser comprising an anchoring portion that (a) anchors the stabiliser to the particulate material, and (b) is different from the remainder of the stabiliser;
and wherein said particulate material and toxin penetrate said solid tumour.

For convenience, said particulate material that is maintained in the dispersed state by a stabiliser may herein be referred to as "stabilised particulate material".

In one embodiment, the stabiliser is a steric stabiliser, said steric stabiliser comprising a steric stabilising polymeric segment and an anchoring portion, wherein the steric stabilising polymeric segment is different from the anchoring portion, and wherein the anchoring portion anchors the stabiliser to the particulate material The method may therefore comprise co-administering to said subject an effective amount of particulate material and a cellular toxin for a time and under conditions sufficient to facilitate distribution of said particulate material and toxin to said tumour wherein:

(i) said particulate material is administered in the form of a dispersion in a liquid carrier, the particulate material being maintained in the dispersed state by a steric stabiliser; and
(ii) said steric stabiliser comprising a steric stabilising polymeric segment and an anchoring portion, wherein the steric stabilising polymeric segment is different from the anchoring portion, and wherein the anchoring portion anchors the stabiliser to the particulate material;
and wherein said particulate material and toxin penetrate said solid tumour.

In another embodiment, said solid tumour is benign.

In a further embodiment said tumour is malignant.

In yet another embodiment, said anchoring portion is an anchoring polymeric segment. In that case, said stabiliser comprises an anchoring polymeric segment, or said steric stabiliser comprises a steric stabilising polymeric segment and an anchoring polymeric segment.

In a further embodiment, said stabiliser comprises an anchoring portion, one or both of the stabiliser or anchoring portion being derived from one or more ethylenically unsaturated monomers that have been polymerised by a living polymerisation technique, wherein the anchoring portion is different from the remainder of the stabiliser, and wherein the anchoring portion anchors the stabiliser to the particulate material. According to this embodiment, the anchoring portion may be referred to as an anchoring polymeric segment.

In another embodiment, said steric stabiliser comprises a steric stabilising polymeric segment and an anchoring polymeric segment, one or both of which are derived from one or more ethylenically unsaturated monomers that have been polymerised by a living polymerisation technique, wherein the steric stabilising polymeric segment is different from the anchoring polymeric segment, and wherein the anchoring polymeric segment anchors the stabiliser to the particulate material.

In another aspect the present invention provides a method of treating a malignant solid tumour in a subject, said method comprising co-administering to said subject an effective amount of particulate material and a cellular toxin for a time and under conditions sufficient to facilitate distribution of said particulate material and toxin to said tumour wherein:

(i) said particulate material is administered in the form of a dispersion in a liquid carrier, the particulate material being maintained in the dispersed state by a stabiliser; and
(ii) said stabiliser comprising an anchoring portion that (a) anchors the stabiliser to the particulate material, and (b) is different from the remainder of the stabiliser;

and wherein said particulate material and toxin penetrate said solid tumour.

Where the stabiliser is a steric stabiliser comprising a steric stabilising polymeric segment and an anchoring portion, wherein the steric stabilising polymeric segment is different from the anchoring portion, the method of treating a malignant solid tumour in a subject comprises co-administering to said subject an effective amount of particulate material and a cellular toxin for a time and under conditions sufficient to facilitate distribution of said particulate material and toxin to said tumour wherein:
(i) said particulate material is administered in the form of a dispersion in a liquid carrier, the particulate material being maintained in the dispersed state by a steric stabiliser; and
(ii) said steric stabiliser comprising a steric stabilising polymeric segment and an anchoring portion, wherein the steric stabilising polymeric segment is different from the anchoring portion, and wherein the anchoring portion anchors the stabiliser to the particulate material;

and wherein said particulate material and toxin penetrate said solid tumour.

In one embodiment, said malignant solid tumour is a metastatic malignant solid tumour. Reference to "metastatic" should be understood as a reference to a tumour which either has undergone metastatisation or may have undergone metastatisation.

In another embodiment, said malignant solid tumour is a central nervous system tumour, retinoblastoma, neuroblastoma, paediatric tumour, head and neck cancer such as squamous cell cancer, breast and prostate cancer, lung cancer, kidney cancers, such as renal cell adenocarcinoma, oesophagogastric cancer, hepatocellular carcinoma, pancreaticobiliary neoplasia, such as adenocarcinomas and islet cell tumours, colorectal cancer, cervical cancer, anal cancer, uterine or other reproductive tract cancer, urinary tract cancer, such as of the ureter or bladder, germ cell tumour such as a testicular germ cell tumour or ovarian germ cell tumour, ovarian cancer, such as an ovarian epithelial cancer, carcinoma of unknown primary, human immunodeficiency associated malignancy, such as Kaposi's sarcoma, lymphoma, leukemia, malignant melanoma, sarcoma, endocrine tumour, such as of the thyroid gland, mesothelioma or other pleural or peritoneal tumour, neuroendocrine tumour or carcinoid tumour.

By "co-administration" is meant that the stabilised particulate material and the cellular toxin are administered as separate entities in their own right. In other words, at the time of administration the stabilised particulate material and the cellular toxin are not covalently or chemically coupled to each other.

Co-administration of the stabilised particulate material and the cellular toxin in the context of the present invention includes both simultaneous and sequential administration. Simultaneous administration includes where the stabilised particulate material and the cellular toxin are present in the same formulation or in two different formulations, but each are nevertheless administered at substantially the same time. In the case of sequential administration, a multi-step procedure is used where the stabilised particulate material is administered in one step and the cellular toxin is administered at a different time in a separate step. The cellular toxin may be administered prior to administration of the stabilised particulate material. The time difference between administration of the stabilised particulate material and the cellular toxin in sequential administration can vary, but will generally range from about 1 minute to about 4 days, for example from about 1 minute to about 2 hours, or from about 1 minute to about 24 hours, or from about 1 minute to about 12 hours, or from about 1 minute to about 6 hours, or from about 1 minute to about 3 hours, or from about 1 minute to about 1 hour.

In a sequential administration, the stabilised particulate material will generally be administered prior to the cellular toxin.

The particulate material and the cellular toxin may be administered by the same or different routes.

Without limiting the present invention to any one theory or mode of action, once the particulate material has penetrated the tumour, effective penetration of the administered cellular toxin is also achieved.

It will be appreciated that it is well within the skills of the person in the art, and in light of the teaching provided herein, to select and design an administration protocol for the elements herein described.

In a further aspect there is provided a method of treating a solid tumour in a subject, said method comprising:
(a) administering to said subject an effective amount of particulate material and for a time and under conditions sufficient to facilitate distribution of said particulate material to said tumour wherein:
 (i) said particulate material is administered in the form of a dispersion in a liquid carrier, the particulate material being maintained in the dispersed state by a stabiliser; and
 (ii) said stabiliser comprising an anchoring portion that (a) anchors the stabiliser to the particulate material, and (b) is different from the remainder of the stabiliser; and
(b) administering to said subject an effective amount of a cellular toxin subsequently to administration of said particulate material;

and wherein said particulate material and toxin penetrate said solid tumour.

Where the stabiliser is a steric stabiliser comprising a steric stabilising polymeric segment and an anchoring portion, wherein the steric stabilising polymeric segment is different from the anchoring portion, the method of treating a solid tumour in a subject comprises:
(a) administering to said subject an effective amount of particulate material and for a time and under conditions sufficient to facilitate distribution of said particulate material to said tumour wherein:
 (i) said particulate material is administered in the form of a dispersion in a liquid carrier, the particulate material being maintained in the dispersed state by a steric stabiliser; and
 (ii) said steric stabiliser comprising a steric stabilising polymeric segment and an anchoring portion, wherein the steric stabilising polymeric segment is different from the anchoring portion, and wherein the anchoring portion anchors the stabiliser to the particulate material; and
(b) administering to said subject an effective amount of a cellular toxin subsequently to administration of said particulate material;

and wherein said particulate material and toxin penetrate said solid tumour.

In yet another aspect there is provided a method of treating a solid tumour in a subject, said method comprising co-administering to said subject an effective amount of particulate material and a cytostatic or cytocidal agent for a time and under conditions sufficient to facilitate distribution of said particulate material and toxin to said tumour, wherein:
(i) said particulate material is administered in the form of a dispersion in a liquid carrier, the particulate material being maintained in the dispersed state by a stabiliser; and
(ii) said stabiliser comprising an anchoring portion that (a) anchors the stabiliser to the particulate material, and (b) is different from the remainder of the stabiliser;
and wherein said particulate material and said cytostatic or cytocidal agent penetrate said solid tumour.

Where the stabiliser is a steric stabiliser comprising a steric stabilising polymeric segment and an anchoring portion, wherein the steric stabilising polymeric segment is different from the anchoring portion, the method of treating a solid tumour in a subject comprises co-administering to said subject an effective amount of particulate material and a cytostatic or cytocidal agent for a time and under conditions sufficient to facilitate distribution of said particulate material and toxin to said tumour, wherein:
(i) said particulate material is administered in the form of a dispersion in a liquid carrier, the particulate material being maintained in the dispersed state by a steric stabiliser; and
(ii) said steric stabiliser comprising a steric stabilising polymeric segment and an anchoring portion, wherein the steric stabilising polymeric segment is different from the anchoring portion, and wherein the anchoring portion anchors the stabiliser to the particulate material;
and wherein said particulate material and said cytostatic or cytocidal agent penetrate said solid tumour.

Examples of cytotoxic agents include, but are not limited to, Actinomycin D, Adriamycin, Arsenic Trioxide, Asparaginase, Bleomycin, Busulfan, Camptosar, Carboplatinum, Carmustine, Chlorambucil, Cisplatin, Corticosteroids, Colicheamicin, Cyclophosphamide, Daunorubicin, Docetaxel, Doxorubicin, Epirubicin, Etoposide, Fludarabine, Fluorouracil, Gemcitabina, Gemcitabine, Gemzar, Hydroxyurea, Idarubicin, Ifosfamide, Irinotecan, Lomustine, Melphalan, Mercaptomurine, Methotrexate, Mitomycin, Mitoxantrone, Oxaliplatin, Paclitaxel, Platinol, Platinex, Procarbizine, Raltitrexeel, Rixin, Steroids, Streptozocin, Taxol, Taxotere, Thioguanine, Thiotepa, Tomudex, Topotecan, Treosulfan, Trihydrate, Vinblastine, Vincristine, Vindesine, Vinorelbina, Vinorelbine, duanomycin, dactinomysin, esorubisin, mafosfamide, cytosine arabinoside, bis-chloroethylnitrosurea, Mitomycin C, mithramycin, prednisone, hydroxyprogesterone, testosterone, tamoxifen, dacarbazine, hexamethylmelamine, pentamethylmelamine, amsacrine, chlorambudil, methylcyclohexylnitrosurea, nitrogen mustards, Cyclophosphamide, 6-mercaptopurine, 6-thioguanine, cytarabine, 5-azacytidine, deoxyco-formycin, 4-hydroxyperoxycyclophosphoramide, 5-fluorouracil (5-FU), 5-fluorodeoxyuridine (5-FUdR), colchicine, trimetrexate, teni-poside, diethylstilbestrol.

Reference to "cellular toxin" should also be understood to extend to any other molecule which is perhaps not traditionally regarded as a cytotoxic agent but nevertheless falls within the scope of the present definition on the basis that it induces cellular damage, for example DNA damage, such as nucleophosmin or agents which induce cellular damage as part of a synergistic process with another agent. Examples include catalytic antibodies, prodrugs, CHK1/2 inhibitor (such as CBP-501 or AZD7762), histone deacetylase inhibitor (such as vorinostat), tumour necrosis factor related apoptosis inducing ligand or BH3 mimetic (such as ABT737), small molecule inhibitors such as the tyrosine kinase inhibitors imatinib mesylate (Glivec®), gefitinib (Iressa®) and erlotinib (Tarceva®), and the monoclonal antibodies (mAb) such as rituximab (Mabthera®) and trastuzumab (Herceptin®).

In yet another embodiment, combination treatments may include, for example, gemcitabine together with a CHK1/2 inhibitor or irinotecam together with a CHK1/2 inhibitor.

The particulate material and/or the stabiliser may be coupled to a ligand to effect more specific targeting to a tumour. This will not necessarily be applicable in every situation but, to the extent that an appropriate target molecule exists for a given tumour, this may provide additional useful specificity.

According to such an embodiment, there is provided a method of treating a solid tumour in a subject, said method comprising co-administering to said subject an effective amount of particulate material and a cellular toxin for a time and under conditions sufficient to facilitate distribution of said particulate material and toxin to said tumour, wherein:
(i) said particulate material is administered in the form of a dispersion in a liquid carrier, the particulate material being maintained in the dispersed state by a stabiliser; and
(ii) said stabiliser comprising an anchoring portion that (a) anchors the stabiliser to the particulate material, and (b) is different from the remainder of the stabiliser;
wherein the particulate material and/or the stabiliser is linked, bound or otherwise associated with a ligand directed to a tumour molecule and wherein said particulate material and toxin penetrate said solid tumour.

Where the stabiliser is a steric stabiliser comprising a steric stabilising polymeric segment and an anchoring portion, wherein the steric stabilising polymeric segment is different from the anchoring portion, there is also provided a method of treating a solid tumour in a subject, said method comprising co-administering to said subject an effective amount of particulate material and a cellular toxin for a time and under conditions sufficient to facilitate distribution of said particulate material and toxin to said tumour, wherein:
(i) said particulate material is administered in the form of a dispersion in a liquid carrier, the particulate material being maintained in the dispersed state by a steric stabiliser; and
(ii) said steric stabiliser comprising a steric stabilising polymeric segment and an anchoring portion, wherein the steric stabilising polymeric segment is different from the anchoring portion, and wherein the anchoring portion anchors the stabiliser to the particulate material;
wherein the particulate material and/or the steric stabiliser is linked, bound or otherwise associated with a ligand directed to a tumour molecule and wherein said particulate material and toxin penetrate said solid tumour.

In yet another aspect, there is provided the use of particulate material and a cellular toxin in the manufacture of a medicament for the treatment of a solid tumour wherein:
(i) said particulate material is in the form of a dispersion in a liquid carrier, the particulate material being maintained in the dispersed state by a stabiliser; and
(ii) said stabiliser comprising an anchoring portion that (a) anchors the stabiliser to the particulate material, and (b) is different from the remainder of the stabiliser;
and wherein said particulate material and toxin penetrate said solid tumour.

Where the stabiliser is a steric stabiliser comprising a steric stabilising polymeric segment and an anchoring portion, wherein the steric stabilising polymeric segment is different from the anchoring portion, there is provided the use of particulate material and a cellular toxin in the manufacture of a medicament for the treatment of a solid tumour wherein:

(i) said particulate material is in the form of a dispersion in a liquid carrier, the particulate material being maintained in the dispersed state by a steric stabiliser; and (ii) said steric stabiliser comprising a steric stabilising polymeric segment and an anchoring portion, wherein the steric stabilising polymeric segment is different from the anchoring portion, and wherein the anchoring portion anchors the stabiliser to the particulate material;

and wherein said particulate material and toxin penetrate said solid tumour.

Further aspects and/or embodiments of the invention are discussed in more detail below.

DETAILED DESCRIPTION OF THE INVENTION

Figure 1:
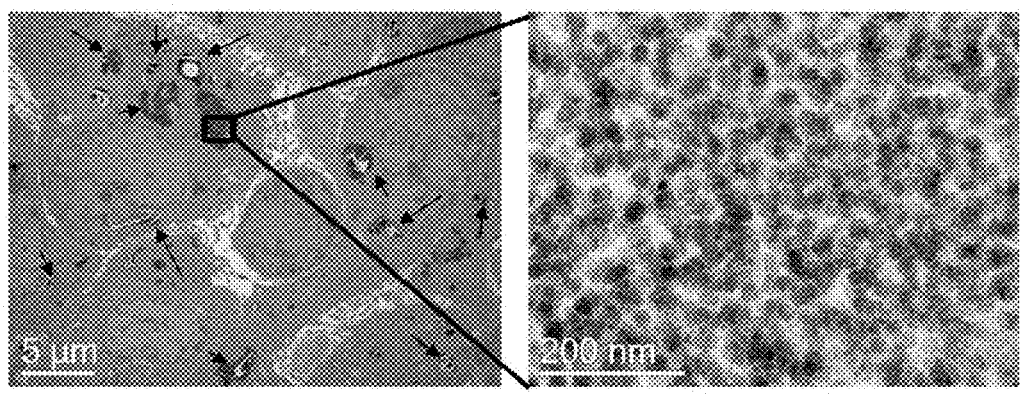
FIG. 1: Sterically stabilised nanoparticles are able to penetrate into spheroids. TEM images of the accumulation of NP2 particles in spheroids. Arrows indicate areas of nanoparticle accumulation. Boxed region is enlarged and shown in the image on right. Scale bars as indicated.

The present invention is predicated, in part, on the determination that particulate material which is maintained in a dispersed state by a certain type of stabiliser can achieve a deeper and more effective penetration into a solid tumour than has been previously achievable using particle technology. The nature of the penetration effected by these particulate materials has achieved both a significantly wider cellular distribution, within the tumour, of the toxin co-administered with the particulate material and, further, more effective induction of cellular toxicity. Since reticuloendothelial clearance from the sites of tumours is significantly less effective than in normal tissue, the method of the invention enables not only more effective tumour penetration but, further, the delivery of lower concentrations of cellular toxins which are enabled to localise, and thereby concentrate, at tumour sites. This reduces the side effects which would be apparent in the context of conventional systemic chemotherapy where such treatment would be delivered at the highest dose which can be tolerated by the patient and, further, often in the context of multiple repeated rounds over a period of months. This development now provides a realistic means of moving away from the treatment of primary tumours and metastatic disease via the non-targeted, systemic delivery of chemotherapy.

Reference to a "solid tumour" herein should be understood as a reference to an encapsulated or unencapsulated mass or other form of growth or cellular aggregate which comprises neoplastic cells. Reference to a "neoplastic cell" should be understood as a reference to a cell exhibiting abnormal growth. The term "growth" should be understood in its broadest sense and includes reference to proliferation. The phrase "abnormal growth" in this context is intended as a reference to cell growth which, relative to normal cell growth, exhibits one or more of an increase in the rate of cell division, an increase in the number of cell divisions, a decrease in the length of the period of cell division, an increase in the frequency of periods of cell division or uncontrolled proliferation and evasion of apoptosis. Without limiting the present invention in any way, the common medical meaning of the term "neoplasia" refers to new cell growth that results as a loss of responsiveness to normal growth controls, e.g. to neoplastic cell growth. Neoplasias include "tumours" which may be either benign, pre-malignant or malignant. The term "neoplasm" should be understood as a reference to a lesion, tumour or other encapsulated or unencapsulated mass or other form of growth or cellular aggregate which comprises neoplastic cells.

The term "neoplasm", in the context of the present invention should be understood to include reference to all types of cancerous growths or oncogenic processes, metastatic tissues or malignantly transformed cells, tissues or organs irrespective of histopathologic type or state of invasiveness.

The term "carcinoma" is recognised by those skilled in the art and refers to malignancies of epithelial or endocrine tissues including respiratory system carcinomas, gastrointestinal system carcinomas, genitourinary system carcinomas, testicular carcinomas, breast carcinomas, prostate carcinomas, endocrine system carcinomas and melanomas. Exemplary carcinomas include those forming from tissue of the breast. The term also includes carcinosarcomas, e.g. which include malignant tumours composed of carcinomatous and sarcomatous tissues. An "adenocarcinoma" refers to a carcinoma derived from glandular tissue or in which the tumour cells form recognisable glandular structures.

The neoplastic cells comprising the neoplasm may be any cell type, derived from any tissue, such as an epithelial or non-epithelial cell. Examples of neoplasms and neoplastic cells encompassed by the present invention include, but are not limited to central nervous system tumours, retinoblastoma, neuroblastoma and other paediatric tumours, head and neck cancers (e.g. squamous cell cancers), breast and prostate cancers, lung cancer (both small and non-small cell lung cancer), kidney cancers (e.g. renal cell adenocarcinoma), oesophagogastric cancers, hepatocellular carcinoma, pancreaticobiliary neoplasias (e.g. adenocarcinomas and islet cell tumours), colorectal cancer, cervical and anal cancers, uterine and other reproductive tract cancers, urinary tract cancers (e.g. of ureter and bladder), germ cell tumours (e.g. testicular germ cell tumours or ovarian germ cell tumours), ovarian cancer (e.g. ovarian epithelial cancers), carcinomas of unknown primary, human immunodeficiency associated malignancies (e.g. Kaposi's sarcoma), lymphomas, malignant melanomas, sarcomas, endocrine tumours (e.g. of thyroid gland), mesothelioma and other pleural or peritoneal tumours, neuroendocrine tumours and carcinoid tumours.

Preferably, the present invention is directed to the treatment of a malignant neoplastic condition and even more preferably a metastatic neoplastic condition. It would be appreciated that although the method of the invention can be applied to the treatment of any neoplasm, it is particularly useful in terms of the treatment of metastasised neoplasms. Without limiting the present invention to any one theory or mode of action, non-metastasised primary tumours are treatable either by the method of the invention or by conventional treatment regimes such as surgical excision of the tumour or radiotherapy. However, tumours which have metastasised are not curable by either of these conventional treatment regimes due to the often extensive spread and growth of metastatic nodules. Accordingly, such conditions are currently only treatable by the administration of systemic chemotherapy, this treatment regime often causing severe side effects for limited curative potential. Still further, even in the context of primary tumours which appear not to have metastasised, chemotherapy is still often recommended following surgery and radiation in case metastatic spread has occurred but is not yet detectable. This is a particularly common practice in the context of cancers which are traditionally regarded as aggressive, such as breast and colon cancers. The method of the present invention now provides an alternative to the application of aggressive systemic chemotherapy treatment regimes. Since the systemic administration of the cytotoxic agent of the present invention is able to be delivered in a more localised fashion to tumours and is more effectively metabolised by the neoplastic cells, the occurrence of side effects can be minimised via the administration of lower doses of the cellular toxin.

In one embodiment, said solid tumour is benign.

In another embodiment, said solid tumour is malignant.

Preferably, said malignant solid tumour is a metastatic malignant solid tumour. Reference to "metastatic" should be understood as a reference to a tumour which either has undergone metastatisation or may have undergone metastatisation.

In one embodiment, said malignant solid tumour is a central nervous system tumour, retinoblastoma, neuroblastoma, paediatric tumour, head and neck cancer such as squamous cell cancer, breast and prostate cancer, lung cancer, kidney cancers, such as renal cell adenocarcinoma, oesophagogastric cancer, hepatocellular carcinoma, pancreaticobiliary neoplasia, such as adenocarcinomas and islet cell tumours, colorectal cancer, cervical cancer, anal cancer, uterine or other reproductive tract cancer, urinary tract cancer, such as of the ureter or bladder, germ cell tumour such as a testicular germ cell tumour or ovarian germ cell tumour, ovarian cancer, such as an ovarian epithelial cancer, carcinoma of unknown primary, human immunodeficiency associated malignancy, such as Kaposi's sarcoma, lymphoma, leukemia, malignant melanoma, sarcoma, endocrine tumour, such as of the thyroid gland, mesothelioma or other pleural or peritoneal tumour, neuroendocrine tumour or carcinoid tumour.

As detailed hereinbefore, the method of the present invention is based on the co-administration of a cellular toxin with stabilised particulate material. Previous attempts at using particulate material, such as nanoparticles, to target tumours for either diagnostic or therapeutic purposes have been extensive but, in the context of therapeutics, of minimal success. With diagnostics, relatively shallow penetration of the particles into the tumour has been sufficient to achieve the objective of visualising the tumour. However, in terms of the delivery of a therapeutic agent, such shallow penetration has not been sufficient to effectively deliver the agent throughout the tumour, in particular to the interior of the tumour. In relation to therapeutics, specifically, conjugation of particles to a wide variety of different materials has so far failed to live up to the promise of achieving effective tumour penetration, this being an essential prerequisite for a therapeutic to have any chance of effectiveness.

Significant effort has also been made to take advantage of the enhanced permeability and retention (EPR) effect of tumours as a means to develop an effective therapeutic. Without limiting the present invention to any one theory or mode of action, this is a well described phenomenon based on the notion that certain sizes of molecules, typically liposomes or macromolecular drugs, tend to preferentially accumulate in tumour tissue. The general explanation for this phenomenon is that, in order for tumour cells to grow quickly, they must stimulate the production of blood vessels. VEGF and other growth factors are involved in cancer angiogenesis. Tumour cell aggregates of sizes as small as 150-200 µm become dependent on blood supply carried by neovasculature for their nutritional and oxygen supply. These newly formed tumour vessels are usually abnormal in form and architecture. They comprise poorly-aligned defective endothelial cells with wide fenestrations, lacking a smooth muscle layer, or innervation with a wider lumen, and impaired functional receptors for angiotensin II. Furthermore, tumour tissues usually lack effective lymphatic drainage. All these factors will lead to abnormal molecular and fluid transport dynamics, especially for macromolecular drugs. Accordingly, it has been thought that one way to achieve selective drug targeting to solid tumours is to exploit these abnormalities of tumour vasculature in terms of active and selective delivery of anticancer drugs to tumour tissues, notably defining the EPR effect of macromolecular drugs in solid tumours. Due to their large molecular size, nanosized macromolecular anticancer drugs administered intravenously escape renal clearance. Often they cannot penetrate the tight endothelial junctions of normal blood vessels, but they can extravasate in tumour vasculature and become trapped in the tumour vicinity. Nevertheless, the EPR effect has not been efficiently or successfully harnessed.

Various nanoparticles have been designed which are directed to achieving efficient cellular endocytosis. However, even if this is achievable, the issue of tissue penetration is still a separate one which, to date, has not been successfully overcome. The general notion of the use of a nanoparticle as a vector for delivery of a drug is widely discussed in the literature but, in the absence of achieving deep tumour penetration, is of limited value.

Even where effective tumour distribution of a drug is achieved (by whatever means) a further problem has been the fact that neoplastic cells within solid tumours can exhibit a slowed metabolism. This means that even if a cytotoxic drug penetrates to these cells, if it is not effectively metabolised it will have a limited impact on the viability of the tumour.

Without limiting the present invention to any one theory or mode of action, the method of the present invention is thought to achieve its therapeutic outcomes by both deep penetration of the tumour by the particulate material, which thereby enables simultaneous or sequential penetration by a cellular toxin, and enabling effective metabolism of the toxin so as to achieve cell death. Still without limiting the present invention in any way, it is thought that this may be due to the particulate material defined herein, by virtue of their design, acting to upregulate cellular metabolism which has become slowed or dormant.

The cellular toxin of the present invention should be understood as any proteinaceous or non-proteinaceous molecule or group of molecules which will either retard cell growth or induce cell death, for example either by directly killing the cell or else delivering a signal which induces apoptosis. That is, the agent may be either cytostatic or cytocidal. It would be appreciated by the person of skill in the art that the method of the present invention can be designed to deliver one cellular toxin or multiple cellular toxins (i.e. a "cocktail" of drugs). The decision in relation to how best to proceed can be made by the person of skill in the art as a matter of routine procedure. For example, depending on the tumour type, certain specific drugs or combinations of drugs are regarded as particularly desirable to use. It would be appreciated that the body of knowledge in relation to the characteristics and use of cytotoxic agents is extensive and the person of skill in the art could design an administration protocol to meet the parameters of the present invention as a matter of routine procedure.

Reference to "cellular toxin" herein should therefore be understood as a reference to any agent which acts to damage or destroy cells. Without limiting the present invention to any one theory or mode of action, many such agents function via the induction of apoptotic processes. However, this is not the only mechanism by which such agents function and it is conceivable that the subject damage or cell death may be induced by some other mechanism. Examples of cytotoxic agents include, but are not limited to, Actinomycin D, Adriamycin, Arsenic Trioxide, Asparaginase, Bleomycin, Busulfan, Camptosar, Carboplatinum, Carmustine, Chlorambucil, Cisplatin, Corticosteroids, Colicheamicin, Cyclophosphamide, Daunorubicin, Docetaxel, Doxorubicin, Epirubicin, Etoposide, Fludarabine, Fluorouracil, Gemcitabina, Gemcitabine, Gemzar, Hydroxyurea, Idarubicin, Ifosfamide, Irinotecan, Lomustine, Melphalan, Mercaptomurine, Methotrexate, Mitomycin, Mitoxantrone, Oxaliplatin, Paclitaxel, Platinol, Platinex, Procarbizine, Raltitrexeel, Rixin, Steroids, Streptozocin, Taxol, Taxotere, Thioguanine, Thiotepa, Tomudex, Topotecan, Treosulfan, Trihydrate, Vinblastine, Vincristine, Vindesine, Vinorelbina, Vinorelbine, duanomycin, dactinomysin, esorubisin, mafosfamide, cytosine arabinoside, bis-chloroethylnitrosurea, Mitomycin C, mithramycin, prednisone, hydroxyprogesterone, testosterone, tamoxifen, dacarbazine, hexamethylmelamine, pentamethylmelamine, amsacrine, chlorambudil, methylcyclohexylnitrosurea, nitrogen mustards, Cyclophosphamide, 6-mercaptopurine, 6-thioguanine, cytarabine, 5-azacytidine, deoxyco-formycin, 4-hydroxyperoxycyclophosphoramide, 5-fluorouracil (5-FU), 5-fluorodeoxyuridine (5-FUdR), colchicine, trimetrexate, teni-poside, diethylstilbestrol.

However, reference to "cellular toxin" should also be understood to extend to any other molecule which is perhaps not traditionally regarded as a cytotoxic agent but nevertheless falls within the scope of the present definition on the basis that it induces cellular damage, for example DNA damage, such as nucleophosmin or agents which induce cellular damage as part of a synergistic process with another agent. Examples include catalytic antibodies, prodrugs, CHK1/2 inhibitor (such as CBP-501 or AZD7762), histone deacetylase inhibitor (such as vorinostat), tumour necrosis factor related apoptosis inducing ligand or BH3 mimetic (such as ABT737), small molecule inhibitors such as the tyrosine kinase inhibitors imatinib mesylate (Glivec®), gefitinib (Iressa®) and erlotinib (Tarceva®), and the monoclonal antibodies (mAb) such as rituximab (Mabthera®) and trastuzumab (Herceptin®).

In yet another embodiment, combination treatments may include, for example, gemcitabine together with a CHK1/2 inhibitor or irinotecam together with a CHK1/2 inhibitor.

In a still further embodiment, the cellular toxin may be a molecule which functions as an RNA interference mechanism. Without limiting the present invention to any one theory or mode of action "RNA interference" broadly describes a mechanism of gene silencing which is based on degrading or otherwise preventing the translation of mRNA in a sequence specific manner. In terms of the application of this technology to selectively knocking down gene expression, exogenous double stranded RNA (dsRNA) specific to a gene sought to be knocked down can be introduced into the intracellular environment. Once the dsRNA enters the cell, it is cleaved by an RNaseIII-like enzyme, Dicer, into double stranded small interfering RNAs (siRNAs) 21-23 nucleotides in length that contain 2 nucleotide overhangs on the 3' ends. In an ATP dependent step, the siRNAs become integrated into a multi-subunit protein complex known as the RNAi induced silencing complex (RISC), which guides the siRNAs to the target RNA sequence. The siRNA unwinds and the antisense strand remains bound to RISC and directs degradation of the complementary target mRNA sequence by a combination of endo- and exonucleases. However, whereas the RNAi mechanism was originally identified in the context of its role as a microbial defence mechanism in higher eukaryotes, it is also known that RNAi based gene expression knockdown can also function as a mechanism to regulate endogenous gene expression. Specifically, microRNA (miRNA) is a form of endogenous single-stranded RNA which is typically 20-25 nucleotides and is endogenously transcribed from DNA, but not translated into protein. The DNA sequence that codes for an miRNA gene generally includes the miRNA sequence and an approximate reverse complement. When this DNA sequence is transcribed into a single-stranded RNA molecule, the miRNA sequence and its reverse-complement base pair to form a double stranded RNA hairpin loop, this forming the primary miRNA structure (pri-miRNA). A nuclear enzyme cleaves the base of the hairpin to form pre-miRNA. The pre-miRNA molecule is then actively transported out of the nucleus into the cytoplasm where the Dicer enzyme cuts 20-25 nucleotides from the base of the hairpin to release the mature miRNA.

Although both of the RNA interference mechanisms detailed above effectively achieve the same outcome, being selective gene expression knockdown, RNAi based on the use of exogenously administered dsRNA generally results in mRNA degradation while RNAi based on the actions of miRNAs generally results in translational repression by a mechanism which does not involve mRNA degradation. The RNA interference which is contemplated in the context of the present invention should be understood to encompass reference to both of these RNAi gene knockdown mechanisms. The induction of this miRNA based knockdown mechanism could be achieved by administering, in accordance with the method of the invention, exogenous RNA oligonucleotides of the same sequence as an miRNA, pre-miRNA or pri-miRNA molecules. However, it should be understood that these exogenous RNA oligonucleotides may lead to either mRNA degradation (analogous to that observed with the introduction of an exogenous siRNA population) or mRNA translateral repression, this being akin to the mechanism by which the endogenous miRNA molecules function. In terms of the objective of the present invention, the occurrence of either gene knockdown mechanism is acceptable.

The RNA interference mechanism herein discussed is effected via the use of an RNA oligonucleotide which can induce an RNA interference mechanism. Reference to an "RNA oligonucleotide" should therefore be understood as a reference to an RNA nucleic acid molecule which is double stranded or single stranded and is capable of either effecting the induction of an RNA interference mechanism directed to knocking down the expression of a gene targeted or down-regulating or preventing the onset of such a mechanism. In this regard, the subject oligonucleotide may be capable of directly modulating an RNA interference mechanism or it may require further processing, such as is characteristic of hairpin double stranded RNA which requires excision of the hairpin region, longer double stranded RNA molecules which require cleavage by dicer or precursor molecules such as pre-miRNA which similarly require cleavage. The subject oligonucleotide may be double stranded (as is typical in the context of effecting RNA interference) or single stranded (as may be the case if one is seeking only to produce a RNA oligonucleotide suitable for binding to an endogenously expressed gene). Examples of RNA oligonucleotides suitable for use in the context of the present invention include, but are not limited to:

(i) long double stranded RNA (dsRNA)—these are generally produced as a result of the hybridisation of a sense RNA strand and an antisense RNA strand which are each separately transcribed by their own vector. Such double stranded molecules are not characterised by a hairpin loop. These molecules are required to be cleaved by an enzyme such as Dicer in order to generate short interfering RNA (siRNA) duplexes. This cleavage event preferably occurs in the cell in which the dsRNA is transcribed.

(ii) hairpin double stranded RNA (hairpin dsRNA)—these molecules exhibit a stem-loop configuration and are generally the result of the transcription of a construct with inverted repeat sequences which are separated by a nucleotide spacer region, such as an intron. These molecules are generally of longer RNA molecules which require both the hairpin loop to be cleaved off and the resultant linear double stranded molecules to be cleaved by Dicer in order to generate siRNA. This type of molecule has the advantage of being expressible by a single vector.

(iii) short interfering RNA (siRNA)—these can be synthetically generated or, recombinantly expressed by the promoter based expression of a vector comprising tandem sense and antisense strands each characterised by its own promoter and a 4-5 thymidine transcription termination site. This enables the generation of 2 separate transcripts which subsequently anneal. These transcripts are generally of the order of 20-25 nucleotides in length. Accordingly, these molecules require no further cleavage to enable their functionality in the RNAi pathway.

(iv) short hairpin RNA (shRNA)—these molecules are also known as "small hairpin RNA" and are similar in length to the siRNA molecules but with the exception that they are expressed from a vector comprising inverted repeat sequences of the 20-25 nucleotide RNA molecule, the inverted repeats being separated by a nucleotide spacer. Subsequently to cleavage of the hairpin (loop) region, there is generated a functional siRNA molecule.

(v) micro RNA/small temporal RNA (miRNA/stRNA)—miRNA and stRNA are generally understood to represent naturally occurring endogenously expressed molecules. Accordingly, although the design and administration of a molecule intended to mimic the activity of a miRNA will take the form of a synthetically generated or recombinantly expressed siRNA molecule, the method of the present invention nevertheless extends to the design and expression of oligonucleotides intended to mimic miRNA, pri-miRNA or pre-miRNA molecules by virtue of exhibiting essentially identical RNA sequences and overall structure. Such recombinantly generated molecules may be referred to as either miRNAs or siRNAs.

(vi) miRNAs which mediate spatial development (sdRNAs), the stress response (srRNAs) or cell cycle (ccRNAs).

(vii) RNA oligonucleotides designed to hybridise and prevent the functioning of endogenously expressed miRNA or stRNA or exogenously introduced siRNA. It would be appreciated that these molecules are not designed to invoke the RNA interference mechanism but, rather, prevent the upregulation of this pathway by the miRNA and/or siRNA molecules which are present in the intracellular environment. In terms of their effect on the miRNA to which they hybridise, this is reflective of more classical antisense inhibition.

It will be appreciated that the person of skill in the art can determine the most suitable RNA oligonucleotide for use in any given situation. For example, although it is preferable that the subject oligonucleotide exhibits 100% complementarity to its target nucleic acid molecule, the oligonucleotide may nevertheless exhibit some degree of mismatch to the extent that hybridisation sufficient to induce an RNA interference response in a sequence specific manner is enabled. Accordingly, it is preferred that the oligonucleotide of the present invention comprises at least 70% sequence complementarity, more preferably at least 90% complementarity and even more preferably, 95%, 96%, 97%, 98% 99% or 100% sequence complementarity.

In another example pertaining to the design of oligonucleotides suitable for use in the present invention, it is within the skill of the person of skill in the art to determine the particular structure and length of the subject oligonucleotide, for example whether it takes the form of dsRNA, hairpin dsRNA, siRNA, shRNA, miRNA, pre-miRNA, pri-miRNA etc. For example, it is generally understood that stem-loop RNA structures, such as hairpin dsRNA and shRNA, are more efficient in terms of achieving gene knockdown than, for example, double stranded DNA which is generated utilising two constructs separately coding the sense and antisense RNA strands. Still further, the nature and length of the intervening spacer region can impact on the functionality of a given stem-loop RNA molecule. In yet still another example, the choice of long dsRNA, which requires cleavage by an enzyme such as Dicer, or short dsRNA (such as siRNA or shRNA) can be relevant if there is a risk that in the context of the particular cellular environment an interferon response could be generated, this being a more significant risk where long dsRNA is used than where short dsRNA molecules are utilised. In still yet another example, whether a single stranded or double stranded nucleic acid molecule is required to be used will also depend on the functional outcome which is sought. For example, to the extent that one is targeting an endogenously expressed miRNA with an antisense molecule, it would generally be appropriate to design a single stranded RNA oligonucleotide suitable for specifically hybridising to the subject miRNA. However, to the extent that it is sought to induce RNA interference, a double stranded siRNA molecule is required. This may be designed as a long dsRNA molecule which undergoes further cleavage or an siRNA. Still further, the present invention is preferably designed to result in the generation of a final effector RNA oligonucleotide (i.e. a siRNA or miRNA molecule) which is preferably less than 30 nucleotides in length, more preferably 15-25 nucleotides in length and most preferably 19, 20, 21, 22 or 23 nucleotides in length.

Stabilised particulate material in accordance with the invention can advantageously be maintained in a dispersed state at low concentrations. The ability for the particulate material to remain in a dispersed state in a diverse array of liquid carriers (including body fluids) at relatively low concentration, coupled with the ability to tailor the design of the stabiliser on a molecular level (e.g. its composition and molecular weight), may, without wishing to be limited by theory, play a role in enabling the particulate material to achieve deep penetration of solid tumours.

As used herein, the expression "particulate material" is intended to embrace material that is capable of being dispersed throughout the liquid carrier and that presents a surface to which the stabiliser may be associated.

The particulate material will generally be of a size that is less than about 500 nm, less than about 350 nm, less than about 250 nm, less than about 100 nm, less than about 50 nm, less than about 25 nm or less than about 15 nm.

In one embodiment, said particulate material is about: 2, 4, 6, 8, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm.

By having an ability to be dispersed throughout the liquid carrier, it will be appreciated that the particulate material will be sufficiently insoluble in the liquid carrier so as to enable the dispersion to have effective application.

The particulate material may be in the form of primary particles, or in the form or an aggregation of primary particles.

For avoidance of any doubt, reference herein to the "size" of the particulate material is intended to denote an average size (at least about 50 number %) of the particles based on the largest dimension of a given particle. The size of the particulate material per se is determined herein by Transmission Electron Microscopy (TEM).

For avoidance of any doubt, when the particulate material is in the form of an aggregation of primary particles, reference to the size of such material is intended to be a reference to the largest dimension of the aggregate not the primary particles that form the aggregate.

Apart from having medicinal utility in the context of the present application, there is no particular limitation on composition of the particulate material. The particulate material may have an organic composition or an inorganic composition or a combination thereof. The particulate material may be inorganic, organic or a combination thereof.

Examples of particulate material include one or more of a metal, a metal alloy, a metal salt, a metal complex, a metal oxide, an inorganic oxide, a radioactive isotope, a polymer particle, and/or combinations thereof.

More specific examples of particulate materials include gold, silver, boron, and salts, complexes or oxides thereof, calcium carbonate, barium sulphate, iron oxide, chromium oxide, cobalt oxide, manganese oxide, silicon oxide, iron oxyhydroxide, chromium oxyhydroxide, cobalt oxyhydroxide, manganese oxyhydroxide, chromium dioxide, other transition metal oxides, polymers such as polystyrene, poly (methyl methacrylate) and poly(butadiene).

In some embodiments of the invention, it is preferred that the particulate material is magnetic. Magnetic particulate material that may be used in accordance with the invention will generally be of a size of less than about 350 nm. Those skilled in the art will appreciate that the composition and/or size of the particles can influence their magnetic properties. The magnetic particulate material will generally exhibit ferromagnetic, ferrimagnetic or superparamagnetic properties.

The specific size of the magnetic particulate material used will generally be dictated by the intended application of the compositions. For some applications, it may be desirable for the magnetic particulate material to be of a size of less than about 300 nm, for example less than about 100 nm, or less than about 50 nm.

There is no particular limitation on the type of magnetic particulate material that may be used in accordance with the invention. Examples of suitable magnetic materials include, but are not limited to, iron, nickel, chromium, cobalt, oxides thereof or mixtures of any of these. Preferred iron oxide magnetic particulate materials include γ-ion oxide (i.e. γ-$Fe_2O_3$, also known as maghemite) and magnetite ($Fe_3O_4$).

In some applications, it may be desirable to use magnetic material that is superparamagnetic (i.e. nano-superparamagnetic particles). As used herein, the term "superparamagnetic" is intended to mean magnetic particles that do not have the following properties; (i) coercivity, (ii) remanence, or (iii) a hysteresis loop when the rate of change of an applied magnetic field is quasi static.

The magnetic material is preferably selected from ferrites of general formula $MO.Fe_2O_3$ where M is a bivalent metal such as Fe, Co, Ni, Mn, Be, Mg, Ca, Ba, Sr, Cu, Zn, Pt or mixtures thereof, or magnetoplumbite type oxides of the general formula $MO.6Fe_2O_3$ where M is a large bivalent ion, metallic iron, cobalt or nickel. Additionally, they could be particles of pure Fe, Ni, Cr or Co or oxides of these. Alternatively they could be mixtures of any of these.

In one embodiment, the magnetic particulate material is or comprises iron oxide such as magnetite ($Fe_3O_4$) or maghemite (γ-$Fe_2O_3$) with a particle size preferably less than 50 nm, for example between 2 and 40 nm.

Particulate material used in accordance with the invention may conveniently be prepared using techniques known in the art.

In accordance with the invention, the particulate material is maintained in the dispersed state by a stabiliser. By being "maintained" in this context is meant that in the absence of the stabiliser the particulate material would otherwise flocculate or settle out from the liquid carrier as sediment. In other words, the stabiliser functions to retain the particulate material in the dispersed state.

The particulate material is in the form of a dispersion within a liquid carrier, the particulate material being maintained in the dispersed state by a stabiliser. By "stabiliser" is meant an agent that associates with the particulate material and assists with preventing it from flocculating or otherwise becoming non-dispersed within the liquid carrier.

The stabiliser used in accordance with the invention comprises an anchoring portion that (a) anchors the stabiliser to the particulate material, and (b) is different from the remainder of the stabiliser.

By an "anchoring portion" is meant a moiety such as an atom or group of covalently coupled atoms that functions to anchor the stabiliser to the particulate material.

By an anchoring portion that "anchors" the stabiliser to the particulate material is meant it is the anchoring portion per se that directly tethers or binds the stabiliser to the particulate material.

The anchoring portion therefore binds the stabiliser to the particulate material.

There is no particular limitation on the way in which the stabiliser is anchored to the particulate material. For example, it may be covalently coupled to the particulate material, and/or secured to the particulate material through electrostatic forces, hydrogen bonding, ionic charge, van der Waals forces, or any combination thereof.

The stabiliser functions to prevent the particulate material from flocculating or otherwise becoming non-dispersed (i.e. aggregated) within the liquid carrier through known mechanisms such as steric repulsion, electrosteric repulsion and/or electrostatic repulsion.

Without wishing to be limited by theory, use of a stabiliser in accordance with the invention is believed to facilitate (i) transport of the particulate material in vivo to the site of the solid tumour, and/or (ii) penetration the particulate material throughout the solid tumour, and/or (iii) uptake by subpopulations of cells within the tumour that would not otherwise accumulate effective doses of the cellular toxin.

One or more stabiliser can be used in accordance with the present invention.

By the anchoring portion being "different" to the remainder of the stabiliser is meant that the anchoring portion has a different structure or molecular composition to the rest of the stabiliser. In other words, the stabiliser will have a stabilising portion (i.e. the portion that functions as a stabilising moiety) and an anchoring portion (i.e. the portion that functions to secure or bind the stabiliser to the particulate material). The stabilising portion and the anchoring portion are different.

By providing the stabiliser with different structural features that give rise to the stabilising and anchoring functions, it has been found that practical effect of both functions can be enhanced. Without wishing to be limited by theory, a strong association between the particulate material and the stabiliser (provided by the anchoring portion), in combination with dedicated stabilising moiety is believed to enable the particulate material to be maintained in a dispersed state throughout a diverse array of liquid carriers at very low concentrations. Such properties make the particulate material well suited to being maintained in a dispersed state post administration within body fluids.

Those skilled in the art will appreciate that stabilisers with a unique anchoring portion can function differently to stabilisers without such a unique anchoring portion. For example, a stabiliser such as polyethylene glycol (PEG) can adsorb to the surface of a particulate material and function as a stabiliser. In that case, any part(s) of the PEG chain, which does not have an anchoring portion that is different from the remainder of the stabiliser, will adsorb in a random fashion giving rise to a non-uniform surface stabilising layer.

In contrast, by providing a stabiliser with a stabilising portion and different anchoring portion arrangement a more controlled and uniform surface stabilising layer can advantageously be formed. For example the presence of the unique anchoring portion can promote on the surface of the particulate material a brush stabilising layer, where the anchoring portion is secured to the surface of the particulate material and the remainder of the stabiliser (i.e. the stabilising portion) extends out from the surface of the particulate material into the liquid carrier akin to the bristles extending from the surface of a brush (hence the name "brush" stabilising layer). As a case in point, the PEG stabiliser mentioned above might be functionalised with one or more carboxylic acid groups at the end of the PEG chain to provide for an anchoring portion. The acid functionalised anchoring portion, which is different from the remainder of the stabiliser, can then secure or bind the PEG chain to the particulate material and allow it to extend freely into the carrier liquid.

Suitable stabilisers may be nonionic, anionic, cationic, or zwitterionic.

In one embodiment, the particulate material is maintained in the dispersed state by a steric stabiliser, wherein the steric stabiliser comprises a steric stabilising polymeric segment and an anchoring portion, wherein the steric stabilising polymeric segment is different from the anchoring portion, and wherein the anchoring portion binds the stabiliser to the particulate material.

In a similar manner to that outlined above, steric stabilising polymeric segment functions to stabilise the particulate material within the liquid carrier, and the anchoring portion functions to secure the stabiliser to the particulate material. By providing the stabiliser with different structural features that give rise to the steric stabilising and anchoring functions, it has been found that practical effect of both functions can be enhanced.

Examples of suitable stabilisers include, but are not limited to, those having a polymeric stabilising segment.

The stabilising segment will be soluble in the liquid carrier.

In one embodiment, the polymeric stabilising segment comprises polymer selected from polyacrylamide, polyethylene oxide, polyhydroxyethylacrylate, poly N-isopropylacrylamide, polydimethylaminoethylmethacrylate, polyvinyl pyrrolidone and copolymers thereof.

In another embodiment, the anchoring portion comprises one or more carboxylic acid groups, one or more phosphate groups, one or more phosphonate groups, one or more phosphinate groups, one or more thiol groups, one or more thiocarbonylthio groups, one or more sulfonic acid groups, one or more ethoxysilyl groups, and combinations thereof.

In one embodiment, the anchoring portion is an anchoring polymeric segment and at least one of the steric stabilising and anchoring polymeric segments comprise polymerised residue of one or more ethylenically unsaturated monomers. Employing at least one such polymeric segment is believed to enhance the stabilising properties of the steric stabiliser.

In one embodiment, the anchoring portion is an anchoring polymeric segment and at least one of the steric stabilising and anchoring polymeric segments is derived from one or more ethylenically unsaturated monomers that have been polymerised by a living polymerisation technique. Employing at least one such polymeric segment is believed to enhance the stabilising properties of the steric stabiliser.

By being a "steric" stabiliser is meant that stabilisation of the particulate material throughout the liquid carrier occurs as a result of steric repulsion forces. Having said this, the steric stabiliser may present electrostatic repulsion forces that also assist with stabilisation of the particulate material. The steric stabilising function of the stabiliser used in accordance with the invention therefore plays an important role in enabling the particulate material to be maintained in a dispersed state throughout a diverse array of liquid carriers, including body fluids.

In one embodiment, the stabiliser used in accordance with the invention comprises an ionisable functional group that does not form part of the anchoring portion and presents within the carrier liquid a cationic or anionic charge. Stabiliser comprising such ionisable functional group(s) (e.g. amine or carboxylic acid) may be present in an amount ranging from about 2 wt % to about 50 wt %, or about 5 wt % to about 40 wt %, relative to the total wt % of stabiliser used. The use of this type of stabiliser provides for electrosteric stabilisation. The presence of such stabiliser has surprisingly been found to enhance penetration of the particulate material.

In one embodiment, the stabiliser comprises a steric stabilising polymeric segment having a terminal (i.e. at the end of the polymer segment or chain) functional group. The functional group may be an ionisable functional group, such as one that can provide for a cation (e.g. amine) or an anion (carboxylic acid). In one embodiment the ionisable functional group provides for a cation.

In a further embodiment, the stabiliser comprises a steric stabilising polymeric segment having a terminal functional group selected from an amine, a carboxylic acid and an alcohol.

The amount of stabiliser used relative to the particulate material will vary depending on the nature of the particulate material, particularly its size. For example, 1 g of 5 nm particulate material will require more stabiliser than 1 g of 1 micron particulate material due to its increased surface area. Those skilled in the art will be able to determine the required amount of stabiliser for a given particulate material.

For avoidance of any doubt, reference herein to specific features of the "stabiliser" is intended to embrace all forms of stabilisers contemplated for use in accordance with the invention (i.e. where the stabiliser comprises an anchoring portion that is different form the remainder of the stabiliser, or where the stabiliser is a steric stabiliser comprising a steric stabilising polymeric segment and an anchoring portion, wherein the steric stabilising polymeric segment is different from the anchoring portion).

In one embodiment, the stabiliser used in accordance with the invention comprises a polymeric structure. There is no particular limitation on the molecular weight of the stabiliser, and this feature of the stabiliser may be dictated in part on the mode by which the dispersion is to be administered to a subject. The stabiliser may, for example, have a number average molecular weight of up to about 160,000, or up to about 150,000, or up to about 100,000, or up to about 50,000.

In one embodiment, the stabilisers used in accordance with the present invention will have a relatively low number average molecular weight compared with stabilisers conventionally used to stabilise particulate material.

In some embodiments of the invention, it may be preferable that the number average molecular weight of the stabiliser is less than about 30,000, or less than about 20,000, or less than about 10,000, or even less than about 5,000. The number average molecular weight of the stabiliser may also range from about 1,000 to about 3,000.

Stabilisers used in accordance with the invention having a quite low number average molecular weight (e.g. less than about 5,000, preferably in the range of from about 1,000 to about 3,000) have been found to be particularly effective at stabilising particulate material in vivo.

Molecular weight values referred to herein are number average molecular weight values (Mn). If appropriate, the molecular weight is to be determined using gel permeation chromatography (GPC). GPC can be performed using polystyrene standards for hydrophobic polymers and polyethylene oxide standards for hydrophilic polymers.

Those skilled in the art will appreciate that determination of the molecular weight for a block copolymer may require additional procedures. For example, it may useful to determine the molecular weight of the first block before the second block is added. If a block is less than about 3000 molecular weight this can be determined by electrospray mass spectroscopy (EMS). For higher molecular weigh blocks, GPC can be employed using polystyrene standards for hydrophobic blocks and polyethylene oxide standards for hydrophilic blocks.

Determining the molecular weight of an overall block copolymer will typically depend on the length of the two blocks and their solubility characteristics. The molecular weight of low molecular weight block copolymers can be determined by EMS as mentioned above. For higher molecular weight block copolymers for which suitable solvents and standards can be found, GPC may be used. For example, if both blocks are hydrophobic and soluble in, for example, tetrahydrofuran (THF), GPC can be carried out against polystyrene standards; if both blocks are hydrophilic and soluble in, for example, THF, it may be useful to use polyethylene oxide standards, rather than polystyrene standards. However, it may be that the blocks of a block copolymer are too dissimilar to allow for a common dissolving solvent; poly acrylamide-b-polystyrene is an example of such a block copolymer. In that case, it will generally be necessary to prepare and characterise the first block and then grow the second block and calculate the molecular weight of the second block on the basis of the degree of conversion of monomer to polymer.

Stabilisers used in accordance with the invention can advantageously exhibit highly efficient stabilising properties in that stabilisation of the particulate material can be achieved at both low and high concentrations of the particulate material within a liquid carrier. The stabilisers can also provide for stable dispersions of the particulate material throughout a diverse array of liquid carriers, such as those having a high ionic strength (e.g. 0.15 M NaCl solution, and even as high as in a saturated NaCl solution at room temperature), and also over a wide pH range. Such properties make the dispersions particularly suitable for in vivo applications.

Without wishing to be limited by theory, the highly efficient stabilising properties that can be provided by the stabilisers are believed to stem at least in part from stabilisers comprising an anchoring portion that is separate to and different from the stabilising portion and securely anchors the stabiliser to the particulate material.

By reference the stabiliser being "anchored" to the particulate material, or wherein the anchoring portion "anchors" the stabiliser to the particulate material, is meant that the stabiliser is securely attached to the particulate material within a liquid carrier and can remain so attached in the absence of free stabiliser in the liquid carrier, where the liquid carrier has a high ionic strength (e.g. saturated aqueous sodium chloride solution), and/or where the liquid carrier has a low ionic strength (e.g. pure water).

Anchoring of the stabiliser to the particulate material may be achieved as a result of the anchoring portion being (1) covalently coupled to the particulate material, and/or (2) secured to the particulate material through electrostatic forces, hydrogen bonding, ionic charge, Van der Waals forces, or any combination thereof.

As a result of the stabilisers being anchored to the particular material, the particulate material can be maintained in a dispersed state within the liquid carrier despite it being present at low or high concentration and/or the liquid carrier having low or high ionic strength.

Accordingly, a dispersion of the particulate material in a liquid carrier in accordance with the invention can be advantageously stable (i.e. does not flocculate) under conditions that conventionally stabilised particulate material would be unstable (i.e. would flocculate).

Those skilled in the art will appreciate that stabilisers that are not covalently bound to particulate material generally stabilise and maintain particulate material in a dispersed state by existing in a state of equilibrium of being adsorbed to and desorbed from the particulate material. Accordingly, where a stabiliser is present at a relatively low concentration in a given liquid carrier, the equilibrium is generally shifted in favour of the stabiliser being desorbed from the particulate material, which in turn results in flocculation of the particulate material.

Where anchoring occurs by the stabiliser being covalently coupled to the particulate material, there can of course be no desorption of the stabiliser. Where anchoring occurs by other means, the stabilisers used in accordance with the present invention are nevertheless securely attached to the particulate material and therefore undergo little if no desorption from the particulate material even when present at low concentration within the liquid carrier. In other words, when present at low concentration within the liquid carrier the equilibrium of adsorbed stabilisers used in accordance with the invention is strongly in favour of the stabiliser being adsorbed to the particulate material, which in turn facilitates the particulate material being maintained in a dispersed state.

A convenient test to confirm the anchoring characteristic of stabilisers used in accordance with the invention, which in turn may also reflect their ability to maintain the particulate material in the required dispersed state, can be performed by diluting the steric stabilised particulate material to 1% solids using a suitable liquid carrier (typically water), centrifuging this solution so that the solids form a plug, and then removing the supernatant liquid to isolate the solid plug. The solid plug is then combined with a suitable liquid carrier (typically water) without adding more stabiliser so as to again form 1% solids. Sodium chloride is then added to the resulting solution to yield 10% by weight sodium chloride. If the particulate material can be redispersed in this final solution and remains dispersed for at least 1 hour, the steric stabilisers are regarded as being anchored to the particulate material.

By "steric stabilising polymeric segment" is meant a segment or region of the steric stabiliser that is polymeric (i.e. formed by the polymerisation of at least one type of monomer) and that provides for the steric stabilising function of the steric stabiliser. For convenience, the steric stabilising polymeric segment may hereinafter be referred to as polymeric segment "A".

As mentioned, the steric stabilising polymeric segment functions to stabilise the particulate material throughout the liquid carrier by providing steric repulsion forces.

By being polymeric, it will be appreciated that the steric stabilising segment comprises polymerised monomer residues. Thus, the segment will comprise polymerised monomer residues that give rise to the required steric stabilising properties. The polymerised monomer residues that make up the steric stabilising polymeric segment may be the same or different.

The steric stabilising polymeric segment may be substituted with a moiety (e.g. an optional substituent as herein defined), or contain a polymerised monomer residue, that gives rise to electrostatic stabilising properties.

To provide the desired stabilising effect, the stabilising portion will be soluble in at least the liquid carrier. The solubility of a given stabilising portion in a given liquid carrier can readily be determined by simply preparing the stabilising portion in isolation and conducting a suitable solubility test in the chosen liquid carrier.

Similarly, to provide the desired steric stabilising effect, the steric stabilising polymeric segment will be soluble in at least the liquid carrier. The solubility of a given steric stabilising polymeric segment in a given liquid carrier can readily be determined by simply preparing the polymeric segment in isolation and conducting a suitable solubility test in the chosen liquid carrier.

The stabiliser as a whole, may or may not be soluble in the given carrier liquid, but will nonetheless present a stabilising portion that is soluble.

Those skilled in the art will have an understanding of polymeric materials that may be employed as the steric stabilising polymeric segment, as to the monomers that may be polymerised to form such polymers. For example, suitable polymeric materials include, but are not limited to, polyacrylamide, polyethylene oxide, polyhydroxyethylacrylate, poly N-isopropylacrylamide, polydimethylaminoethylmethacrylate, polyvinyl pyrrolidone and copolymers thereof. Thus, suitable monomers that may be used to form the stabilising polymeric segment include, but are not limited to, acrylamide, ethylene oxide, hydroxyethylacrylate, N-isopropylacrylamide, dimethylaminoethylmethacrylate, vinyl pyrrolidone and combinations thereof.

The particular steric stabilising polymeric segment used as part of the steric stabiliser will of course depend upon the nature of the liquid carrier. For example, if an aqueous liquid carrier is used, the steric stabilising polymeric segment should be soluble in the aqueous media. Those skilled in the art will be able to select an appropriate steric stabilising polymeric segment for the chosen liquid carrier.

By being able to select a specific steric stabilising polymeric segment independent of the anchoring portion, steric stabilisers used in accordance with the invention can advantageously be tailor designed to suit a particular liquid carrier and thereby maximise the stabilising properties of the steric stabiliser.

There is no particular limitation concerning the polymerisation that technique may be used to prepare the steric stabilising polymeric segment. Living polymerisation techniques have been found particularly useful in that regard. Those skilled in the art will appreciate that "living polymerisation" is a form of radical addition polymerisation whereby chain growth propagates with essentially no chain transfer and essentially no termination that give rise to dead polymer chains. By a "dead polymer chain" is meant one that can not undergo further addition of monomers.

In a living polymerisation, typically all polymer chains are initiated at the start of the polymerisation with minimal new chains being initiated in latter stages of the polymerisation. After this initiation process, all the polymer chains in effect grow at the same rate. Characteristics and properties of a living polymerisation generally include (i) the molecular weight of the polymer increases with conversion, (ii) there is a narrow distribution of polymer chain lengths (i.e. they are of similar molecular weight), and (iii) additional monomers can be added to the polymer chain to create block co-polymer structures. Thus living polymerisation enables excellent control over molecular weight, polymer chain architecture and polydispersity of the resulting polymer that can not be achieved with non-living polymerisation methods.

Suitable living polymerisation techniques may be selected from ionic polymerisation and controlled radical polymerisation (CRP). Examples of CRP include, but are not limited to, iniferter polymerisation, stable free radical mediated polymerisation (SFRP), atom transfer radical polymerisation (ATRP), and reversible addition fragmentation chain transfer (RAFT) polymerisation.

The steric stabilising polymeric segment may be formed by the polymerisation of one type of monomer or a combination of two or more different monomers. Accordingly, the steric stabilising polymeric segment may be a homopolymeric segment or a copolymeric segment.

Given that the stabilising polymeric segment forms only part of the steric stabiliser, rather than defining the steric stabilising polymeric segment in terms of its number average molecular weight, it can instead be useful to make reference to the number of polymerised monomeric units that collectively form the segment. Thus, although there is no particular limitation on the number of such units that collectively form the steric stabilising polymeric segment, in some embodiments of the invention it may be desirable that the steric stabiliser has a relatively low number average molecular weight. In that case, it is preferable that the steric stabilising polymeric segment has less than about 100, more preferably less than about 50, most preferably from about 10 to about 30 polymerised monomer residue units that make up the overall segment.

The steric stabilisers used in accordance with the invention also comprise an anchoring portion. The function of the anchoring portion has been mentioned. Provided that the stabiliser can be suitably anchored to the particulate material and is different to the steric stabiliser, there is no particular limitation concerning the form of the anchoring portion.

The anchoring portion will be covalently coupled to the steric stabilising segment. For convenience, the anchoring portion may be represented as "B". The steric stabilising polymeric segment and the anchoring portion may be covalently coupled by any suitable means. For example, the steric stabiliser may be described as or comprising the structure A-C-B, where A represents the steric stabilising polymeric segment, B represents the anchoring portion and C represents a coupling moiety. Alternatively, the steric stabilising polymeric segment and the anchoring portion may be directly covalently coupled and therefore the stabiliser can be simplistically described as or comprising the structure A-B. In that case, A represents the steric stabilising polymeric segment and B represents the anchoring portion.

The specific anchoring portion used will generally be dictated by the nature of the particulate material to which it is to be anchored. Those skilled in the art will be able to select an appropriate anchoring portion to bind with the surface of a given particulate material.

When selecting the steric stabilising segment and anchoring portion, it may be desirable to consider the properties of these respective components in the context of the intended application of the dispersion. For example, one or both of the steric stabilising segment and anchoring portion may be selected such that they are biodegradable and/or biocompatible.

The anchoring portion may be present as one or more moieties that form a covalent bond with the particulate material so as to covalently couple the stabiliser to the particulate material. For example, the anchoring portion (in an anchored state) may be derived from a thiol moiety (—SH) that covalently couples the stabiliser to the particulate material via a —S— linkage. In other words, the stabiliser used comprises a thiol moiety, but it will be covalently coupled to the particle via a —S— linkage. Accordingly, reference to a stabiliser "used" in accordance with the invention is intended to be a reference to the form of the stabiliser prior to it being anchored to the particulate material.

The anchoring portion may be a polymeric segment, or in other words an anchoring polymeric segment. In this form, anchoring of the stabiliser to the particulate material will generally not be by way of covalent coupling but rather by way of electrostatic forces, hydrogen bonding, ionic charge, Van der Waals forces, or any combination thereof.

By an "anchoring polymeric segment" is meant a segment or region of the steric stabiliser that is polymeric and that has an affinity toward the surface of the particulate material and functions to anchor or bind the steric stabiliser to the particulate material. For convenience, the anchoring polymeric segment may also be represented as "B".

By being polymeric, it will be appreciated that the anchoring segment comprises polymerised monomer residues. The segment will comprise polymerised monomer residues that give rise to the required anchoring to the particulate material. The polymerised monomer residues that make up the anchoring polymeric segment may be the same or different.

The anchoring polymeric segment can present multiple sites for binding interactions with the particulate material and it is believed that this property enables the stabiliser to be anchored securely to the particulate material despite not being covalently coupled thereto.

Generally, the anchoring polymeric segment will have at least two polymerised monomer residues that each provides a site for binding with the particulate material, preferably at least three, more preferably at least five, still more preferably at least seven, most preferably at least ten of such polymerised monomer residues. Not all of the polymerised monomer residues that make up the anchoring polymeric segment are necessarily required to give rise to a binding interaction with the particulate material, but it is generally preferred that the majority if not all of the polymerised monomer residues that make up the anchoring polymeric segment do give rise to a binding interaction with the particulate material.

The anchoring polymeric segment may therefore be described as having multiple sites that collectively anchor the stabiliser to the particulate material. Even where a given binding site only provides a relatively weak interaction with the particulate material, the presence of multiples of such sites within the segment enables it as a whole to bind securely with the particulate material.

The anchoring polymeric segment can also be substituted with a moiety (e.g. an optional substituent as herein defined) that may or may not give rise to a binding interaction with the particulate material.

The specific anchoring polymeric segment used will generally be dictated by the nature of the particulate material to which it is to bind.

When describing the interaction of the anchoring polymeric segment with the particulate material, it can be convenient to refer to the hydrophilic and hydrophobic character of the segment and the particulate material. Thus, in general, suitable binding interactions will occur when the segment and the particulate material have similar hydrophilic or hydrophobic character. For example, where the particulate material has a relatively hydrophilic surface (e.g. its surface can be wetted with water), then good binding should be attained using an anchoring polymeric segment that has hydrophilic character (e.g. in its isolated form the segment would be soluble in an aqueous medium).

Such an example might be realised where the particulate material is of a type that can form a charge on its surface. In that case, it may be desirable for the segment to comprise polymerised residues of monomers that can also form a charge (e.g. residues of an ionisable monomer) so as to promote ionic binding between the segment and the particulate material. Promoting the formation of such charged species might be facilitated by adjusting the pH of the liquid carrier in which the stabiliser and particulate material reside.

By the term "ionisable monomer" is meant that the monomer comprises a functional group which can be ionised in solution to form a cationic or anionic group. Such functional groups will generally be capable of being ionised under acidic or basic conditions through loss or acceptance of a proton. Generally, the functional groups are acid groups or basic groups (i.e. groups that can donate or accept a H atom, respectively). For example, a carboxylic acid functional group may form a carboxylate anion under basic conditions, and an amine functional group may form a quaternary ammonium cation under acidic conditions. The functional groups may also be capable of being ionised through an ion exchange process.

Examples of suitable ionisable monomers having acid groups include, but are not limited to, methacrylic acid, acrylic acid, itaconic acid, p-styrene carboxylic acids, p-styrene sulfonic acids, vinyl sulfonic acid, vinyl phosphonic acid, monoacryloxyethyl phosphate, 2-(methacryloyloxy) ethyl phosphate, ethacrylic acid, alpha-chloroacrylic acid, crotonic acid, fumaric acid, citraconic acid, mesaconic acid, and maleic acid. Examples of suitable ionisable monomers which have basic groups include, but are not limited to, 2-(dimethyl amino) ethyl and propyl acrylates and methacrylates, and the corresponding 3-(diethylamino) ethyl and propyl acrylates and methacrylates.

Those skilled in the art will be able to select an appropriate anchoring polymeric segment to bind with the surface of a given particulate material.

By being able to select a specific anchoring polymeric segment independent of the steric stabilising polymeric segment, the steric stabilisers used in accordance with the invention can advantageously be tailor designed to suit a particular particulate material and thereby maximise the anchoring properties of the steric stabiliser. For example, it may be desirable that the anchoring polymeric segment comprise carboxylic acid, phosphinate, phosphonate and/or phosphate functional groups. Where the particulate material to which anchoring segment binds comprises iron (e.g. magnetic iron oxide particulate material), it may be desirable for the segment to comprise phosphinate, phosphonate, and/or phosphate functional groups. Such segments will generally be formed using monomers that comprise the phosphorous functional groups.

Those skilled in the art will appreciate the variety of polymeric materials that may be employed as the anchoring polymeric segment, as to the monomers that may be polymerised to form such polymers. For example, suitable polymeric materials include, but are not limited to, polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, the corresponding poly-3-(diethylamino) ethyl and propyl acrylates and methacrylates, hydrophobic acrylate and methacrylate polymers, polydimethylaminoethylmethacrylate, and copolymers thereof. Thus, suitable monomers that may be used to form the anchoring polymeric segment include, but are not limited to, acrylic acid, methacrylic acid, itaconic acid, p-styrene carboxylic acids, p-styrene sulfonic acids, vinyl sulfonic acid, vinyl phosphonic acid, monoacryloxyethyl phosphate, 2-(methylacryloyloxy) ethyl phosphate, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, the corresponding 3-(diethylamino) ethyl and propyl acrylates and methacrylates, styrene, hydrophobic acrylate and methacrylate monomers, dimethylaminoethylmethacrylate, and combinations thereof.

Living polymerisation techniques such as those herein described have been found particularly useful in preparing the anchoring polymeric segment.

Where the anchoring portion is an anchoring polymeric segment, at least one of the steric stabilising and anchoring polymeric segments may be derived from one or more ethylenically unsaturated monomers that have been polymerised by a living polymerisation technique. Where only one of the segments is derived in this manner, it will preferably be the anchoring polymeric segment.

The anchoring polymeric segment may be formed by the polymerisation of one type of monomer or a combination of two or more different monomers. Accordingly, the anchoring polymeric segment may be a homopolymeric segment or a copolymeric segment.

Given that the anchoring polymeric segment may form only part of the steric stabiliser, rather than defining the anchoring polymeric segment in terms of its number average molecular weight, it can instead be useful to make reference to the number of polymerised monomeric units that collectively form the segment. Thus, although there is no particular limitation on the number of such units that collectively form the anchoring polymeric segment, in some embodiments of the invention it may be desirable that the steric stabiliser has a relatively low number average molecular weight. In that case, it is preferable that the anchoring polymeric segment has less than about 100, more preferably less than about 40, still more preferably less than about 30, even more preferably from about 5 to about 25, most preferably from about 5 to about 15 polymerised monomer residue units that make up the overall segment.

When selecting the steric stabilising and anchoring polymeric segment, or the monomers that may be used to prepare them, it may be desirable to consider the properties of the respective polymeric segments in the context of the intended application of the dispersion. For example, one or both polymeric segment may be selected such that they are biodegradable and/or biocompatible.

Provided that the stabiliser functions as herein described there is no particular limitation on how the stabilising polymeric segment and the anchoring polymeric segment are to be spatially arranged.

The steric stabilising polymeric segment and the anchoring polymeric segment may be coupled to each other by any suitable means to form the steric stabiliser used in accordance with invention. For example, the steric stabiliser may be described as or comprising the structure A-C-B, where A represents the steric stabilising polymeric segment, B represents the anchoring polymeric segment and C represents a coupling moiety. Alternatively, the steric stabilising polymeric segment and the anchoring polymeric segment may be directly coupled to each other via a covalent bond and therefore the stabiliser can be simplistically described as or comprising an A-B block copolymer. In that case, A represents the steric stabilising polymeric segment and B represents the anchoring polymeric segment.

It will be appreciated from the description above that each of A and B can independently be a homopolymer or a copolymer (e.g. random, block, tapered, etc.). The stabiliser may comprise more than one steric stabilising polymeric segment (A) and more than one anchoring polymeric segment (B). For example, the stabiliser may be described as or comprising an A-B-A block copolymer. In that case, each A represents the steric stabilising polymeric segment, which may be the same or different, and B represents the anchoring polymeric segment. The stabiliser might also be described as or comprising a B-A-B block copolymer, where each B represents the anchoring polymeric segment, which may be the same or different, and A represents the steric stabilising polymeric segment that is of sufficient chain length such that it forms a "loop" that extends into the liquid carrier and performs its stabilising role.

The stabiliser may also have more complex structures such as star and comb polymer structures. In that case, the anchoring polymeric segment B might represent the main polymer backbone of such structures, with multiple steric stabilising polymeric segments A being attached thereto.

Figure 13:
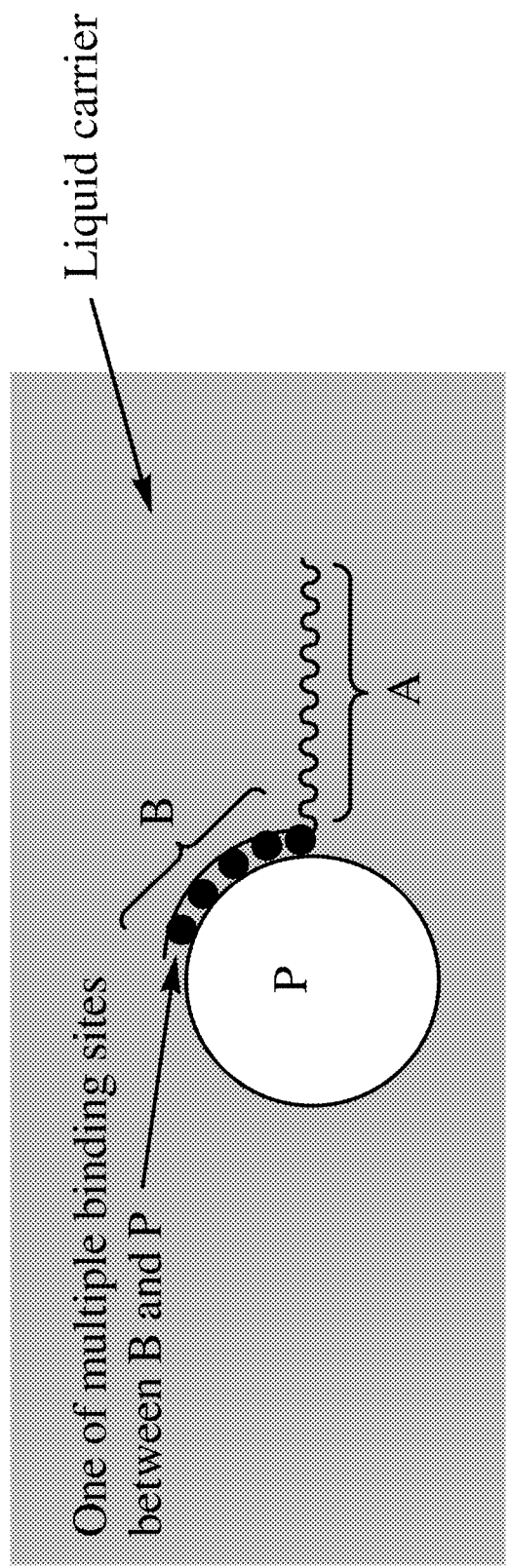
FIG. 13 shows a schematic illustration of stabilised particulate material that may be used in accordance with the present invention.

The interaction of a steric stabiliser used in accordance with the invention (in the form of an A-B block copolymer structure) with particulate material in the liquid carrier might be illustrated in the not to scale simplified schematic shown in FIG. 13.

With reference to FIG. 13, the steric stabiliser represented by an A-B block copolymer exhibits an affinity toward the surface of the particulate material (P) through the anchoring polymeric segment (B). The anchoring polymeric segment (B) therefore secures the steric stabiliser to the particulate material. The anchoring polymeric segment (B) provides multiple sites for binding interactions between the segment and the particulate material. The steric stabilising polymeric segment (A), which is different to segment (B), is soluble in the liquid carrier and functions to maintain the particulate material dispersed throughout the liquid carrier. It will be appreciated that in practice the surface of the particulate material will have many steric stabilisers secured thereto, and that these have been omitted from the illustration in FIG. 13 for clarity.

Figure 14:
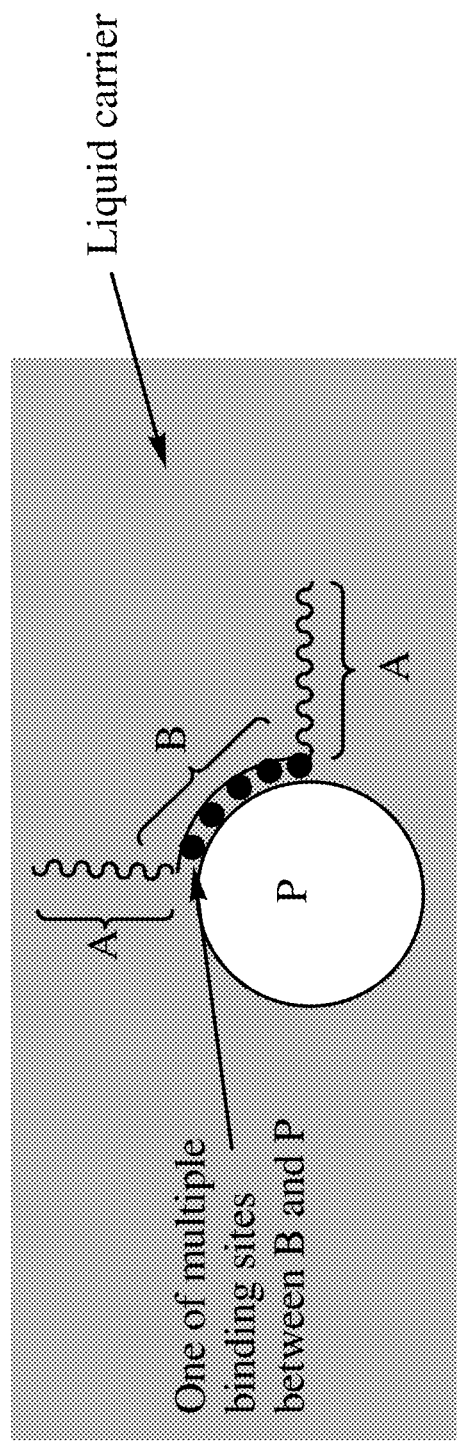
FIG. 14 shows a schematic illustration of stabilised particulate material that may be used in accordance with the present invention.

A similar illustration to that in FIG. 13 is shown in FIG. 14 where the steric stabiliser used in accordance with the invention is in the form of an A-B-A block copolymer.

At least one of the steric stabilising and anchoring polymeric segments may be derived from one or more ethylenically unsaturated monomers that have been polymerised by a living polymerisation technique such as ionic polymerisation, iniferter polymerisation, SFRP, ATRP, and RAFT polymerisation. Of these living polymerisation techniques, RAFT polymerisation is preferred.

The stabiliser used according to the invention may be prepared and then used to stabilise the particulate material. Alternatively, a moiety may be anchored to the particulate material and that moiety used to facilitate polymerisation of monomer so as to grow the stabiliser out from the particulate material.

Those skilled in the art will appreciate that the stabiliser selected for use in accordance with the invention may depend on the nature of the particulate material being stabilised and the way in which it is to be administered to a subject. For example, if the particulate material is to be administered intravenously and is required to remain in circulation for some time, the stabiliser may need to be a steric stabiliser as herein described.

If the particulate material is to be administered orally and needs to remain stable in the high acid conditions of the stomach, the stabiliser may also need to be a steric stabiliser as herein described, for example a steric stabiliser comprising poly acrylamide.

By the particulate material being "dispersed throughout" a liquid carrier is meant that the particulate material presents as a dispersed phase throughout the liquid carrier which itself, relative to the particulate material, presents as a continuous liquid medium or phase. In other words, the composition might be described as comprising a suspension or dispersion of the particulate material throughout the liquid carrier.

As used herein, the term "liquid" in the context of the liquid carrier is intended to mean a vehicle in which the particulate material is dispersed throughout and which is in a liquid state at least at the temperature of intended use in the methods of the invention. Typically, a liquid carrier will be considered to be in a "liquid" state if, in the absence of a stabiliser, particulate material dispersed throughout the carrier can flocculate or settle out from the carrier to form sediment. In other words, if the particulate material can move relatively freely in the vehicle, then it is considered "liquid".

The liquid carrier may be made up of one or more different liquids. Suitable pharmacologically acceptable liquid carriers are described in Martin, Remington's Pharmaceutical Sciences, $18^{th}$ Ed., Mack Publishing Co., Easton, Pa., (1990). Generally, the liquid carrier will be an aqueous liquid carrier. Water or soluble saline solutions and aqueous dextrose and glycerol solutions are preferably employed as liquid carriers, particularly for injectable solutions.

The dispersion may comprise one or more pharmacologically acceptable additives known to those in the art. For example, the liquid carrier may comprise one or more additives such as wetting agents, de-foaming agents, surfactants, buffers, electrolytes, and preservatives.

The particular nature of the liquid carrier and any additive therein (if present) will in part depend upon the intended application of the composition. Those skilled in the art will be able to select a suitable liquid carrier and additive (if present) for the intended application of the dispersion.

It should also be understood that the particulate material and/or (steric) stabiliser may also be coupled to a ligand to effect more specific targeting to a tumour. This will not necessarily be applicable in every situation but, to the extent that an appropriate target molecule exists for a given tumour, this may provide additional useful specificity.

Although the general notion of targeted therapy is not new, to date the success of targeted therapy has been limited by virtue of meeting the criteria which have been required of a potential target molecule, these being:
 (i) cell surface location
 (ii) high cell surface molecule density
 (iii) lack of internalisation of the molecule; and
 (iv) lack of appreciable antigen shedding from the cell surface.

Limitations do exist in terms of the identification of such molecules, in particular antigens which are also ideally tumour-specific. However, to the extent that such targets are known for a given situation, they may be usefully exploited.

To this end, reference to a "ligand" should be understood as a reference to any molecule having specificity (not necessarily exclusive specificity, although this is preferable) and binding affinity for a tumour molecule. Examples of ligands include immunointeractive molecules, peptidomimetic agents, lanthamide metals (which interact with RNA species), enzymatic substrates (which interact with cell death-related enzymes) and putrescine (which interacts with tissue transglutaminase). In one embodiment, the ligand is an immunointeractive molecule. Although a preferred immunointeractive molecule is an immunoglobulin molecule, the present invention extends to other immunointeractive molecules such as antibody fragments, single chain antibodies, deimmunized antibodies including humanized antibodies and T-cell associated antigen-binding molecules (TABMs). Most preferably, the immunointeractive molecule is an antibody such as a polyclonal or monoclonal antibody. It should be understood that the subject ligand may be linked, bound or otherwise associated to any other proteinaceous or non-proteinaceous molecule or cell.

The ligand is "directed to" the tumour molecule. It should be understood that the ligand may not necessarily exhibit complete exclusivity, although this is preferable. For example, antibodies are known to sometimes crossreact with other antigens. An antigenic determinant or epitope includes that part of the molecule to which an immune response can be directed. The antigenic determinant or epitope may be a B-cell epitope or where appropriate a T-cell receptor binding molecule.

The present invention may also be designed such that a ligand is directed to one or more tumour molecules. Accordingly, the present invention may be designed to administer two or more ligands directed to different targets, for example as a means of increasing the dose of cellular toxin which is delivered to a population of neoplastic cells. It also provides a convenient means of simultaneously delivering two different toxins.

Where used, the ligand may be directly bound to the particulate material or indirectly bound to the particulate material by forming part of the steric stabiliser. For example, the ligand may be bound to the steric stabiliser.

Figure 15:
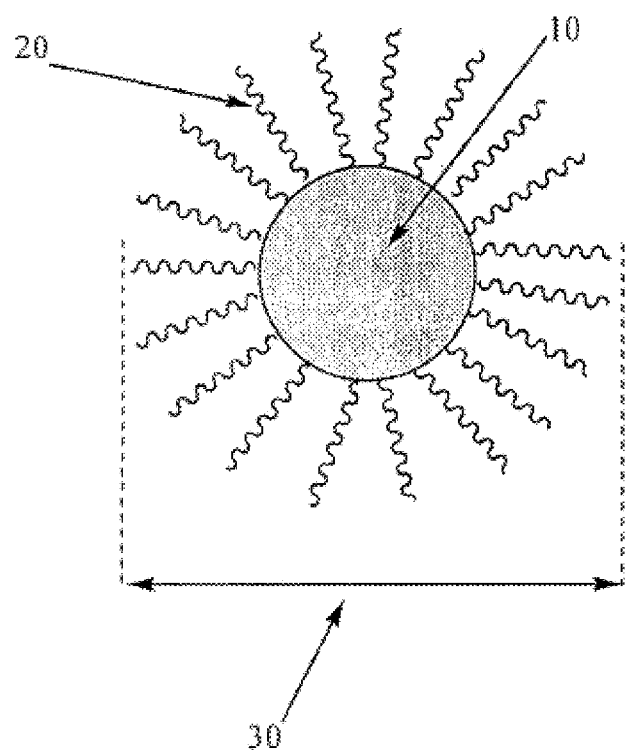
FIG. 15 shows a schematic illustration showing the hydrodynamic volume of a stabilised particulate material.

Those skilled in the art will appreciate that the dispersed particulate material used in accordance with the invention will present a hydrodynamic diameter within the liquid carrier. The hydrodynamic diameter is the distance or size that is derived from the particulate material per se and the steric stabilisers associated with the particulate material. This can be more clearly explained with reference to FIG. 15 where the particulate material per se (10) is dispersed within a carrier liquid (not shown) by (steric) stabilisers (20). The hydrodynamic diameter (30) of the dispersed particulate material can therefore be seen to represent the diameter afforded by a combination of the particulate material and the (steric) stabilisers. Where the dispersed particulate material does not have a symmetrical shape, the hydrodynamic diameter will be considered to be that of the largest hydrodynamic diameter presented by the dispersed particulate material.

Without wishing to be limited by theory, it is believed that the hydrodynamic diameter of the dispersed particulate material may also play a role in facilitating deep penetration of the particulate material within tumours.

In one embodiment, the hydrodynamic diameter of the dispersed particulate material is less than about 500 nm, is less than about 350 nm, less than about 250 nm, less than about 100 nm, less than about 50 nm, less than about 25 nm or less than about 15 nm.

In a further embodiment, the hydrodynamic diameter of the dispersed particulate material is about: 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm.

For avoidance of any doubt, reference herein to the "the hydrodynamic diameter" of the dispersed particulate material is intended to denote an average diameter (at least about 50 number %) of the dispersed particulate material. The hydrodynamic diameter of dispersed particulate material is determined herein by Hydrodynamic Chromatography (HDC, PL-PSDA (Polymer Laboratories)).

Reference herein to a "subject" should be understood to encompass humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). Preferably, the mammal is a human.

It should be understood that the term "treatment" does not necessarily imply that a subject is treated until total recovery. Accordingly, treatment includes reducing the severity of an existing condition, amelioration of the symptoms of a particular condition or preventing or otherwise reducing the risk of developing a particular condition.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

In a related aspect of the present invention, the subject undergoing treatment may be any human or animal in need of therapeutic treatment. In this regard, reference herein to "treatment" is to be considered in its broadest context. The term "treatment" does not necessarily imply that a mammal is treated until total recovery. Accordingly, treatment includes amelioration of the symptoms of a particular condition or preventing or otherwise reducing the risk of developing a particular condition. "Treatment" may also reduce the severity of an existing condition.

Administration of the particulate material and cellular toxin, in the form of pharmaceutical compositions, may be performed by any convenient means. The pharmaceutical composition is contemplated to exhibit therapeutic activity when administered in an amount which depends on the particular case. The variation depends, for example, on the human or animal and the particular agent, particulate material and toxin selected for use. A broad range of doses may be applicable. Dosage regimes may be adjusted to provide the optimum therapeutic response.

Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip patch and implant. The particle may also be administered directly to the tumour.

The compositions in accordance with the invention comprise pharmacologically acceptable particulate material dispersed throughout a pharmacologically acceptable liquid carrier. By "pharmacologically acceptable" is meant that the particulate material, liquid carrier, or other constituent of the composition (e.g. the steric stabiliser) is suitable for administration to a subject in their own right. In other words, administration of the particulate material, liquid carrier or other constituent of the composition to a subject will not result in unacceptable toxicity, including allergenic responses and disease states.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Having said this, those skilled in the art will appreciate that the suitability of a composition for administration to a subject and whether or not a given particulate material or liquid carrier would be considered pharmacologically acceptable, will to some extent depend upon the mode of administration selected. Thus, the mode of administration may need to be considered when evaluating whether a given composition is suitable for administration to a subject or pharmacologically acceptable.

The pharmaceutical forms are preferably suitable for injectable use and include sterile aqueous solutions (where water soluble) or dispersions and sterile powders for the extemporaneous preparation of sterile injectable solutions or dispersion. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

In one embodiment, the stabilised particulate material and cellular toxin may be formulated in a single formulation. In an alternative embodiment, said stabilised particulate material and cellular toxin are formulated in two separate formulations.

The present invention is further described by reference to the following non-limiting examples.

Example 1

Steric Stabilization of Iron Oxide Nanoparticles in Aqueous Dispersion Using poly(monoacryloxyethyl phosphate)$_{10}$-block-poly(acrylamide)$_{20}$ Macro Raft Agent

Part (a): Preparation of Diluted Aqueous Ferrofluid Stable in Acidic Medium Magnetite nanoparticles were produced following the method of Massart (*Preparation of aqueous magnetic liquids in alkaline and acidic media*. IEEE Transactions on Magnetics, 1981. MAG-17(2): p. 1247-1248). In a typical reaction, 80 ml of 1M FeCl$_3$.6H$_2$O in 2M HCl and 40 ml of 1M FeCl$_2$.4H$_2$O in 2M HCl were mixed in a 2 Liter beaker and the mixture diluted to 1.2 Liter with MQ-water. 250 ml of NH$_4$OH (28% (w/w)) was then quickly added to the beaker and the mixture vigorously stirred for 30 minutes. Upon adding NH$_4$OH, the colour of the mixture immediately turned from orange to black suggesting the formation of magnetite. Magnetite was then oxidized in acidic medium to maghemite by heating at 90° C. with iron nitrate for about an hour. The colour of the suspension changed from black to reddish brown. Maghemite particles were then magnetically decanted, washed with acetone and finally peptized in water yielding a stable dispersion (5 wt %). The pH of the dispersion was about 1.5-2.

Part (b): Preparation of a poly(monoacryloxyethyl phosphate)10-block-poly(acrylamide)20 Macro-RAFT Agent Using: 2-{[(dodecylsulfanyl)carbonothioyl]sulfanyl} Succinic Acid A solution of 2-{[(dodecylsulfanyl)carbonothioyl]sulfanyl} succinic acid (0.81 g, 2.0 mmol), 4,4'-azobis(4-cyanovaleric acid) (0.09 g, 0.3 mmol), acrylamide (2.87 g, 40.3 mmol) in dioxane (15 g) and water (15 g) was prepared in a 100 mL round bottom flask. This was stirred magnetically and sparged with nitrogen for 15 minutes. The flask was then heated at 70° C. for 4 hrs. At the end of this period, monoacryloxyethyl phosphate (3.98 g, 20 mmol) and 4,4'-azobis(4-cyanovaleric acid) (0.09 g, 0.3 mmol) were added to the flask. The mixture was deoxygenated and heating was continued at 80° C. for a further 12 hours. The copolymer solution had 23.6% solids. The copolymer solution was then diluted with MQ water to 0.7 wt % and the pH adjusted to 5 using 0.1M NaOH.

Part (c): Preparation of Sterically Stabilized Iron Oxide Nanoparticles from the Aqueous Ferrofluid of Example 1, Part (a) and the Macro-RAFT Agent of Example 1, Part (b)

Nanoparticle dispersion prepared in example 1 part (a) (27 g) was diluted with MQ water (200 g) to yield a 2 wt % dispersion of the nanoparticles. The pH of this nanoparticle dispersion was then raised to 5 using 0.1 M sodium hydroxide. The 2 wt % dispersion of the iron oxide dispersion was then added to the macro-RAFT copolymer solution from example 1, part (b) (100 g). The mixture was stirred vigorously with an overhead stirrer for 45 minutes before the pH was adjusted to pH 7 using sodium hydroxide solution. The mixture was then left to stir vigorously for another 2 hours at room temperature. The nanoparticle dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solids loading in the aqueous ferrofluid dispersion to about 70 wt %. The resulting aqueous ferrofluid was found to be stable in 60% ammonium nitrate solution.

Example 2

Steric Stabilization of Iron Oxide Nanoparticles in Aqueous Dispersion Using 95% poly(monoacryloxyethyl phosphate)10-block-poly(ethylene oxide) 17 Macro Raft Agent and 5% poly(monoacryloxyethyl phosphate)10-block-poly(acrylamide)25 Macro Raft Agent

Part (a): Esterification of poly(ethylene glycol) Monomethyl Ether with 2-{[(butylsulfanyl)carbonothioyl]sulfanyl}propanoic Acid MethoxyPEG (Mn~798) was warmed and stirred to liquefy and homogenize it, and 19.95 g (25.0 mmol) was then weighed into a 250 mL 3-necked round bottom flask, and then allowed to solidify. 2-{[(butylsulfanyl)carbonothioyl]sulfanyl}propanoic acid (6.96 g, 29.3 mmol) and 4-dimethylaminopyridine (360 mg, 2.9 mmol) were added to the flask, a magnetic stirbar was introduced, and the flask was purged with nitrogen. Dry dichloromethane (75 mL) was added and the mixture was stirred until the solids had all dissolved. The flask was then cooled in an ice bath and a solution of N,N'-dicyclohexylcarbodiimide (6.03 g, 29.3 mmol) in dry dichloromethane (25 mL) was then added dropwise over 1 h. The reaction was stirred in the ice-bath for a further 10 min, then at room temperature for 24 h. The resulting yellow slurry was diluted with 1:1 hexane-ether (100 mL) and filtered through a sintered glass funnel. The filter residue was washed with further small portions of 1:1 hexane-ether until it was white, and the combined filtrates were evaporated to give a cloudy and gritty dull orange oil. The crude product was dissolve in dichloromethane (75 mL) and stirred with solid oxalic acid (4 g) for 1 h, then diluted with hexane (70 mL) and allowed to settle, producing a flocculent white precipitate. The mixture was filtered and evaporated, and the crude oil was dissolved in 2:1 hexane-dichloromethane (150 mL) and passed through a plug of alumina (40 g). Elution with further 2:1 hexane-dichloromethane was continued until the eluate was colourless. The combined eluates were dried with sodium sulphate, filtered, and evaporated to give a clear pale orange oil, 24.69 g, 97%.

Part (b): Preparation of a poly(ethylene oxide)17-block-poly(monoacryloxyethyl phosphate)10 Macro-Raft Agent Based on the Macro-Raft of Example 2 Part (a)

A solution of RAFT-PEO from example 2 part (a) (3.60 g, 3.5 mmol), 4,4'-azobis(4-cyanovaleric acid) (0.20 g, 0.7 mmol), monoacryloxyethyl phosphate (6.89 g, 35 mmol) in dioxane (45 g) and water (22.5 g) was prepared in a 250 mL round bottom flask. This was stirred magnetically and sparged with nitrogen for 15 minutes and the reaction was carried out at 70° C. for 12 hours. The copolymer solution had 15.1% solids. The copolymer solution was then diluted with MQ water to 0.7 wt % and the pH adjusted to 5 using 0.1M NaOH.

Part (c): Preparation of a poly(monoacryloxyethyl phosphate)10-block-poly(acrylamide)20 Macro-RAFT Agent Using 2-{[(butylsulfanyl)carbonothioyl]sulfanyl}propanoic Acid A solution of 2-{[(butylsulfanyl)carbonothioyl]sulfanyl}propanoic acid (3.2 g, 13.6 mmol), 4,4'-azobis(4-cyanovaleric acid) (0.19 g, 0.7 mmol), acrylamide (19.27 g, 271.1 mmol) in dioxane (45 g) and water (22.5 g) was prepared in a 250 mL round bottom flask. This was stirred magnetically and sparged with nitrogen for 15 minutes. The flask was then placed in a 70° C. for 4 hrs. The homopolymer solution had 32.0% solids. 15 g of the obtained homopolymer solution, monoacryloxyethyl phosphate (4.50 g, 22.9 mmol) and 4,4'-azobis(4-cyanovaleric acid) (0.04 g, 0.2 mmol) were added to a 100 mL round bottom flask. The mixture was deoxygenated by nitrogen sparging for 15 minute and the flask stirred in a 70° C. oil bath for 12 hours. The copolymer solution, which contained 40.4% solids, was then diluted with MQ water to 1.2 wt %. The pH of the diluted copolymer solution was adjusted to 5 with 0.1M NaOH.

Part (d): Preparation of Sterically Stabilized Iron Oxide Nanoparticles from the Aqueous Ferrofluid of Example 1 Part (a) and a 95:5 Blend of the Macro-RAFT Agent of Example 2 Part (b) and the Macro-RAFT Agent of Example 2 Part (c)

A nanoparticle dispersion prepared according to example 1, part (a) was diluted with MQ water to yield a 2 wt % dispersion of the nanoparticles. The pH of this prepared nanoparticle dispersion was then raised to 5. A blend of macro-RAFT which consist of 50 g of a 0.7 wt % solution of example 2 part (b) and 50 g of 1.2 wt % solution of example 2 part (c) were mixed together and the pH adjusted to 5 using 0.1M NaOH. The 2 wt % dispersion of iron oxide maintained at the same pH was then added to the macro-RAFT blend. The mixture was vigorously stirred for 2 hours at room temperature before the pH was adjusted to 7.0. The mixture was then left stirring for another 3 hours. At this pH the copolymer remained partially neutralized while the nanoparticles were sufficiently above their point of zero charge to also be stable. The dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solids loading in the aqueous ferrofluid dispersion to about 70 wt %. The resulting aqueous ferrofluid was found to be stable in phosphate buffered saline solution.

Part (e): Modification of Stabilisers for Iron Oxide Particles of Example 2 Part (d)

Into coated nanoparticles prepared from example 2 part (d) (7.8 g), N-hydroxysuccinimide (NHS, 14.4 mg) and then 1-Ethyl-3-(3-Dimethylamino-propyl)carbodiimide (EDAC, 20 mg) were added, mixed by shaking and allowed to react for 2 hours at room temperature. A solution of diamine (90 mg of 2,2'-(Ethylenedioxy)bis-(ethylamine) in 1 ml of water) was then added to the reaction mixture and allowed to react for a further 3.5 hours. The solution was then dialysed against excess water with numerous changes, to remove free EDAC and the reaction by-products.

Example 3

Steric Stabilization of Iron Oxide Nanoparticles in Aqueous Dispersion Using the Ferrofluid of Example 1 Part (a) and the poly(monoacryloxyethyl phosphate)$_{10}$-block-poly(ethylene oxide)17 Macro Raft Agent of Example 2 Part (b)

Nanoparticle dispersion (8.0 g) prepared according to example 1 part (a) was diluted with 50 g of MQ water to yield a 0.5 wt % dispersion of the nanoparticles. The pH of this prepared nanoparticle dispersion was then raised to 5. The 0.5 wt % dispersion of iron oxide maintained at the same pH was then added to the 50 g of macro-RAFT agent from example 2 part (b). The mixture was vigorously stirred for 2 hours at room temperature before the pH was adjusted to 7.0. The mixture was then left stirring for another 3 hours. At this pH the copolymer remained partially neutralized while the nanoparticles were sufficiently above their point of zero charge to also be stable. The dispersion was then dialysed to remove salts, residual solvents, unwanted low molecular weight reaction side products and unbound polymer. The final solids of the dispersion was 0.74%.

Example 4

Steric Stabilization of Iron Oxide Nanoparticles of the Aqueous Ferrofluid of Example 1 Part (a) Using the poly(monoacryloxyethyl phosphate)$_{10}$-block-poly(acrylamide)$_{20}$ Macro-Raft Agent of Example 2 Part (c)

Nanoparticle dispersion prepared in example 1 part (a) (6.19 g) was diluted with MQ water (100 g) to yield a 1 wt % dispersion of the nanoparticles. The pH of this nanoparticle dispersion was then raised to 5 using 0.1 M sodium hydroxide. The 2 wt % dispersion of the iron oxide dispersion was then added to the macro-RAFT copolymer solution from example 2 part (c) (50 g). The mixture was stirred vigorously with an overhead stirrer 2 hours before the pH was adjusted to pH 7 using sodium hydroxide solution. The mixture was then left to stir vigorously for another 12 hours at room temperature. The nanoparticle dispersion was then dialysed to remove salts, residual solvents, unwanted low molecular weight reaction side products and unbound polymer. The solid content of the final dispersion is 0.71%.

Example 5

Steric Stabilization of Iron Oxide Nanoparticles in Aqueous Dispersion from the Aqueous Ferrofluid of Example 1 Part (a) Using 100% Amine Modified poly(monoacryloxyethyl phosphate)$_{10}$-block-poly(acrylamide)$_{20}$ Part (a): Preparation of Amine Modified poly(monoacryloxyethyl phosphate)$_{10}$-block-poly(acrylamide)$_{20}$ Macro-RAFT Agent from the Macro-RAFT Agent of Example 2 Part (c)

N-hydroxy succinimide 98% (0.64 g), 2, 2'-(Ethylenedioxy)bis-(ethylamine), 98% (0.54 g) was added to 30.0 g of poly(monoacryloxyethyl phosphate)$_{10}$-block-poly(acrylamide)$_{20}$ block copolymer of example 2 part (c) at pH 6.25 in a 100 mL glass bottle. The bottle was sealed with parafilm and placed on a roller for mixing for 2 hours. After 2 hours, the mixture had a pH of 8.12 to yield the NHS-activated carboxyl groups which are reactive towards primary amine. 1.26 g of N-(3-Dimethylaminopropyl)-N'-ethylcarbodiimide hydrochloride was then added to the mixture, which was left on the roller for further 12 hours. The excess N-(3-Dimethylaminopropyl)-N'-ethylcarbodiimide hydrochloride was removed by dialysis.

Part (b): Preparation of Sterically Stabilized Iron Oxide Nanoparticles from the Aqueous Ferrofluid of Example 1, Part (a) and the Macro-RAFT Agent of Example 5, Part (a)

Nanoparticle dispersion prepared in example 1 part (a) (8.38 g) was diluted with MQ water (50 g) to yield a 0.5 wt % dispersion of the nanoparticles. The pH of this nanoparticle dispersion was then raised to 5 using 0.1 M sodium hydroxide. The 0.5 wt % dispersion of the iron oxide nanoparticles was then added to the macro-RAFT copolymer solution, from example 5 part (a) (22.6 g) and 50 g of MQ water. The mixture was stirred vigorously with an overhead stirrer for 2 hours before the pH was adjusted to pH 7 using sodium hydroxide solution. The mixture was then left to stir vigorously for another 10 hours at room temperature. The nanoparticle dispersion was then dialysed to remove salts, residual solvents, unwanted low molecular weight reaction side products and unbound polymer. The solids content of the dialysed aqueous ferrofluid dispersion was 0.36%.

Example 6

Steric Stabilization of Iron Oxide Nanoparticles in Aqueous Dispersion Using 95% poly(monoacryloxyethyl phosphate)$_{10}$-block-poly(acrylamide)$_{20}$ Macro-Raft Agent of Example 2 Part (c) and 5% Amine Modified poly(monoacryloxyethyl phosphate)$_{10}$-block-poly(acrylamide)$_{20}$ of Example 5 Part (a)

Nanoparticle dispersion prepared in example 1 part (a) (8.09 g) was diluted with MQ water (50 g) to yield a 0.5 wt % dispersion of the nanoparticles. The pH of this nanoparticle dispersion was then raised to 5 using 0.1 M sodium hydroxide. The 0.5 wt % dispersion of the iron oxide dispersion was then added to the macro-RAFT copolymer solution which was pH 5.0 from example 5 part (a) (1.7 g), example 2 part (c) (1.0 g) and 50 g of MQ water. The mixture was stirred vigorously with an overhead stirrer for 2 hours before the pH was adjusted to pH 7 using sodium hydroxide solution. The mixture was then left to stir vigorously for another 3 hours at room temperature. The nanoparticle dispersion was then dialysed to remove salts, residual solvents, unwanted low molecular weight reaction side products and unbound polymer. The solids content of the dialysed aqueous ferrofluid dispersion is 0.53%.

Example 7

Steric Stabilization of Iron Oxide Nanoparticles in Aqueous Dispersion Using poly(monoacryloxyethyl phosphate)$_{10}$-block-poly(acrylamide)$_{60}$ Macro Raft Agent Part (a): Preparation of Diluted Aqueous Ferrofluid Stable in Acidic Medium Magnetite nanoparticles were produced following the method of Massart (*Preparation of aqueous magnetic liquids in alkaline and acidic media*. IEEE Transactions on Magnetics, 1981. MAG-17(2): p. 1247-1248). An aqueous mixture of ferric and ferrous chlorides was added to ammonia solution. The resulting precipitate was isolated by centrifugation then oxidised to maghemite by mixing with iron nitrate solution and heating. The precipitate was then washed in 2 molar nitric acid then finally peptised by water to form a dilute aqueous ferrofluid of approximately 5 wt % solids.

Part (b): Preparation of a poly(monoacryloxyethyl phosphate)$_{10}$-block-poly(acrylamide)60 Macro-RAFT Agent Using 2-{[(butylsulfanyl)carbonothioyl]sulfanyl} propanoic Acid A solution of 2-{[(butylsulfanyl)carbonothioyl]sulfanyl} propanoic acid (0.26 g, 1.1 mmol), 4,4'-azobis(4-cyanovaleric acid) (0.06 g, 0.2 mmol), acrylamide (4.73 g, 66 mmol) in dioxane (10 g) and water (10 g) was prepared in a 100 mL round bottom flask. This was stirred magnetically and sparged with nitrogen for 15 minutes. The flask was then heated at 70° C. for 4 hrs. At the end of this period, monoacryloxyethyl phosphate (2.17 g, 11.1 mmol) and 4,4'-azobis(4-cyanovaleric acid) (0.06 g, 0.2 mmol) were added to the flask. The mixture was deoxygenated and heating was continued at 80° C. for a further 12 hours. The copolymer solution had 24% solids. The copolymer solution was then diluted with MQ water to 0.7 wt % and the pH adjusted to 5 using 0.1M NaOH.

Part (c): Preparation of Sterically Stabilized Iron Oxide Nanoparticles from the Aqueous Ferrofluid of Part (a) and the Macro-RAFT Agent of Example 7 Part (b)

Nanoparticle dispersion prepared in example 7 part (a) (40 g) was diluted with MQ water (200 g) to yield a 1 wt % dispersion of the nanoparticles. The pH of this nanoparticle dispersion was then raised to 5 using 0.1 M sodium hydroxide. The 1 wt % dispersion of the iron oxide dispersion was then added to the macro-RAFT copolymer solution from part (b) (200 g). The mixture was stirred vigorously with an overhead stirrer for 45 minutes before the pH was adjusted to pH 7 using sodium hydroxide solution. The mixture was then left to stir vigorously for another 2 hours at room temperature. The nanoparticle dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solids loading in the aqueous ferrofluid dispersion to about 70 wt %.

Example 8

Steric Stabilization of Sigma Ludox as 30 Silica Particles Using 95% poly[2-(dimethylamino)ethyl methacrylate]$_{10}$-block-poly(ethylene oxide)$_{17}$ Macro Raft Agent and 5% poly(2-(dimethylamino)ethyl methacrylate)$_{10}$-block-poly(acrylamide)$_{25}$ Macro Raft Agent Part (a): Preparation of a poly[2-(dimethylamino) ethyl methacrylate]10-block-poly(ethylene oxide)17 Macro-RAFT Agent Based on 2-{[butylsulfanyl) carbonothioyl]-sulfanyl}propanoic Acid A solution of RAFT-PEO from example 2 part (a) (1.38 g, 1.4 mmol), 4,4'-azobis(4-cyanovaleric acid) (0.08 g, 0.3 mmol), 2-(Dimethylamino)ethyl methacrylate (2.13 g, 13.6 mmol) in dioxane (10 g) and water (5 g) was prepared in a 100 mL round bottom flask. This was stirred magnetically and sparged with nitrogen for 15 minutes and the reaction was carried out at 70° C. for a 12 hours. The copolymer solution had 18.4% solids.

Part (b): Selective Quaternization of a poly[2-(dimethylamino)ethyl methacrylate]10-block-poly(ethylene oxide)17 Macro-RAFT Agent Based on 2-{[butylsulfanyl)carbonothioyl]-sulfanyl}propanoic Acid Example 8 part (a), 16.5 g was diluted with MQ water (17 g) and methyl iodide (0.7 g) added. The mixture was stirred at room temperature for 1 hour before being partially dried using a rotary evaporator. The dried samples were then placed in the vacuum oven to dry the macro raft agent which yielded 100% solids.

Part (c): Preparation of a poly(2-(Dimethylamino) ethyl methacrylate)$_{10}$-block-poly(acrylamide)$_{25}$ Macro-RAFT Agent Based on 2-{[butylsulfanyl) carbonothioyl]-sulfanyl}propanoic Acid A solution of 2-{[(butylsulfanyl)carbonothioyl] sulfanyl}propanoic acid (0.6 g, 2.6 mmol), 4,4'-azobis(4-cyanovaleric acid) (0.11 g, 0.4 mmol), acrylamide (4.45 g, 62.7 mmol) in dioxane (18.8 g) and water (10.5 g) was prepared in a 100 mL round bottom flask. This was stirred magnetically and sparged with nitrogen for 15 minutes. The flask was then placed in a 70° C. oil bath for 4 hrs. The homopolymer solution had 32.7% solids. All of the homopolymer solution obtained, 2-(Dimethylamino)ethyl methacrylate (3.94 g, 25.1 mmol) and 4,4'-azobis(4-cyanovaleric acid) (0.088 g, 0.32 mmol) were added to a 100 mL round bottom flask. The mixture was deoxygenated for 15 minute and placed in a 70° C. oil bath for 12 hours. The final solids of copolymer solution was 26.9%.

Part (d): Selective Quaternization of a poly(2-(dimethylamino)ethyl methacrylate)$_{10}$-block-poly(acrylamide)$_{25}$ Macro-RAFT Agent Based on 2-{[butylsulfanyl)carbonothioyl]-sulfanyl}propanoic Acid Example 8 part (c) (19.3 g) was diluted with MQ water (20 g) and methyl iodide (0.78 g) was added. The mixture was stirred at room temperature for 1 hour be partially dried using a rotary evaporator. The partially dried samples was then placed in the vacuum oven to dry the macro raft agent which yield 100% solids.

Part (e): Preparation of Sterically Stabilized Sigma Ludox AS30 Silica Particles Using a 95:5 Blend of the Macro-RAFT Agents of Example 8 Part (b) and Example 8 Part (d)

Ludox AS30 from Sigma Aldrich (2.5 g) was diluted with MQ water (100 g) to yield a 2 wt % dispersion of the nanoparticles and the pH is 9.62. A mixture of example 8 part (b) (0.96 g) and of example 8 part (d) (0.0653 g) was dissolved in MQ water (50 g) and the pH was 7.59. The 2 wt % dispersion was then poured into the mixture of macro-Raft agents. The mixture was vigorously stirred for 5 hours at room temperature. The dispersion was then dialysed to remove salts, residual solvents, unwanted low molecular weight reaction side products and unbound polymer. The solid content of the dialysed silica sol dispersion was 0.69%. The pH of the sample was adjusted to 6.76 with sodium hydroxide solution.

Part (f): Modification of Stabilisers for Silica Particles of Example 8 Part (e) [EP341070A]

Sterically stabilised silica sol particles prepared from example 8 part (e) (60 g), N-hydroxysuccinimide (NHS, 39.4 mg) and then 1-Ethyl-3-(3-Dimethylamino-propyl)carbodiimide (EDAC, 56.2 mg) were added, mixed by shaking and allowed to react for 2 hours at room temperature. 37 mg of 2,2'-(Ethylenedioxy)bis-(ethylamine) was then added to the reaction mixture and allowed to react for a further 12 hours. The solution was then dialysed against excess water with numerous changes, to remove free EDAC and the reaction by-products.

Example 9

Steric Stabilization of Sigma Ludox as40 Silica Sol Using 95% poly[2-(dimethylamino)ethyl methacrylate]$_{10}$-block-poly(ethylene oxide)$_{17}$ Macro Raft Agent and 5% poly(2-(dimethylamino)ethyl methacrylate)$_{10}$-block-poly(acrylamide)$_{25}$ Macro Raft Agent Part (a): Preparation of Sterically Stabilized Sigma Ludox AS30 Silica Particles and a 95:5 Blend of the Macro-RAFT Agents of Example 8 Part (b) and Example 8 Part (d)

Ludox AS40 from Sigma Aldrich (5.0 g) was diluted with MQ water 100 g to yield a 2 wt % dispersion of the nanoparticles and the pH is 9.97. A mixture of macro-RAFT agents, which consisted of example 8 part (b) (1.72 g) and example 8 part (d) (0.13 g) was dissolved in 100 g of MQ water and the pH was 7.95. The 2 wt % dispersion was then poured into the mixture of macro-RAFT agents. The mixture was vigorously stirred for 5 hours at room temperature. The dispersion was then dialysed to remove salts, residual solvents, unwanted low molecular weight reaction side products and unbound polymer. The solid content of the dialysed silica sol dispersion is 1.45%. The pH of sample was 7.65.

Part (b): Modification of Stabilisers of Silica Particles of Example 9 Part (a)

To sterically stabilised silica sol particles prepared in example 9 part (a) (30 g), N-hydroxysuccinimide (NHS, 11.6 mg) and 1-Ethyl-3-(3-Dimethylamino-propyl)carbodiimide (EDAC, 16.6 mg) were added, mixed by shaking and allowed to react for 2 hours at room temperature. 2,2'-(Ethylenedioxy)bis-(ethylamine) (45.1 mg) was then added to the reaction mixture and allowed to react for a further 12 hours. The solution was then dialysed against excess water with numerous changes, to remove free EDAC and the reaction by-products.

Example 10

Steric Stabilization of 130 nm Silica Particles Using Poly(2-(dimethylamino)ethyl methacrylate)$_{10}$-block-poly(acrylamide)$_{25}$ Macro Raft Agent Part (a): Silica Particles were Prepared Using the Methods of Costa et al (Carlos A. R. Costa, Carlos A. P. Leite, and Fernando Galembeck *J. Phys. Chem. B,* 2003, 107 (20), 4747-4755.) to obtain 130 nm diameter silica particles at 0.18% solids in water.

Part (b): Steric Stabilization of the 130 nm Diameter Silica Particles of Example 10 Part (a) Using the Macro-RAFT Agent of Example 8 Part (d)

Silica particle dispersion of example 10 part (a) (11.15 g) was diluted with MQ water (20 g) to yield a 0.1 wt % dispersion of the nanoparticles with a pH of 9.26. Macro-RAFT agent of example 8 part (d) (0.023 g) was dissolved in 25 g of MQ water (25 g) to yield a solution of pH 5.80. The silica dispersion and the macro-RAFT solution were then blended and vigorously stirred for 5 hours at room temperature. The dispersion was then centrifuged to remove salts, residual solvents, unwanted low molecular weight reaction side products and unbound polymer. The solid content of the sterically stabilised silica dispersion is 0.81%.

Example 11

Steric Stabilization of the 130 nm Diameter Silica Particles of Example 10 Part (a) Using the "Grow From" Approach The silica particles of example 10 part (a) were RAFT functionalised using 6-(Triethoxysilyl)hexyl 2-(((Methylthio)carbonothioyl)-2-phenylacetate and polymer chains comprising poly methoxy-PEG acrylate (Aldrich 454 g/mol) were grown from the surface of the particles according to the methods of Ohno et al. (Kohji Ohno, Ying Ma, Yun Huang, Chizuru Mori, Yoshikazu Yahata, Yoshinobu Tsujii, Thomas Maschmeyer, John Moraes, and Sébastien Perrier *Macromolecules,* 2011, 44 (22), pp 8944-8953.) The molecular weight obtained for each anchored chain was approximately 56,000 g/mol. The final particles were obtained in water at a solids content of 10 mg/mL and the particle size was 258 nm, as measured by DLS.

Example 12

Steric Stabilization of 10-15 nm Gold Nanoparticles in Aqueous Dispersion Using 95% poly(ethylene oxide)$_{17}$ Macro Raft Agent and 5% poly(acrylamide)$_{20}$ Macro Raft Agent Part (a): Synthesis of 10-15 nm Citrate Stabilized Gold Nanoparticles Stable in Aqueous Medium Citrate-stabilized gold nanoparticles (10-15 nm) were prepared using Frens method (Frens, G. *Nat. Phys. Sci.* 1973, 241, 20-2.) Briefly, all glassware was first washed with an aqua regia solution (25 vol % concentrated nitric acid and 75 vol % concentrated hydrochloric acid), then rinsed with Milli-Q water several times, and dried. 100 ml of an aqueous solution containing tertrachloroaureic(III) acid trihydrate (0.01 g, 0.025 mmol) was refluxed in a 500 mL 3-necked round bottom flask. 2 ml solution of trisodium citrate dihydrate (0.02 g, 0.068 mmol) was added to it. The solution was heated to boiling point vigorous stirring. Boiling and vigorous stirring was maintained for 30 min. A progressive change of colour from yellow to wine red was observed. The solution was cooled down, dialysed to get rid of excess sodium citrate and stored in at 5° C. The nanoparticle concentration in the dispersion was 50 ppm.

Part (b): Preparation of a poly(acrylamide)$_{20}$ Macro-RAFT Agent Using: 2-{[(butylsulfanyl)carbonothioyl]sulfanyl}propanoic Acid A solution of 2-{[(butylsulfanyl)carbonothioyl]sulfanyl} propanoic acid (0.71 g, 3.0 mmol), 4,4'-azobis(4-cyanovaleric acid) (0.04 g, 0.15 mmol), acrylamide (4.28 g, 60.2 mmol) in dioxane (7.5 g) and water (7.5 g) was prepared in a 100 mL round bottom flask. This was stirred magnetically and sparged with nitrogen for 15 minutes. The flask was then placed in a 70° C. oil bath with continued stirring for 4 hrs. The polymer solution had 25.17% solids.

Part (c): Preparation of Sterically Stabilized 10-15 nm Gold Nanoparticles from the Citrate Stabilised Gold Nanoparticles of Example 12 Part (a) and a 95:5 Blend of the Macro-RAFT Agent of Example 2 Part (a) and the Macro-RAFT Agent of Example 12 Part (b)

100 ml gold nanoparticle dispersion (50 ppm) of example 12 part (a) was transferred to a 250 ml round bottom flask. A 10 ml solution containing 0.012 g of the macro-RAFT agent of example 2 part (a) and 0.15 g the macro-RAFT agent of example 12 part (b) was then added. The mixture was stirred vigorously with a magnetic stirrer bar for 2 hours at room temperature and then dialysed to remove salts, residual solvents, unwanted low molecular weight reaction side products and unbound polymer. The purified nanoparticle dispersion was at a concentration of 50 ppm and was stored in the fridge at 5° C. The resulting aqueous nanoparticle dispersion was found to be stable in phosphate buffer saline solution, Part (d): Modification of Stabilisers for Gold Nanoparticles of Example 12 Part (c)

Into coated nanoparticles prepared from example 12 part (c) (100 ml), N-hydroxysuccinimide (NHS, 4 mg) and then 1-Ethyl-3-(3-Dimethylamino-propyl)carbodiimide (EDAC, 4.1 mg) were added, mixed by shaking and allowed to react for 2 hours at room temperature. A solution of diamine (21 mg of 2,2'-(Ethylenedioxy)bis-(ethylamine) in 2 ml of water) was then added to the reaction mixture and allowed to react for a further 3.5 hours. The solution was then dialysed against excess water with numerous changes, to remove free EDAC and the reaction by-products.

Example 13

Steric Stabilization of 3-8 nm Gold Nanoparticles Dispersed in Aqueous Medium Using Thiol Modified poly(acrylamide)$_{20}$ Part (a): Thiol Modification of poly(acrylamide)$_{20}$ Macro-RAFT Agent of Part Example 12 Part (b) Using Isopropyl Amine A solution of the poly(acrylamide)$_{20}$ macro-RAFT agent of example 12 part (b) (1 g, 0.6 mmol), isopropyl amine (1.77 g, 30 mmol) in dioxane (7.5 g) and water (7.5 g) was prepared in a 100 mL round bottom flask. This was stirred magnetically and sparged with nitrogen for 15 minutes, then allowed to react for a 24 hours at 25° C. At the end of this period, the polymer was precipitated in diethyl ether (50 ml). The precipitates were separated from the reaction mixture by filtration and dried under vacuum using a rotary evaporator. The dried thiol terminated poly(acrylamide)$_{20}$ was sparged with nitrogen for 15 minutes and stored in an airtight container at 20° C.

Part (b): Preparation of Sterically Stabilized 3-8 nm Gold Nanoparticles in Aqueous Dispersion Using Thiol Modified poly(acrylamide)$_{20}$ of Example 13 Part (a)

Milli-Q water (250 mL) was refluxed in a 500 mL 3-necked round bottom flask. 25 mL of a aqueous solution containing tertrachloroaureic(III) acid trihydrate (0.0571 g, 0.1444 mmol) was then added and the solution heated to boiling. Then, a solution in water (25 mL) of trisodium citrate dihydrate (0.5 g, 1.7 mmol) and thiol modified poly(acrylamide)$_{20}$ (0.12 g, 0.0779 mmol) of example 13 part (a) was added and the reaction carried out for 2 hours at 25° C. By the end of this period, the colour of the solution had turned from yellow to wine red. The molar ratio of steric stabilizer to the tertrachloroaureic(III) acid trihydrate in this case is 0.5. The gold nanoparticles were separated from the dispersion by centrifugation at 52,000 g for 30 min. The nanoparticles were redispersed in Milli-Q water at a concentration of 190 ppm. The size of gold nanoparticles obtained from TEM was 3-8 nm.

Example 14

Steric Stabilization of 8-10 nm Gold Nanoparticles Dispersed in Aqueous Medium Using Thiol Modified poly(acrylamide)$_{20}$ of Example 13 Part (a)

Milli-Q water (250 mL) was refluxed in a 500 mL 3-necked round bottom flask. 25 mL of an aqueous solution containing tertrachloroaureic(III) acid trihydrate (0.0652 g, 0.16 mmol) was added and the solution was heated to boiling. Then, a solution in water (25 mL) of trisodium citrate dihydrate (0.5 g, 1.7 mmol) and thiol modified poly(acrylamide)$_{20}$ (0.022 g, 0.0142 mmol) of example 13, part (a) was added and allowed to react for 2 hours at 25° C. By the end of this period, the colour of the solution had turned from yellow to wine red. The molar ratio of steric stabilizer to the tertrachloroaureic(III) acid trihydrate in this case was 0.09. The gold nanoparticles were separated from the dispersion by centrifugation at 52,000 g for 30 min. The nanoparticles were redispersed in Milli-Q water at a concentration of 390 ppm. The size of gold nanoparticles obtained from TEM was 8-10 nm.

Example 15

Steric Stabilization of 30-40 nm Gold Nanoparticles Dispersed in Aqueous Medium Using Thiol Modified poly(acrylamide)$_{20}$ of Example 13 Part (a)

Part (a): Synthesis of 30-40 nm Citrate Stabilized Gold Nanoparticles Stable in Aqueous Medium Citrate-stabilized gold nanoparticles (30-40 nm) were prepared using Frens method (Frens, G. *Nat. Phys. Sci.* 1973, 241, 20-2.) Briefly, all glassware was first washed with an aqua regia solution (25 vol % concentrated nitric acid and 75 vol % concentrated hydrochloric acid), then rinsed with Milli-Q water several times, and dried. 100 ml of an aqueous solution containing tertrachloroaureic(III) acid trihydrate (0.01 g, 0.025 mmol) was refluxed in a 500 mL 3-necked round bottom flask. 1 ml solution of trisodium citrate dihydrate (0.01 g, 0.034 mmol) was then added. The solution was heated to boiling with vigorous stirring. Boiling and vigorous stirring was maintained for 30 min. A progressive change of colour from yellow to wine red was observed. The solution was cooled to ambient, dialysed to get rid of excess sodium citrate and stored at 5° C. The nanoparticle concentration in the dispersion was 50 ppm.

Part (b): Preparation of Sterically Stabilized 30-40 nm Gold Nanoparticles from the Aqueous Gold Nanoparticle Dispersion of Example 15 Part (a) and Thiol Modified poly(acrylamide)$_{20}$ of Example 13 Part (a)

100 ml gold nanoparticle dispersion (50 ppm) of example 15 part (a) was taken in a 250 ml round bottom flask. 10 ml solution of aqueous solution of example 13 part (a) containing thiol modified poly(acrylamide)$_{20}$ (0.0068 g, 0.0044 mmol) was then added. The mixture was stirred vigorously with a magnetic stirrer bar for 2 hours at room temperature and then dialysed to remove salts, residual solvents, unwanted low molecular weight reaction side products and unbound polymer. The purified nanoparticle dispersion was then distilled to increase the solids loading in the aqueous nanoparticle dispersion to 192 ppm. The resulting aqueous nanoparticle dispersion was found to be stable in phosphate buffer saline solution, Example 16

Synthesis of Polystyrene Nanoparticles in Aqueous Dispersion Using Poly(Styrene)$_9$-b-poly(acrylamide)15 Macro Raft Agent Part (a): Preparation of Self Assembled poly(styrene)9-b-poly(acrylamide)15 Macro-RAFT Agent Using: 2-{[(butylsulfanyl)carbonothioyl]sulfanyl}propanoic Acid A solution of 2-{[(butylsulfanyl)carbonothioyl]sulfanyl}propanoic acid (0.80 g, 3.36 mmol), 4,4'-azobis(4-cyanovaleric acid) (0.10 g, 0.36 mmol), acrylamide (3.71 g, 52.06 mmol) in dioxane (6.61 g) and water (4.41 g) was prepared in a 50 mL round bottom flask. This was stirred magnetically and sparged with nitrogen for 10 minutes. The flask was then heated at 70° C. for 5 hrs to produce the clear homopolymer solution. At the end of this period, styrene (3.16 g, 30.3 mmol), 4,4'-azobis(4-cyanovaleric acid) (0.19 g, 0.69 mmol), dioxane (21.15 g) and water (6.14 g) were added to the flask. The mixture was stirred, deoxygenated with nitrogen for 10 minutes. The flask was then immersed back in an oil bath at 70° C. for overnight with constant stirring.

Part (b): Synthesis of Polystyrene Nanoparticles Using the Self Assembled Macro-RAFT Agent Prepared in Example 16 Part (a)

To a clear dispersion of macro-RAFT agent from example 16 part (a) (1.00 g) in a 50 mL round bottom flask on a magnetic stirrer, sodium hydroxide solution (1.94 g of 0.3% solution, 0.15 mmol with water (22.1 g)) was added drop wise. To this mixture styrene (1.109 g, 10.5 mmol) was added and stirred overnight. 4,4'-azobis(4-cyanovaleric acid) (15.5 mg, 0.055 mmol) and sodium hydroxide solution (1.04 g of 3% solution, 0.78 mmol) were added. The flask was stirred for 2 hours, then sealed and subsequently deoxygenated with nitrogen sparging for 10 minutes. The whole flask was immersed in an oil bath with a temperature setting of 80° C. and maintained at that temperature for 5 hours under constant magnetic stirring. The latex contained particles with average diameter of 15 nm by Zetasizer light scattering. The latex was dialysed against milli-Q water to remove impurities.

Example 17

Synthesis of Polystyrene Nanoparticles in Aqueous Dispersion Using Self Assembled poly(styrene)$_9$-b-poly(acrylamide)$_{20}$ Macro Raft Agent of Example 16 Part (a)

Part (a): Further Growth of the Self Assembled Macro-RAFT Agent of Example 16 Part (a) to Form poly(styrene)$_{52}$-b-poly(acrylamide)$_{20}$ Macro-RAFT To a clear dispersion of macro-RAFT agent from example 16 part (a) (1.02 g) in a 25 mL round bottom flask on a magnetic stirrer, sodium hydroxide solution (0.44 g of 3% solution, 0.33 mmol), 4,4'-azobis(4-cyanovaleric acid) (14.1 mg, 0.05 mmol) and water (14.0 g) were added and stirred to dissolved. To this mixture styrene (0.61 g, 5.85 mmol) was added and stirred overnight. The flask was then sealed and subsequently deoxygenated with nitrogen sparging for 10 minutes. The whole flask was immersed in an oil bath with a temperature setting of 70° C. and maintained at that temperature for 6 hours under constant magnetic stirring. A clear dispersion was obtained Part (b): Synthesis of Polystyrene Nanoparticles Using the Macro-RAFT Agent Dispersion Prepared in Example 17 Part (a)

To a clear solution of macro-RAFT agent from example 17 part (a) (6.09 g) in a 50 mL round bottom flask on a magnetic stirrer, sodium hydroxide solution (0.36 g of 3% solution, 0.27 mmol), 4,4'-azobis(4-cyanovaleric acid) (26.6 mg, 0.095 mmol), styrene (0.45 g, 4.37 mmol) and water (8.31 g) were added. The flask was stirred for 5 hours, then sealed and subsequently deoxygenated with nitrogen sparging for 10 minutes. The whole flask was immersed in an oil bath with a temperature setting of 70° C. and maintained at that temperature for overnight under constant magnetic stirring. The latex contained particles with mean diameter of 47 nm by Zetasizer light scattering. The latex was dialysed against milli-Q water to remove impurities.

Example 18

Synthesis of Polystyrene Nanoparticles in Aqueous Dispersion Using poly(acrylamide)$_{20}$ Macro Raft Agent Part (a): Preparation of poly(acrylamide)$_{20}$ macro-RAFT Agent Using: 2-{[(butylsulfanyl)carbonothioyl]sulfanyl}propanoic Acid A solution of 2-{[(butylsulfanyl)carbonothioyl]sulfanyl}propanoic acid (0.73 g, 3.08 mmol), 4,4'-azobis(4-cyanovaleric acid) (0.07 g, 0.3 mmol), acrylamide (4.30 g, 60.5 mmol) in dioxane (15 g) and water (7.5 g) was prepared in a 100 mL round bottom flask. This was stirred magnetically and sparged with nitrogen for 15 minutes. The flask was then heated at 70° C. for 4 hrs to produce the clear homopolymer solution.

Part (b): Synthesis of Polystyrene Nanoparticles Using the Macro-RAFT Agent Prepared in Example 18 Part (a)

A clear solution of macro-RAFT agent from example 18 part (a) (1.05 g), sodium hydroxide (2.07 g of 3% solution, 1.55 mmol) and water (12.16 g) was prepared in a 25 mL round bottom flask, stirring on a magnetic stirrer. To this solution 4,4'-azobis(4-cyanovaleric acid) (13.6 mg, 0.049 mmol), dioxane (1.1 g) and styrene (1.125 g, 10.8 mmol) were added. The mixture was stirred for 2 hours to obtain an emulsion like mixture. The flask was sealed and subsequently deoxygenated with nitrogen sparging for 10 minutes. The whole flask was immersed in an oil bath with a temperature setting of 70° C. and maintained at that temperature for overnight under constant magnetic stirring. The latex contained particles with average diameter of 200 nm by Zetasizer light scattering. The latex was dialysed against milli-Q water to remove impurities.

Example 19

Stabilisation of Iron Oxide Nanoparticles with Dextran from Leuconostoc Mesenteroides (Average Molecular Weight of 9000-11,000, Sigma Aldrich) Coated Particles. (Example 19 is a Comparative Example)

25 ml of 0.5 M FeCl$_2$/4H$_2$O and 25 ml of 1M FeCl$_3$/6H2O were mixed and magnetically stirred in a 500 ml 3 neck round bottom flask. The resulting solution was diluted by adding 100 ml of MQ water and placed in an oil bath at 70° C. Dextran solution (50 ml of 15% solids in water) was added and the solution maintained in the oil bath for 10 minutes. Ammonia solution (30 ml, 28%) was then added and the mixture kept at 70° C. for a further 45 minutes. The reaction product was cooled to room temperature and dialysed against MQ water to remove excess ammonia. The water was changed at least three times. Larger aggregates were removed by magnetic sedimentation. Volume was reduced to about 100 ml by removing water on rotary evaporator. The final dispersion was sonicated at 70% AMP using an ultrasonicator for 10 minutes and at also at 30% AMP for 30 minute.

Example 20

Steric Stabilization of Iron Oxide Nanoparticles of Example 1 Part (a) Using 50% poly(monoacryloxyethyl phosphate)$_{10}$-block-poly(ethylene oxide)$_{17}$ macro raft agent of Example 2 Part (b) and 50% Amine Modified poly(monoacryloxyethyl phosphate)$_{10}$-block-poly(acrylamide)$_{20}$ Macro Raft Agent Part (a): Preparation of Sterically Stabilized Iron Oxide Nanoparticles from the Aqueous Ferrofluid of Example 1 Part (a) and a 50:50 Blend of the Macro-RAFT Agent of Example 2 Part (b) and the Macro-RAFT Agent of Example 2 Part (c)

Aqueous ferrofluid prepared according to example 1, part (a) (8.10 g) was diluted with MQ water (50 g) to yield a 0.5 wt % dispersion of the nanoparticles. The pH of this prepared nanoparticle dispersion was then raised to 5. A blend of macro-RAFT which consist of 50 g of at 5.1 wt % solids, 3.3 wt % of which was the macro-RAFT agent of example 2 part (b) and 1.8 wt % of which was the macro-RAFT agent of example 2 part (c) were mixed together and the pH adjusted to 5 using 0.1M NaOH. The dispersion of iron oxide, maintained at the same pH was then added to the macro-RAFT blend. The mixture was vigorously stirred for 2 hours at room temperature before the pH was adjusted to 7.0. The mixture was then left stirring for another 12 hours. At this pH the copolymer remained partially neutralized while the nanoparticles were sufficiently above their point of zero charge to also be stable. The dispersion was then dialysed to remove salts, residual solvents, unwanted low molecular weight reaction side products and unbound polymer. The solid content of the dialysed aqueous ferrofluid dispersion is 0.6%.

Part (f): Modification of Stabilisers for Iron Oxide Particles of Example 20 Part (a)

Into coated nanoparticles prepared from example 20 part (a) (70 g), N-hydroxysuccinimide (NHS, 89.3 mg) and then 1-Ethyl-3-(3-Dimethylamino-propyl)carbodiimide (EDAC, 127 mg) were added, mixed by shaking and allowed to react for 2 hours at room temperature. 291 mg of 2,2'-(Ethylenedioxy)bis-(ethylamine) was then added to the reaction mixture and allowed to react for a further 12 hours. The solution was then dialysed against excess water with numerous changes, to remove free EDAC and the reaction by-products.

Example 21

Steric Stabilization of Iron Oxide Nanoparticles of Example 1 Part (a) Using 80% poly(monoacryloxyethyl phosphate)$_{10}$-block-poly(ethylene oxide)$_{17}$ Macro Raft Agent of Example 2 Part (b) and 20% Amine Modified poly(monoacryloxyethyl phosphate)$_{10}$-block-poly(acrylamide)$_{20}$ Macro Raft Agent Part (a): Preparation of Sterically Stabilized Iron Oxide Nanoparticles from the Aqueous Ferrofluid of Example 1 Part (a) and a 80:20 Blend of the Macro-RAFT Agent of Example 2 Part (b) and the Macro-RAFT Agent of Example 2 Part (c)

Aqueous ferrofluid prepared according to example 1, part (a) (8.10 g) was diluted with MQ water (50 g) to yield a 0.5 wt % dispersion of the nanoparticles. The pH of this prepared nanoparticle dispersion was then raised to 5. A blend of macro-RAFT which consist of 50 g of at 6.0 wt % solids, 5.28 wt % of which was the macro-RAFT agent of example 2 part (b) and 0.72 wt % of which was the macro-RAFT agent of example 2 part (c) were mixed together and the pH adjusted to 5 using 0.1M NaOH. The dispersion of iron oxide, maintained at the same pH was then added to the macro-RAFT blend. The mixture was vigorously stirred for 2 hours at room temperature before the pH was adjusted to 7.0. The mixture was then left stirring for another 12 hours. At this pH the copolymer remained partially neutralized while the nanoparticles were sufficiently above their point of zero charge to also be stable. The dispersion was then dialysed to remove salts, residual solvents, unwanted low molecular weight reaction side products and unbound polymer. The solid content of the dialysed aqueous ferrofluid dispersion is 0.7%.

Part (b): Modification of Stabilisers for Iron Oxide Particles of Example 21 Part (a)

Into coated nanoparticles prepared from example 2, Part (e) (60 g), N-hydroxysuccinimide (NHS, 39.4 mg) and then 1-Ethyl-3-(3-Dimethylamino-propyl)carbodiimide (EDAC, 56.2 mg) were added, mixed by shaking and allowed to react for 2 hours at room temperature. 130 mg of 2,2'-(Ethylenedioxy)bis-(ethylamine) was then added to the reaction mixture and allowed to react for a further 12 hours. The solution was then dialysed against excess water with numerous changes, to remove free EDAC and the reaction by-products.

Example 22

Steric Stabilization of Iron Oxide Nanoparticles of Example 1 Part (a) Using 90% poly(monoacryloxyethyl phosphate)$_{10}$-block-poly(ethylene oxide)$_{17}$ Macro Raft Agent of Example 2 Part (b) and 10% Amine Modified poly(monoacryloxyethyl phosphate)$_{10}$-block-poly(acrylamide)$_{20}$ Macro Raft Agent Part (a): Preparation of Sterically Stabilized Iron Oxide Nanoparticles from the Aqueous Ferrofluid of Example 1 Part (a) and a 90:10 Blend of the Macro-RAFT Agent of Example 2 Part (b) and the Macro-RAFT Agent of Example 2 Part (c)

Aqueous ferrofluid prepared according to example 1, part (a) (8.10 g) was diluted with MQ water (50 g) to yield a 0.5 wt % dispersion of the nanoparticles. The pH of this prepared nanoparticle dispersion was then raised to 5. A blend of macro-RAFT which consist of 50 g of at 6.3 wt % solids, 6.4 wt % of which was the macro-RAFT agent of example 2 part (b) and 05.9 wt % of which was the macro-RAFT agent of example 2 part (c) were mixed together and the pH adjusted to 5 using 0.1M NaOH. The dispersion of iron oxide, maintained at the same pH was then added to the macro-RAFT blend. The mixture was vigorously stirred for 2 hours at room temperature before the pH was adjusted to 7.0. The mixture was then left stirring for another 12 hours. At this pH the copolymer remained partially neutralized while the nanoparticles were sufficiently above their point of zero charge to also be stable. The dispersion was then dialysed to remove salts, residual solvents, unwanted low molecular weight reaction side products and unbound polymer. The solid content of the dialysed aqueous ferrofluid dispersion is 0.87%.

Part (b): Amine Modification of Stabilisers for Iron Oxide Particles of Example 22 Part (a Into coated nanoparticles prepared from example 2 part (a) (60 g), N-hydroxysuccinimide (NHS, 24.7 mg) and then 1-Ethyl-3-(3-Dimethylamino-propyl)carbodiimide (EDAC, 34 mg) were added, mixed by shaking and allowed to react for 2 hours at room temperature. 18.2 mg of 2,2'-(Ethylenedioxy)bis-(ethylamine) was then added to the reaction mixture and allowed to react for a further 12 hours. The solution was then dialysed against excess water with numerous changes, to remove free EDAC and the reaction by-products.

Example 23

Stabilisation of Iron Oxide Nanoparticles with Leuconostoc Mesenteroides Dextran (Average Molecular Weight 35,000-45,000 from Sigma Aldrich) (Example 23 is a Comparative Example)

25 ml of 0.5 M $FeCl_2/4H_2O$ in solutions and 25 ml of 1M $FeCl_3/6H_2O$ in solution was magnetically stirred in a 500 ml 3 neck round bottom flask. The solution mixture was diluted by adding 100 ml of Mili-Q water and the resulting solution placed in an oil bath at 70° C. After 10 minutes dextran solution (15%, 50 ml) was then added followed by ammonia solution (28% 30 ml). The mixture was kept at 70° C. for a further 45 minutes. The reaction mixture was cooled to room temperature and dialysed against MQ water to remove excess ammonia. The water was changed at least three times. Larger aggregates were removed by magnetic sedimentation. The volume of the dispersion was reduced to about 100 ml by using a rotary evaporator. The final dispersion was sonicated at 70% AMP using an ultrasonicator for 10 minutes followed by sonication at 30% AMP for 30 minute.

Example 24

Steric Stabilization of Iron Oxide Nanoparticles of Example 1 Part (a) Using 98% poly(monoacryloxyethyl phosphate)$_{10}$-block-poly(ethylene oxide)$_{17}$ Macro Raft Agent and 2% Amine Modified poly(monoacryloxyethyl phosphate)$_{10}$-block-poly(acrylamide)$_{20}$ Macro Raft Agent

Part (a): Preparation of Sterically Stabilized Iron Oxide Nanoparticles from the Aqueous Ferrofluid of Example 1 Part (a) and a 98:2 Blend of the Macro-RAFT Agent of Example 2 Part (b) and the Macro-RAFT Agent of Example 2 Part (c). [EP341063]

Aqueous ferrofluid prepared according to example 1, part (a) (8.10 g) was diluted with MQ water (50 g) to yield a 0.5 wt % dispersion of the nanoparticles. The pH of this prepared nanoparticle dispersion was then raised to 5. A blend of macro-RAFT which consist of 50 g of at 6.48 wt % solids, 6.4 wt % of which was the macro-RAFT agent of example 2 part (b) and 0.08 wt % of which was the macro-RAFT agent of example 2 part (c) were mixed together and the pH adjusted to 5 using 0.1M NaOH. The dispersion of iron oxide, maintained at the same pH was then added to the macro-RAFT blend. The mixture was vigorously stirred for 2 hours at room temperature before the pH was adjusted to 7.0. The mixture was then left stirring for another 12 hours. At this pH the copolymer remained partially neutralized while the nanoparticles were sufficiently above their point of zero charge to also be stable. The dispersion was then dialysed to remove salts, residual solvents, unwanted low molecular weight reaction side products and unbound polymer. The solid content of the dialysed aqueous ferrofluid dispersion is 0.8%.

Part (b): Amine Modification of Stabilisers of Iron Oxide Particles of Example 24 Part (a)

Into coated nanoparticles prepared from example 24, Part (a) (55 g), N-hydroxysuccinimide (NHS, 5.1'mg) and then 1-Ethyl-3-(3-Dimethylamino-propyl)carbodiimide (EDAC, 6.8 mg) were added, mixed by shaking and allowed to react for 2 hours at room temperature. 2,2'-(Ethylenedioxy)bis-(ethylamine) (18.2 mg) was then added to the reaction mixture, which was allowed to react for a further 12 hours. The solution was then dialysed against excess water with numerous changes, to remove free EDAC and the reaction by-products.

Example 25

General Method for Preparation of Spheroids

Human DLD-1 colon cancer cells and human PA-1 ovarian cancer cells were obtained from the American Type Culture Collection (Manassas, Va., USA). Cells were maintained in complete media (Advanced DMEM (Invitrogen) and supplemented with 2% foetal bovine serum (Sigma) and 2 mM Glutamax™ (Invitrogen)) at 37° C. in a humidified, 5% $CO_2$ atmosphere. Spheroids were formed by plating $1.5 \times 10^5$ cells/ml onto agarose coated 96 well imaging plates (BD Biosciences) and the cells allowed to aggregate for 72 hrs at 37° C. in a humidified, 5% $CO_2$ atmosphere resulting in the formation of single spheroid per well.

Example 26

Assessment of Cytotoxicity of Active Compounds and Nanoparticles

Active compounds and/or nanoparticles were diluted as required in cell media immediately prior to the assay. Cytotoxicity was determined using the MTT assay as follows. $1 \times 10^5$ cells were seeded onto each well of flat bottomed 96-well plates and allowed to attach overnight. Solutions of compounds+/−nanoparticles were added to triplicate wells at concentrations spanning a 4-log range and incubated for 72 hrs. MTT (3-(4, 5-dimethylthiazolyl-2)-2,5-diphenyltetrazolium bromide) (1.0 mM) was added to each well and were incubated for a further 4 hrs. The culture medium was removed from each well, DMSO (150 μL) was added, the plate shaken for 5 seconds and the absorbance measured immediately at 600 nm in a Victor$^3$V microplate reader (Perkin Elmer). $IC_{50}$ values were determined as the drug concentration that reduced the absorbance to 50% of that in untreated control wells. At least three independent experiments were performed for each compound with triplicate readings in each experiment. Cytotoxicity values for all active compounds used are listed in Table 2.

Example 27

General Method for Treating the Cancer Spheroids of Example 5 with (a) Nanoparticles Alone, (b) Co-Administration of Nanoparticles and Active Compound or (c) Time Course Treatment of Nanoparticle First then Active Compound All nanoparticles were sterilised either by filtration through a 0.22 μm filter or by autoclaving at 120° C., 2 KPa for 20 min in a Tomy high pressure steam sterilizer ES-315 before use in cellular assays.
(a) To the suspension of the 3 day old spheroids from example 25, 100 μl of a solution containing nanoparticles incomplete media was added to each spheroid, to yield a final concentration of particles of 10 ppm in 200 μl total volume. he spheroids were replaced in an incubator at 37° C., 5% $CO_2$. After 24 hours incubation, the nanoparticles in the media were removed by washing with excess phosphate buffered saline prior to further experimentation.

(b) To the suspension of the 3 day old spheroids from example 25, 100 µl of a solution containing active compound and nanoparticles incomplete media was added to each spheroid, to yield a final concentration of particles of 10 ppm. The concentration of the active compounds used is defined in Table 3. The spheroids were replaced in an incubator 37° C., 5% $CO_2$ atmosphere. After 24 hours incubation, the free active compound and nanoparticles in the media were removed by washing with excess phosphate buffered saline.

(c) To the suspension of the 3 day old spheroids from example 25, 100 µl of a solution containing nanoparticles in complete media was added to each spheroid, to yield a final concentration of particles of 10 ppm. The spheroids were replaced in an incubator at 37° C., 5% $CO_2$. After 24 hours incubation, the spheroids were dosed with an active compound at the concentration listed in Table 2 and incubated for a further 24 hours at 37° C., 5% $CO_2$. The free active compound and nanoparticles in the media were removed by washing with excess phosphate buffer saline prior to further experimentation.

Example 28

General Method for Imaging Spheroids Treated with Nanoparticles and a Fluorescent Active Compound by Confocal Microscopy Spheroids from example 25 were treated as per example 27b and 27c then transferred to a glass bottomed 35 mm dish (Mattek) and imaged on an Olympus FV1000 confocal microscope using an Olympus UPLAPO 10×/0.40 air objective lens. Single confocal images through the central region of the spheroid were taken. Excitation and emission settings were fluorophore dependent: Doxorubicin ex:559 nm em:575-675; Mitoxantrone ex:405 nm, em:575-675

Example 29

General Method for Measuring Effectiveness of Active Compound+/−Nanoparticles in Spheroids (Outgrowth Assay)

Spheroids from example 25 were treated as per example 27b and 27c. The spheroids were then transferred to a 24 well plate using a wide bore transfer pipette and the medium replaced with 1 mL of fresh media in each well. The spheroids were then incubated for 48 hours at 37° C. in a 5% $CO_2$ humidified environment, allowing the spheroid to attach to the plate and the cells to grow out from the spheroid onto the surface of the plate. Hoechst 33342 was then added to the wells and incubated for 30 minutes at 37° C. in a 5% $CO_2$ humidified environment. Widefield fluorescence images of the brightfield and Hoechst 33342 stained nuclei were taken of the cells that had grown out from the spheroid (Olympus CellR). To quantitate the outgrowth, the number of nuclei within a 60° angle from the edge of the spheroid was counted. These values were then plotted in a graph normalised to spheroids treated with active compound alone or untreated control spheroids for comparison.

Example 30

Sterically Stabilised Nanoparticles are Able to Penetrate into Spheroids

Spheroids from example 25 were treated as per example 27a with particles from example 2 and washed with phosphate buffered saline, followed by primary fixation with 2.5% glutaraldehyde solution and secondary fixation with 1% osmium tetroxide. The spheroids were washed then dehydrated in a gradient of ethanol and infiltrated with Spurr's Resin. Ultra-thin sections with a nominal thickness of 95 nm were cut, placed on mesh grids and post stained with uranyl acetate and lead citrate. TEM images of the spheroid sections were obtained using a JEOL 1400 TEM at 120 kV.

The images in FIG. 1 were taken from the central region of the spheroid and show an accumulation of nanoparticles (darker stained areas as indicated with arrows) within the cytoplasm of the cells. The enlarged region indicated by the box shows the well dispersed individual nanoparticles.

Example 31

The Effect of Nanoparticles on Drug Diffusion

Figure 2:
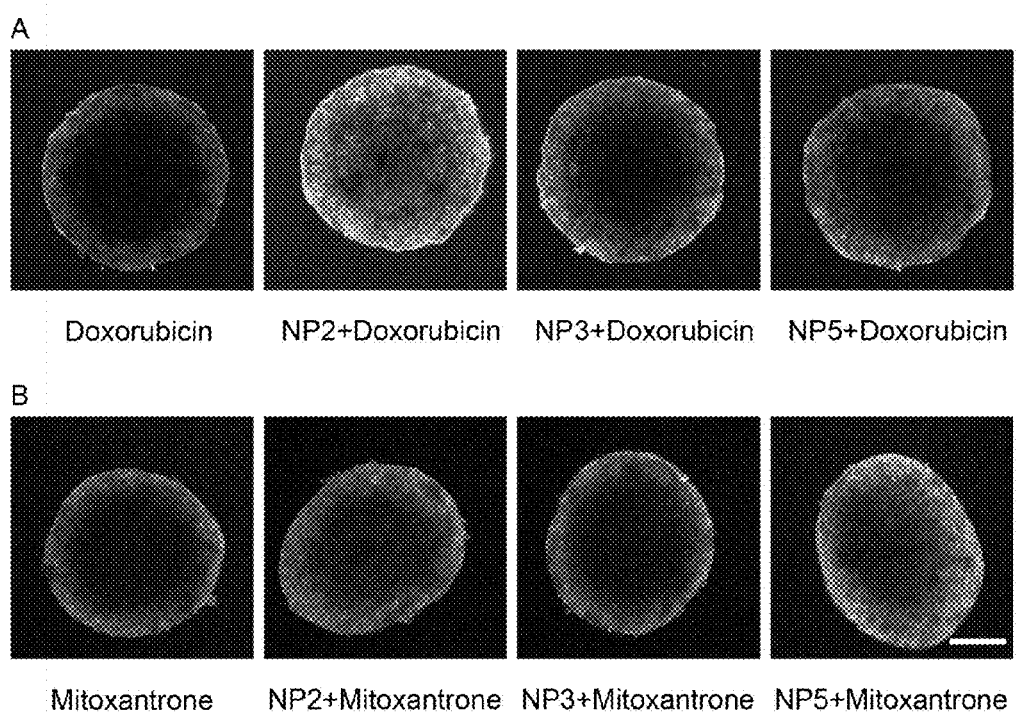
FIG. 2: Nanoparticles can influence the diffusion of fluorescent active compounds. Co-administration of the fluorescent active compounds a) doxorubicin and b) mitoxantrone with nanoparticles from examples 2, 3, and 5. Single confocal images of fluorescent drug diffusion into DLD-1 spheroids. Scale bar 200 µm.

DLD-1 spheroids prepared as per example 25 were dosed as per the protocol in example 27a with nanoparticles from examples 2, 3, and 5) and imaged under conditions described in example 28. Doxorubicin alone diffused approximately 70 µm into the spheroid. Co-administration of doxorubicin and NP3 or 5 enhanced the spheroid penetration of doxorubicin to approximately 100 µm. In contrast, co-administration of NP2 and doxorubicin resulted in doxorubicin diffusion throughout the entire spheroid (FIG. 2A). Mitoxantrone alone also diffused approximately 70 µm into the spheroid. Co-administration of NP3 and mitoxantrone had little effect on mitoxantrone diffusion, whereas co-administration of mitoxantrone and NP2 or NP5 significantly enhanced the diffusion of mitoxantrone into the spheroid (FIG. 2B).

Example 32

The Effect of Nanoparticles on Spheroid Viability

Figure 3:
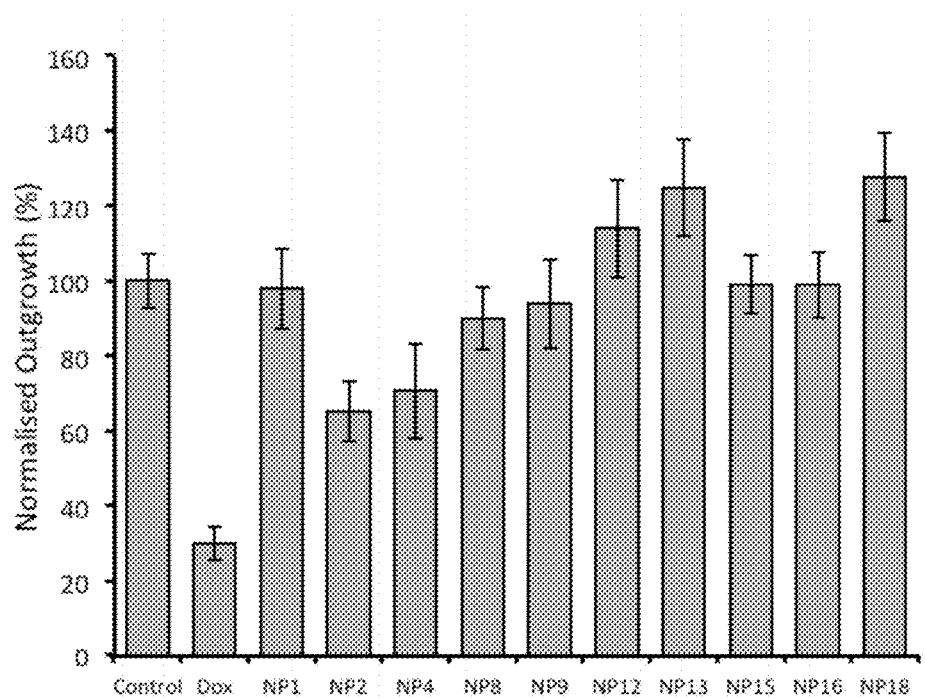
FIG. 3: The majority of nanoparticles tested did not affect cellular outgrowth from spheroids. Plot of normalised cellular outgrowth as described in example 29 of the nanoparticles listed in examples 1, 2, 4, 8, 9, 12, 13, 15, 16, and 18. Error bars represent standard error.

DLD-1 spheroids prepared as per example 25 were dosed as per the protocol in example 27a with nanoparticles from examples 1, 2, 4, 8, 9, 12, 13, 15, 16, and 18. The effectiveness of nanoparticles alone in spheroids was assessed as per example 29. It was found that the majority of nanoparticles tested had little cytotoxic effect as shown in FIG. 3.

Example 33

Figure 4:
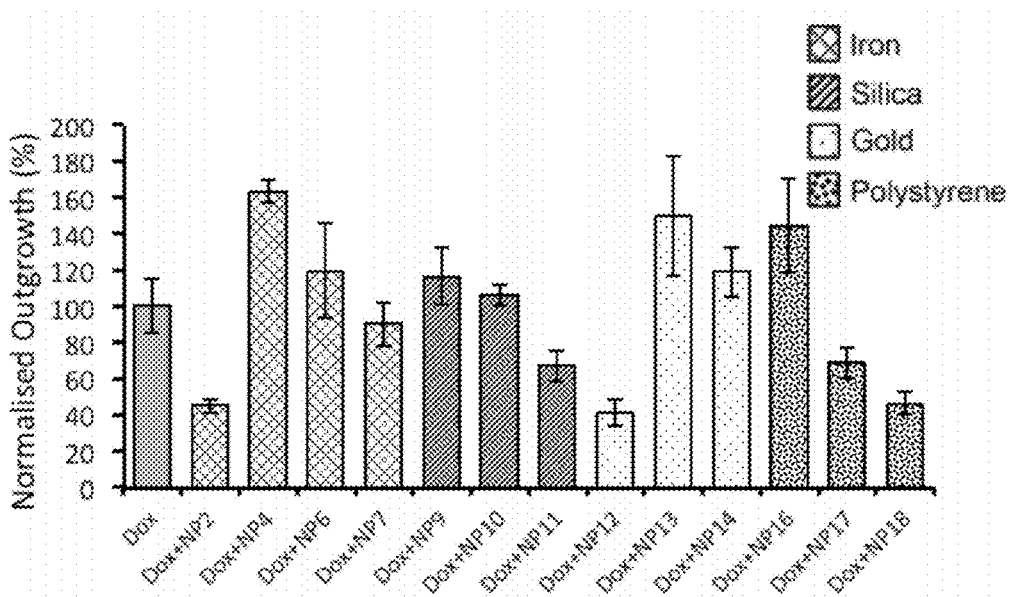
FIG. 4: Composition of the nanoparticle core does not influence nanoparticle effectiveness. Plot of normalised cellular outgrowth as described in example 29 of the nanoparticles from examples 2, 4, 6, 7, 9, 10, 11, 12, 13, 14, 16, 17, and 18, co-administered with doxorubicin. The untreated control spheroids had a normalised outgrowth value of 331%+/−23. Error bars represent standard error.

The Effect of Nanoparticles with Different Core Types on the Viability of Spheroids when Co-Administered with Doxorubicin DLD-1 spheroids prepared as per example 25 were dosed as per the protocol in example 27b with nanoparticles from examples 2, 4, 6, 7, 9, 10, 11, 12, 13, 14, 16, 17, and 18 and doxorubicin. Effectiveness was determined as per example 29. FIG. 4 shows that co-administration of nanoparticles NP2 (iron core), NP11(silica core), NP12 (gold core), and NP18 (polystyrene core) with doxorubicin was more effective than doxorubicin treatment alone as shown by the decreased cellular outgrowth from the spheroids. The composition of the nanoparticle core does not correlate with effectiveness.

Example 34

Figure 5:
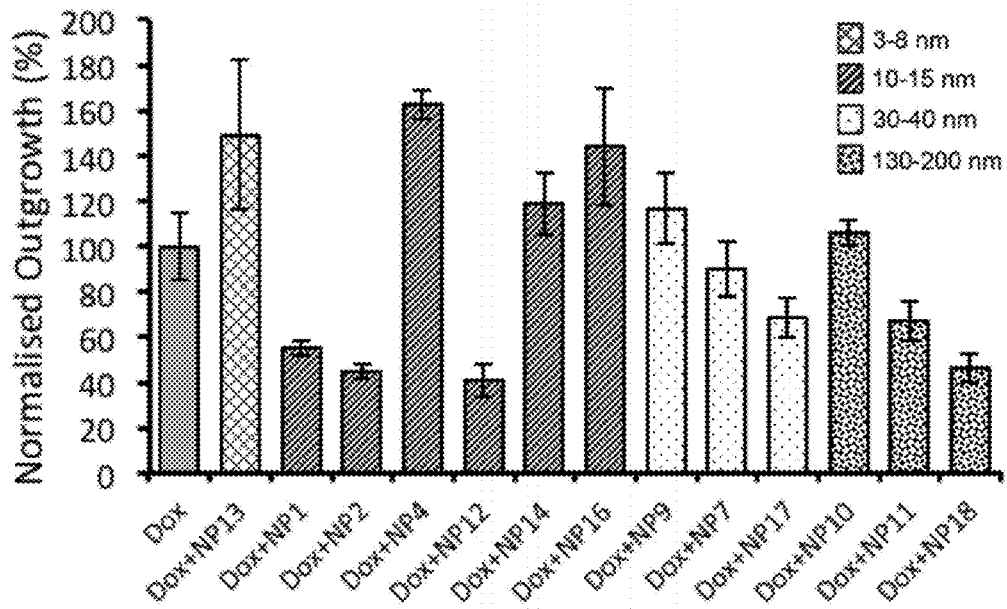
FIG. 5: Nanoparticle size does not correlate with nanoparticle effectiveness. Plot of normalised cellular outgrowth as described in example 29 of the nanoparticles listed in examples 1, 2, 4, 7, 9, 10, 11, 12, 13, 14, 16, 17, and 18 co-administered with doxorubicin. The untreated control spheroids had a normalised outgrowth value of 331%+/−23. Error bars represent standard error.
Figure 6:
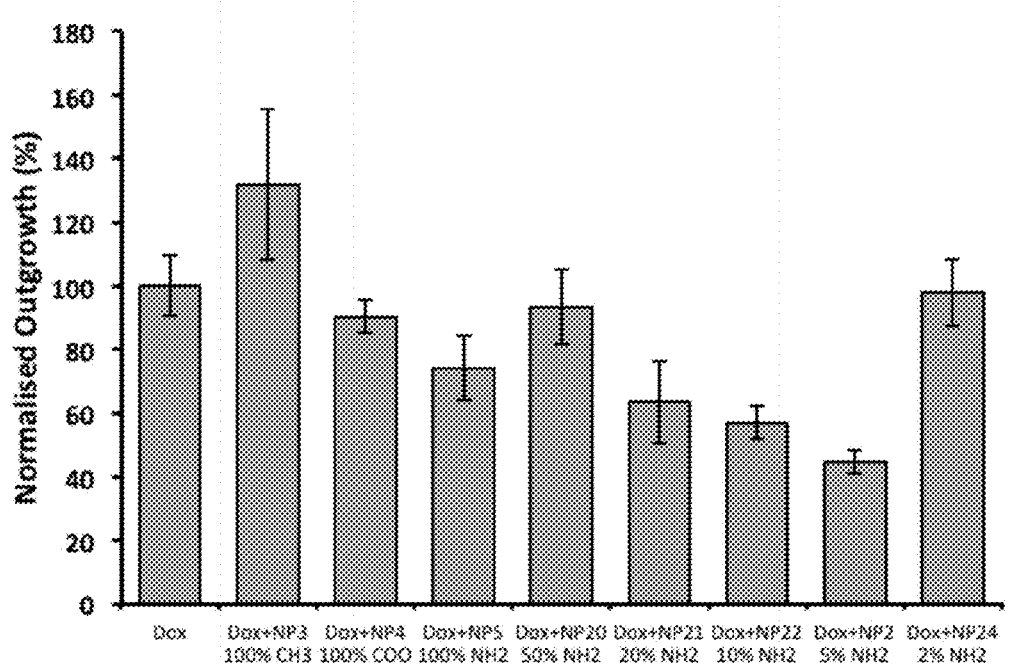
FIG. 6: Nanoparticles stabilised with 5-10% amine functionalised polymer increase the effectiveness of doxorubicin. Plot of normalised cellular outgrowth as described in example 29 of the nanoparticles listed in examples 2, 3, 4, 5, 20, 21, 22, and 24, co-administered with doxorubicin. The untreated control spheroids had a normalised outgrowth value of 331%+/−23. Error bars represent standard error.

The Effect of Nanoparticles with Different Core Sizes on the Viability of Spheroids when Co-Administered with Doxorubicin DLD-1 spheroids prepared as per example 25 were dosed as per the protocol in example 27b with nanoparticles from examples 1, 2, 4, 7, 9, 10, 11, 12, 13, 14, 16, 17, and 18 and doxorubicin. Effectiveness was determined as per example 29. Several different nanoparticles with a range of core sizes from 10 nm to 200 nm when co-administered with doxorubicin were shown to be more effective than doxorubicin alone (FIG. 5). It was shown that co-administration of particles NP1, NP2, NP12 and NP18 co-administered with doxorubicin was approximately 50% more effective than doxorubicin treatment alone.

Example 35

The Effect of the Functionalised Stabiliser End Group on Spheroid Viability when Co-Administered with Doxorubicin DLD-1 spheroids prepared as per example 25 were dosed as per the protocol in example 27b with nanoparticles listed in examples 2, 3, 4, 5, 20, 21, 22, and 24 and doxorubicin. Effectiveness was determined as per example 29. It was found that the amine functionalised end group effected spheroid viability when co-administered with doxorubicin. By varying the percentage of amine functionalised groups on the surface of the nanoparticles, we found that particles containing between 5-20% amine functionalised end groups were the most effective when co-administered with doxorubicin. Doxorubicin was the most effective when co-administered with nanoparticles containing stabilisers with 5% amine functionalised end groups.

Example 36

Figure 7:
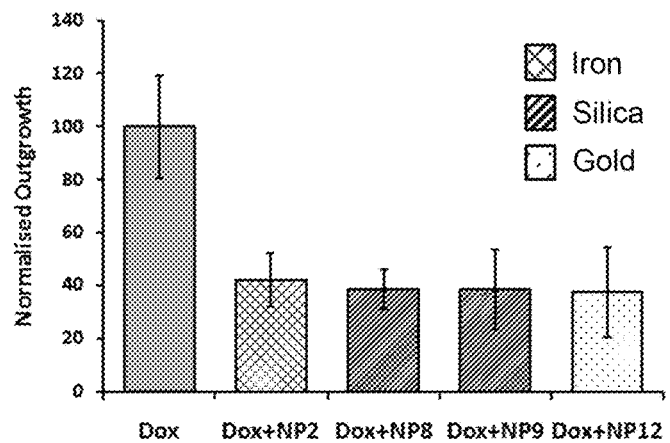
FIG. 7: Effectiveness of co-administration of NPs with 5% amine functionalised stabiliser end group coatings with different cores and doxorubicin compared to doxorubicin alone. Plot of normalised cellular outgrowth as described in example 29 of the nanoparticles listed in examples 2, 8, 9, and 12 co-administered with doxorubicin. The untreated control spheroids had a normalised outgrowth value of 331%+/−23. Error bars represent standard error.
Figure 8:
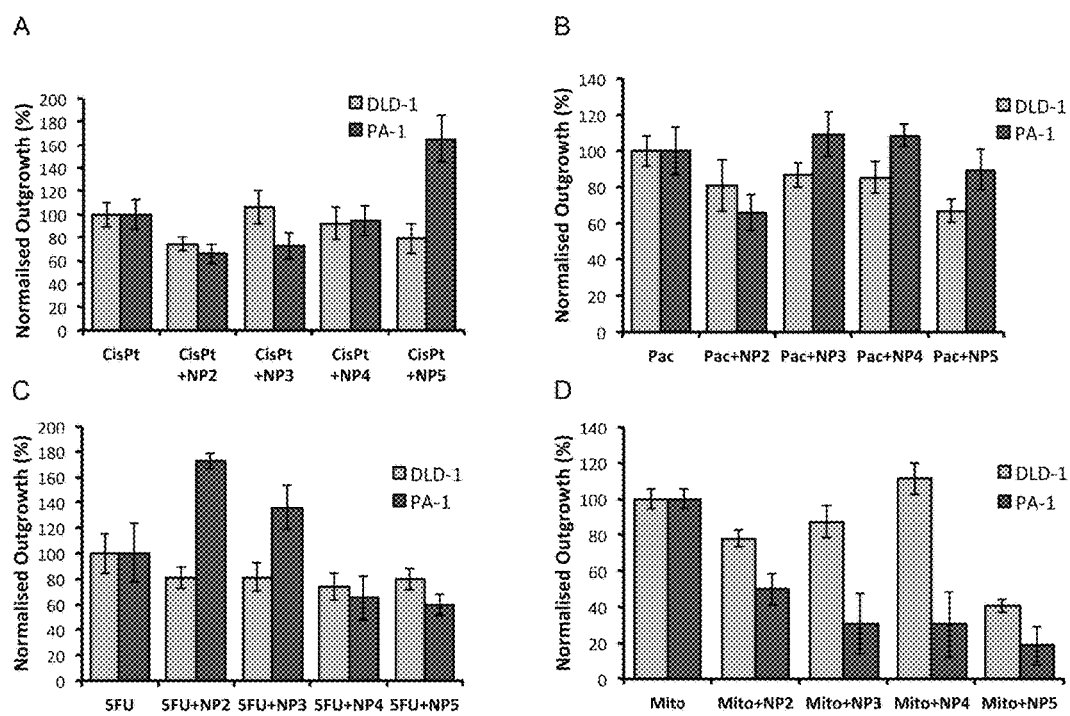
FIG. 8: The effect of the active compounds when co-administered with nanoparticles on the viability of spheroids made from two different cancer cell lines. Plot of normalised cellular outgrowth as described in example 29 of the nanoparticles listed in examples 2, 3, 4, and 5 co-administered with active compounds (Table 2). The untreated DLD-1 control spheroids had a normalised outgrowth value of 331%+/−23. The untreated PA-1 control spheroids had a normalised outgrowth value of 294%+/−21. Error bars represent standard error.

Nanoparticles of Different Cores Stabilised with 5% Amine Functionalised End Groups Co-Administered to Spheroids with Doxorubicin DLD-1 spheroids prepared as per example 25 were dosed as per the protocol in example 27b with nanoparticles listed in examples 2, 8, 9 and 12 and doxorubicin. Effectiveness was determined as per example 29. Nanoparticles stabilised with 5% amine functionalised end groups were made with different cores and it was shown that all were more effective than doxorubicin alone and had a similar level of effectiveness when co-administered with doxorubicin (FIG. 7).

Example 37

The Effect of the Active Compounds when Co-Administered with Nanoparticles on the Viability of Spheroids Made from Two Different Cancer Cell Lines DLD-1 and PA-1 spheroids were prepared as per example 25 and dosed as per the protocol in example 27b with nanoparticles listed in examples 2, 3, 4, and 5 and active compounds. Effectiveness was determined as per example 29. The majority of particles and active compounds had similar effectiveness between the two cell lines, with the exception of mitoxantrone. Co-administration of mitoxantrone and nanoparticles was significantly more effective in the PA-1 cell ovarian cancer cell line compared to the DLD-1 colorectal cancer line.

Example 38

Figure 9:
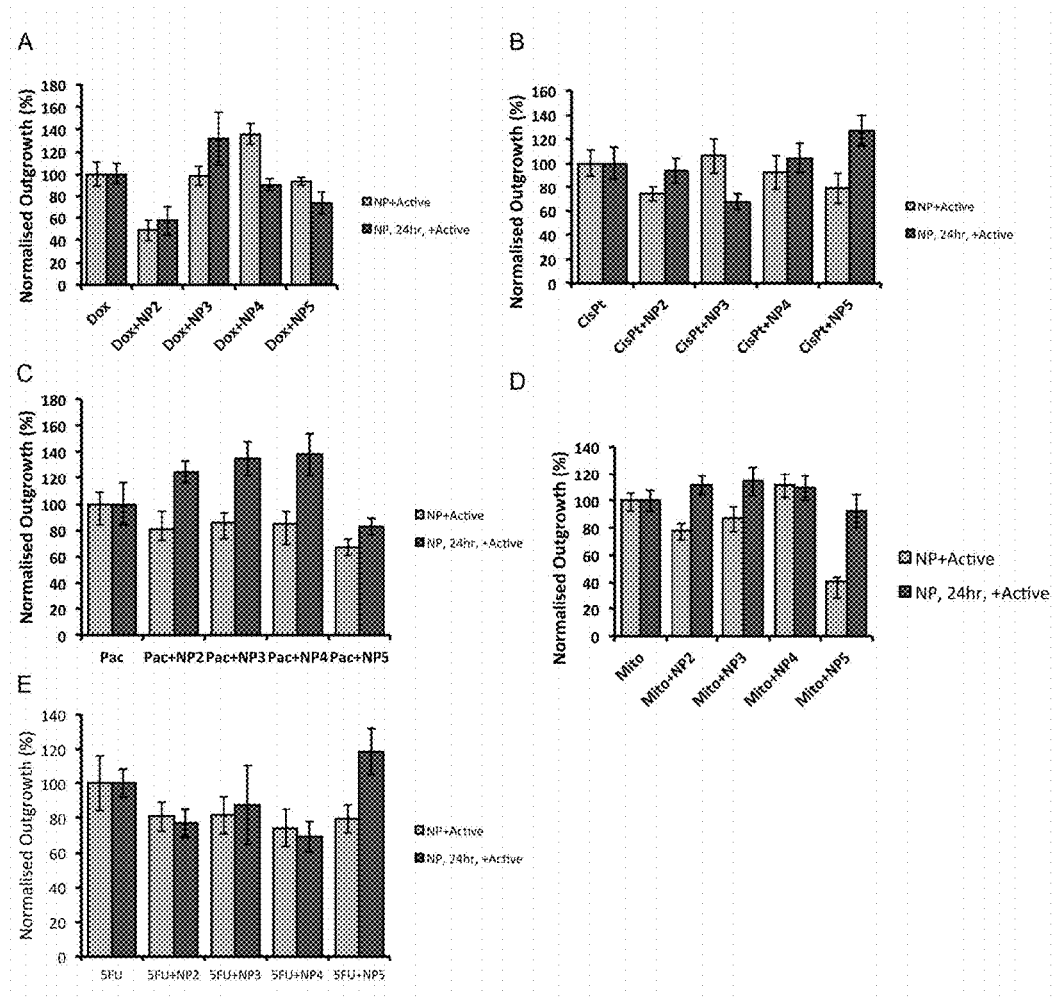
FIG. 9: Effect of delayed administration of active compound compared to co-administration of active compound and nanoparticles. Plot of normalised cellular outgrowth as described in example 29 of the nanoparticles listed in examples 2, 3, 4, and 5 DLD-1 spheroids were either co-administered nanoparticles and active compound (light grey bars) or administered nanoparticles, then 24 hours later treated with active compound (dark grey bars). The untreated DLD-1 control spheroids had a normalised outgrowth value of 331%+/−23. Error bars represent standard error.
Figure 10:
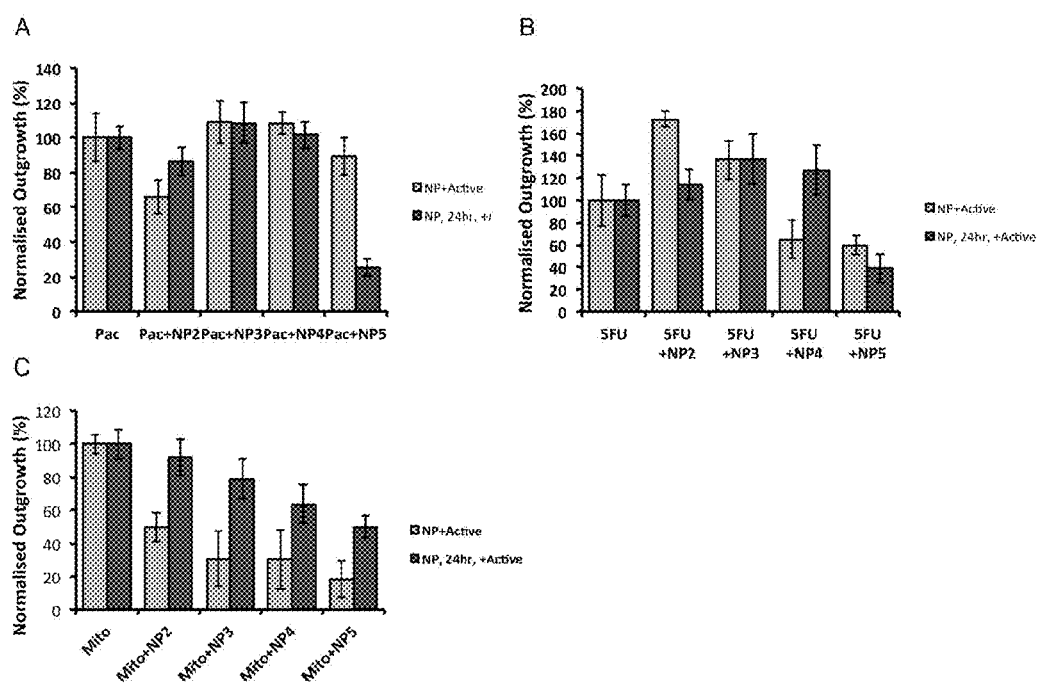
FIG. 10: Effect of delayed administration of active compound compared to co-administration of active compound and nanoparticles. Plot of normalised cellular outgrowth as described in example 29 of the nanoparticles listed in examples 2, 3, 4, and 5. PA-1 spheroids were either co-administered nanoparticles and active compound (light grey bars) or administered nanoparticles, then 24 hours later treated with active compound (dark grey bars). The untreated PA-1 control spheroids had a normalised outgrowth value of 294%+/−21. Error bars represent standard error.

Comparative Example Between Co-Administration of Nanoparticles and Active Compounds, and Administration of Nanoparticles with Delayed Administration of Active Compounds in Two Different Cell Lines DLD-1 and PA-1 spheroids were prepared as per example 25 and dosed as per the protocol in example 27b and 27c with the nanoparticles listed in examples 2, 3, 4, and 5 and active compounds. Effectiveness was determined as per example 29. FIGS. 9 and 10 show that for some particle and active combinations e.g. 5FU+NP3 there is no difference in effectiveness in either cell line for either mode of treatment. In general however, there is little correlation between treatment schedule and effectiveness between the two cell lines tested. It will be important to determine which nanoparticle/active combination is most effective for each cancer type. It should be noted that mitoxantrone requires the co-administration of nanoparticles in PA-1 cells for greatest effectiveness.

Example 39

Figure 11:
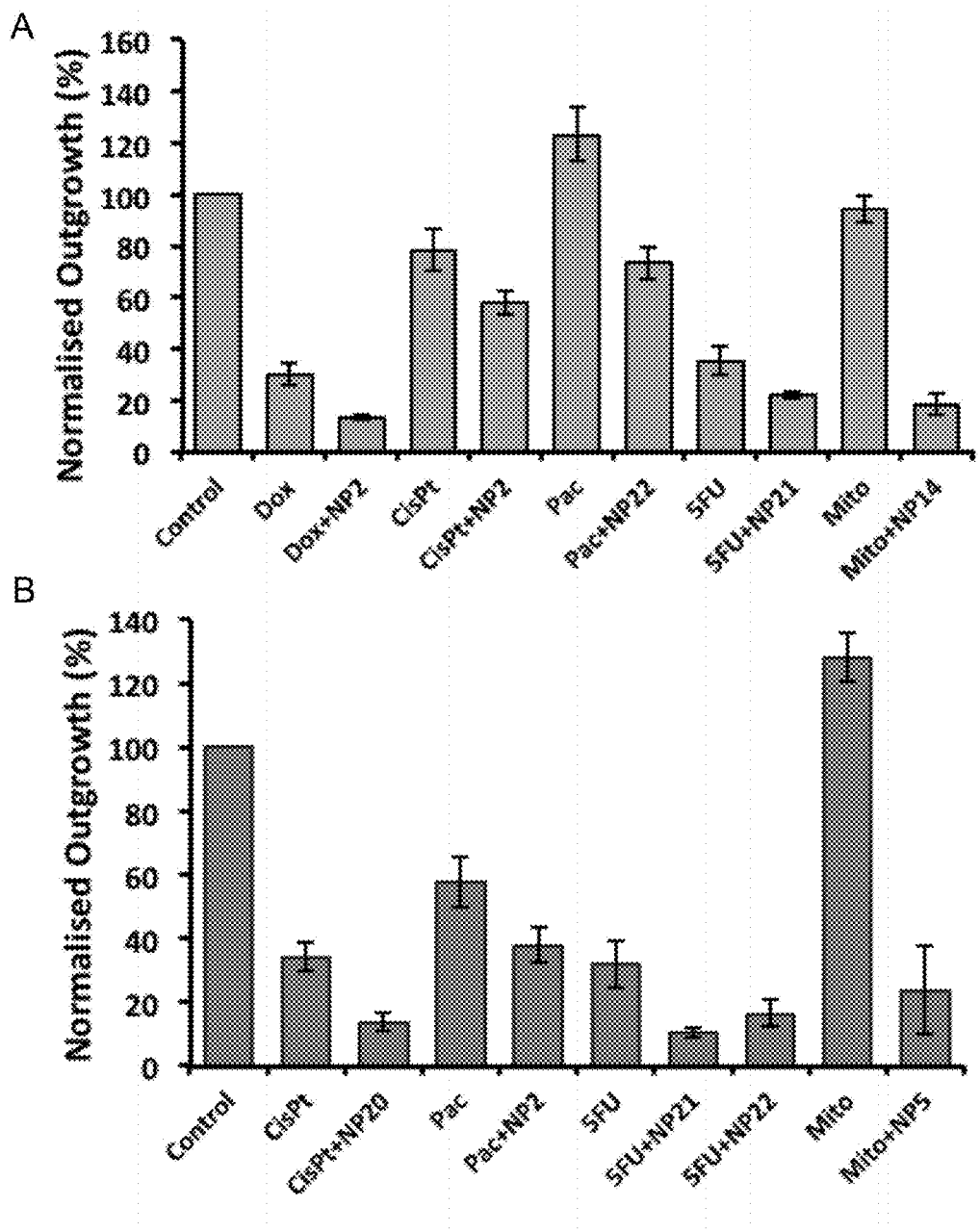
FIG. 11: The most effective co-administered nanoparticle and active combinations for DLD-1 and PA-1 cells. Plot of normalised cellular outgrowth as described in example 29 of the nanoparticles listed in examples 2, 5, 14, 20, 21, and 22, co-administered with active compounds in DLD-1 spheroids (A) and PA-1 spheroids (B). Error bars represent standard error.

Examples of the Most Effective Co-Administered Combination of Nanoparticles and Active Compound for Each Active Compound Tested DLD-1 and PA-1 spheroids were prepared as per example 25 and dosed as per the protocol in example 27b with the nanoparticles listed in examples 2, 5, 14, 20, 21, and 22 and active compounds. Effectiveness was determined as per example 29. The results presented are for the most effective nanoparticle(s) co-administered with each active compound in both DLD-1 spheroids (FIG. 11A) and PA-1 spheroids (FIG. 11B).

Example 40

Treating the Cancer Spheroids of Example 25 with the Iron Oxide Nanoparticles of Examples 1 and 2 to Enable Spheroid Penetration by Cisplatin DLD-1 spheroids prepared as per example 25 were dosed as with 100 μl of solution of complete media containing cisplatin and iron oxide nanoparticles from examples 1 and 2 to yield a final concentration of both cisplatin and iron oxide of 6 ppm. The spheroids with iron oxide particles and cisplatin were replaced in the incubator and maintained at 37° C. in a 5% $CO_2$ atmosphere. After 48 hours incubation, the free cisplatin and nanoparticles in the media were washed with excess phosphate buffered saline. Analysis by atomic absorption spectroscopy showed that after 48 hours incubation the concentration of cisplatin in the spheroids with NP1 nanoparticles, NP2 nanoparticles and without iron oxide particles was 0.60, 0.63 and 0.20 ppb, respectively, a 3-fold increase in cisplatin accumulation when nanoparticles were present.

Example 41

Figure 12:
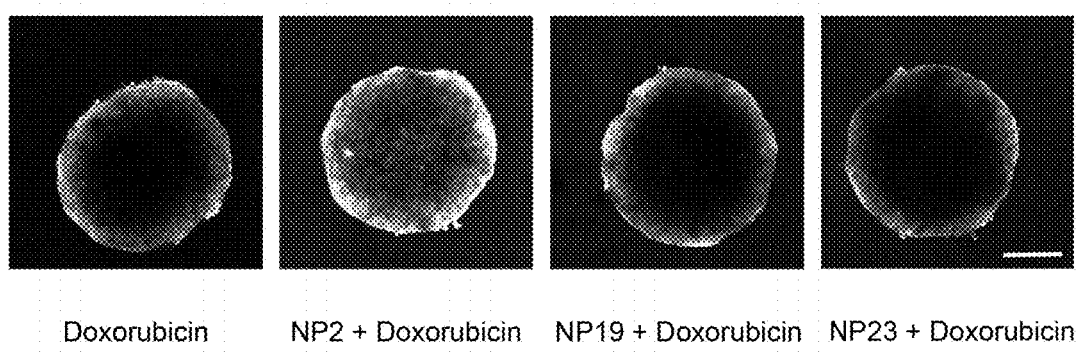
FIG. 12: The co-administration of NP2 but not NP19 or NP23 with doxorubicin promotes doxorubicin diffusion throughout the spheroid. Confocal images of doxorubicin diffusion in spheroids treated with 1 µM Doxorubicin and the nanoparticles as indicated. Scale bar 200 µm.

Comparative Example: Doxorubicin Penetration into Spheroids when Co-Administered with Anchored Sterically Stabilised Particles Compared to Co-Administration with Unanchored Sterically Stabilised Particles DLD-1 spheroids from example 25 were either dosed with NP2 (example 2), which are particles coated with a stabiliser containing a phosphate anchoring group or NP19 or NP23 (examples 19 and 23), which are particles coated with a stabiliser that has no anchoring portion as per example 27b. The spheroid was then imaged by confocal microscopy (as per example 28) to visualise doxorubicin fluorescence. Spheroids treated with doxorubicin and NP2 had significantly more doxorubicin fluorescence in the centre of the spheroid compared to the spheroids treated with doxorubicin alone and to spheroids treated with doxorubicin co-administered with the unanchored sterically stabilised particles NP19 and NP23 (FIG. 12).

Example 42

Potential Testing Regime to Determine the Most Effective Nanoparticle and Active Compound for Patient Tumours To identify which type(s) of nanoparticles and which type(s) of active drug and an optimum combination of nanoparticles and drug were the most effective for an individual patient, tumour biopsies would initially be tested. Several core tumour biopsies would be taken from a patient, dissected into smaller samples (approx 1 mm$^3$) and dosed with selected nanoparticle/drug combinations. Each dosed sample would be flanked by an untreated sample and a drug only to control for intra-tumour variability. After 24 hrs, the sample would be subjected to an outgrowth assay to measure the efficacy of the tumour treatments with nanoparticles/drug to determine the most effective composition and administration of nanoparticles and drug.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

LIST OF NANOPARTICLES USED TO EXEMPLIFY THIS PATENT

| Example | NPs | NP core, diameter | Coating type |
|---|---|---|---|
| 1 | NP1 | $Fe_2O_3$, 10-15 nm | 100% diCOO |
| 2 | NP2 | $Fe_2O_3$, 10-15 nm | 95% PEG 5% $NH_2$ |
| 3 | NP3 | $Fe_2O_3$, 10-15 nm | 100% PEG($CH_3$) |
| 4 | NP4 | $Fe_2O_3$, 10-15 nm | 100% COO |
| 5 | NP5 | $Fe_2O_3$, 10-15 nm | 100% $NH_2$ |
| 6 | NP6 | $Fe_2O_3$, 10-15 nm | 95% COO 5% $NH_2$ |
| 7 | NP7 | $Fe_2O_3$, 30-40 nm | 100% COO |
| 8 | NP8 | $SiO_2$, 10-15 nm | 95% PEG 5% $NH_2$ |
| 9 | NP9 | $SiO_2$, 30-40 nm | 95% PEG 5% $NH_2$ |
| 10 | NP10 | $SiO_2$, 130 nm | 100% COO |
| 11 | NP11 | $SiO_2$, 130 nm | 100% PEGAcrylate |
| 12 | NP12 | Gold, 10-15 nm | 95% PEG 5% $NH_2$ |
| 13 | NP13 | Gold, 3-8 nm | 100% COO |
| 14 | NP14 | Gold, 10-15 nm | 100% COO |
| 15 | NP15 | Gold, 30-40 nm | 100% COO |
| 16 | NP16 | PSty, ~15 nm | 100% COO |
| 17 | NP17 | PSty, ~40 nm | 100% COO |
| 18 | NP18 | PSty, ~200 nm | 100% COO |
| 19 | NP19 | $Fe_2O_3$, 10-15 nm | 10K Dextran |
| 10 | NP20 | $Fe_2O_3$, 10-15 nm | 50% PEG 50% $NH_2$ |
| 21 | NP21 | $Fe_2O_3$, 10-15 nm | 80% PEG 20% $NH_2$ |
| 22 | NP22 | $Fe_2O_3$, 10-15 nm | 90% PEG 10% $NH_2$ |
| 23 | NP23 | $Fe_2O_3$, 10-15 nm | 40K Dextran |
| 24 | NP24 | $Fe_2O_3$, 10-15 nm | 98% PEG 2% $NH_2$ |

TABLE 2

72 hr $IC_{50}$ values for the active compounds used in this study.

| Active Compound | DLD-1 | PA-1 |
|---|---|---|
| Doxorubicin (Dox) | 1 µM | 1 µM |
| Cisplatin (Cis) | 10 µM | 0.6 uM |
| Mitoxantrone (Mito) | 40 nM | 20 nM |
| Paclitaxel (Pac) | indeterminable* | indeterminable* |
| 5-Fluorouracil (5FU) | 10 µM | 10 µM |

*Paclitaxel was cytotoxic at concentrations as low as 0.1 nM in this assay.

TABLE 3

Concentrations of active compounds used for dosing in each cell line.

| Active Compound | DLD-1 | PA-1 |
|---|---|---|
| Doxorubicin (Dox) | 1 µM | 1 µM |
| Cisplatin (Cis) | 10 µM | 2 µM |
| Mitoxantrone (Mito) | 30 nM | 30 nM |
| Paclitaxel (Pac) | 10 nM | 10 nM |
| 5-Fluorouracil (5FU) | 10 µM | 10 µM |

BIBLIOGRAPHY

Arias et al. 2003, *National Vital Statistics Reports* 52:111-115

Bender et al., *Cancer Research* 52:121-126, 1992

Britz-Cunningham et al. *Journal of Nuclear Medicine* 44:1945-1961, 2003

Christiansen et al. *Molecular Cancer Therapy* 3:1493-1501, 2004

Dadachova et al. *PNAS* 101:14865-14870, 2004

Griffiths et al. *International Journal of Cancer* 81:985-992, 1999

Lawrence TS. *Oncology (Huntington)* 17:23-28, 2003

Liu et al. *Bioconjugate Chemistry* 12:7-34, 2001

Massart, *Preparation of aqueous magnetic liquids in alkaline and acidic media*. IEEE Transactions on Magnetics, 1981. MAG-17(2): p. 1247-1248

Minchinton, A. I. and Tannock, I. F., *Nat. Rev. Cancer* 2006, 6:583-592

O'Donoghue et al. *Journal of Nuclear Medicine* 36:1902-1909, 1995

Primeau et al. *Clin. Canc. Res.* 2005, 11:8782-8788

Sellers et al. *Journal of Clinical Investigation* 104:1655-1661, 1999

Waldmann, *Science* 252:1657-1662, 1991

Xue et al. *PNAS* 99:13765-13770, 2002

The invention claimed is:

1. A method of treating a solid tumour in a subject, said method comprising co-administering to said subject an effective amount of a non-cytotoxic particulate material and a cellular toxin effective to penetrate said solid tumor and induce cytotoxicity, wherein:
   (i) said non-cytotoxic particulate material is administered in the form of a dispersion in a liquid carrier, the non-cytotoxic particulate material being maintained in the dispersed state by a steric stabiliser;
   (ii) wherein said steric stabiliser comprises an anchoring portion and a steric stabilising polymeric segment;
   (iii) wherein the anchoring portion anchors the steric stabiliser to the non-cytotoxic particulate material, is different from the remainder of the steric stabiliser and has an affinity towards the surface of the particulate material and secures the steric stabiliser to the non-cytotoxic particulate material;
   (iv) wherein the cellular toxin is not attached to the non-cytotoxic particulate material; and
   (v) wherein the non-cytotoxic particulate material and cellular toxin are co-administered in two separate formulations.

2. The method according to claim 1, wherein the steric stabilising polymeric segment of the stabiliser comprises polymer selected from the group consisting of poly(acrylamide), poly(ethylene oxide), poly(hydroxyethylacrylate), poly(N-isopropylacrylamide), poly(dimethylaminoethyl methacrylate), poly(vinyl pyrrolidone), and copolymers thereof.

3. The method according to claim 1, wherein the anchoring portion comprises one or more carboxylic acid groups, one or more phosphate groups, one or more phosphinate groups, one or more thiol groups, one or more thiocarbonylthio groups, one or more sulfonic acid groups, ethoxysilyl groups, or combinations thereof.

4. The method according to claim 1, wherein the steric stabilising polymeric segment and/or the anchoring portion comprise the polymerised residue of one or more ethylenically unsaturated monomers.

5. The method according to claim 1, wherein the stabiliser has a number average molecular weight of less than about 30,000 average molecular weight (Mn).

6. The method according to claim 1, wherein the non-cytotoxic particulate material is selected from the group consisting of a metal, a metal alloy, a metal salt, a metal complex, a metal oxide, an inorganic oxide, a radioactive isotope, a polymer particle, and combinations thereof.

7. The method according to claim 1, wherein said non-cytotoxic particulate material is administered prior to the cellular toxin.

* * * * *